United States Patent
Hashimoto et al.

(10) Patent No.: US 7,514,242 B2
(45) Date of Patent: *Apr. 7, 2009

(54) PROCESS FOR PRODUCING DIPEPTIDES

(75) Inventors: Shin-ichi Hashimoto, Yamaguchi (JP); Kazuhiko Tabata, Tokyo (JP); Aya Hadakubota, Yamaguchi (JP); Hajime Ikeda, Tokyo (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 98 days.

This patent is subject to a terminal disclaimer.

(21) Appl. No.: 10/746,264

(22) Filed: Dec. 29, 2003

(65) Prior Publication Data

US 2004/0171106 A1    Sep. 2, 2004

(30) Foreign Application Priority Data

Dec. 26, 2002 (JP) ............................ 2002-376054
Dec. 18, 2003 (JP) ............................ 2003-420887

(51) Int. Cl.
*C12P 1/00* (2006.01)
*C12P 13/00* (2006.01)
*C12P 7/40* (2006.01)

(52) U.S. Cl. .......................... 435/128; 435/41; 435/136

(58) Field of Classification Search ................ 435/68.1, 435/69.1, 320.1, 252.31, 252.33, 183; 514/19
See application file for complete search history.

(56) References Cited

U.S. PATENT DOCUMENTS

2002/0064834 A1 * 5/2002 Doekel et al. ............... 435/71.1

FOREIGN PATENT DOCUMENTS

CA         2334079          1/2000
WO     WO 00/03009          1/2000

OTHER PUBLICATIONS

Steinborn et al. EMBL: AF396778, created Nov. 1, 2002, Bacillus subtilis strain A1/3 bacilysin gene cluster, complete sequence.*
Yazgan et al, Bacilysin biosynthesis by a partially-purified enzyme fraction from Bacillus subtilis, Enzyme and Microbial Technology 29 (2001), pp. 400-406.
Sakajoh et al, Cell-free synthesis of the dipeptide antibiotic bacilysin, Journal of Industrial Microbiology, 2 (1987), pp. 201-208.
Kunst et al, The complete genome sequence of the Gram-positive bacterium Bacillus subtilis, Nature, vol. 390, Nov. 20, 1997.
Database UniProt, Feb. 1, 1995, XP002314261, Database Accession No. P39641.
Database UniProt, Oct. 1, 2002, XP002314262, Database Accession No. Q8KWT3.
European Search Report dated Feb. 14, 2005 issued in connection with EP 03029955.6.
Khumtaveeporn et al, Tetrahedron Asymmetry, vol. 10 (1999), pp. 2563-2572.
Steinborn et al "Isolation of the bac gene cluster encoding bacilysin in different Bacillus species", NCBI, Protein db (GenBank) Accession No. AAM90571, Aug. 2, 2002, XP-002362028.
Steinborn et al "Isolation of the bac gene cluster encoding bacilysin in different Bacillus species", NCBI, Protein db (GenBank) Accession No. AAM90576, Aug. 2, 2002, XP-002362029.

* cited by examiner

*Primary Examiner*—Nashaat T Nashed
*Assistant Examiner*—Iqbal H Chowdhury
(74) *Attorney, Agent, or Firm*—Fitzpatrick, Cella, Harper & Scinto

(57) ABSTRACT

The present invention provides a protein which catalyzes the synthesis of a dipeptide different from L-Ala-L-Ala, a process for producing the protein which catalyzes the synthesis of a dipeptide, a process for producing a dipeptide using the protein which catalyzes the synthesis of a dipeptide, and a process for producing the dipeptide using a culture of a microorganism producing the protein which catalyzes the synthesis of a dipeptide or the like as an enzyme source.

7 Claims, 2 Drawing Sheets

US 7,514,242 B2

PROCESS FOR PRODUCING DIPEPTIDES

The present application claims benefit of Japanese application nos. 376054/2002 and 420887/2003, filed 26 Dec. 2002 and 18 Dec. 2003, respectively, the entire contents of each of which is incorporated herein by reference.

BACKGROUND OF THE INVENTION

The present invention relates to a protein which catalyzes the synthesis of a dipeptide, a process for producing the protein which catalyzes the synthesis of a dipeptide, a process for producing a dipeptide using the protein which catalyzes the synthesis of a dipeptide, a microorganism or a transformant producing the protein which catalyzes the synthesis of a dipeptide, and a process for producing the dipeptide using such microorganism or transformant.

Chemical synthesis methods (liquid phase method and solid phase method), enzymatic synthesis methods and biological synthesis methods utilizing recombinant DNA techniques are available for large-scale peptide synthesis. Currently, the enzymatic synthesis methods and biological synthesis methods are employed for the synthesis of long-chain peptides longer than 50 residues, and the chemical synthesis methods and enzymatic synthesis methods are mainly employed for the synthesis of dipeptides.

In the synthesis of dipeptides by the chemical synthesis methods, however, operations such as introduction and removal of protective groups for functional groups are necessary, and racemates are also formed. The chemical synthesis methods are thus considered to be disadvantageous in respect of cost and efficiency. They are unfavorable also from the viewpoint of environmental hygiene because of the use of large amounts of organic solvents and the like.

As to the synthesis of dipeptides by the enzymatic methods, the following methods are known: a method utilizing reverse reaction of protease (J. Biol. Chem., 119, 707-720 (1937)); methods utilizing thermostable aminoacyl t-RNA synthetase (Japanese Published Unexamined Patent Application No. 146539/83, Japanese Published Unexamined Patent Application No. 209991/83, Japanese Published Unexamined Patent Application No. 209992/83,and Japanese Published Unexamined Patent Application No. 106298/84); and methods utilizing non-ribosome peptide synthetase (hereinafter referred to as NRPS) (Chem. Biol., 7, 373-384 (2000), FEBS Lett., 498, 42-45 (2001), U.S. Pat. No. 5,795,738 and U.S. Pat. No. 5,652,116).

However, the method utilizing reverse reaction of protease requires introduction and removal of protective groups for functional groups of amino acids used as substrates, which causes difficulties in raising the efficiency of peptide-forming reaction and in preventing peptide-degradating reaction. The methods utilizing thermostable aminoacyl t-RNA synthetase have the defects that the expression of the enzyme and the prevention of side reactions forming by-products other than the desired products are difficult. The methods utilizing NRPS are inefficient in that the expression of the enzyme by recombinant DNA techniques is difficult because of its large enzyme molecule size and that the supply of coenzyme 4'-phosphopantetheine is necessary.

On the other hand, there exist a group of peptide synthetases that have enzyme molecular weight lower than that of NRPS and do not require coenzyme 4'-phosphopantetheine; for example, γ-glutamylcysteine synthetase, glutathione synthetase, D-alanine-D-alanine (D-Ala-D-Ala) ligase, and poly-γ-glutamate synthetase. Most of these enzymes utilize D-amino acids as substrates or catalyze peptide bond formation at the γ-carboxyl group. Because of such properties, they can not be used for the synthesis of dipeptides by peptide bond formation at the α-carboxyl group of L-amino acid.

The only known example of an enzyme capable of dipeptide synthesis by the activity to form a peptide bond at the α-carboxyl group of L-amino acid is bacilysin (dipeptide antibiotic derived from a microorganism belonging to the genus *Bacillus*) synthetase. Bacilysin synthetase is known to have the activity to synthesize bacilysin [L-alanyl-L-anticapsin (L-Ala-L-anticapsin)] and L-alanyl-L-alanine (L-Ala-L-Ala), but there is no information about its activity to synthesize other peptides (J. Ind. Microbiol., 2, 201-208 (1987) and Enzyme. Microbial. Technol., 29, 400-406 (2001)).

As for the bacilysin biosynthetase genes in *Bacillus subtilis* 168 whose entire genome information has been clarified (Nature, 390, 249-256 (1997)), it is known that the productivity of bacilysin is increased by amplification of bacilysin operons containing ORFs ywfA-F (WO00/03009 pamphlet). However, it is not known whether an ORF encoding a protein having the activity to ligate two or more amino acids by peptide bond is contained in these ORFs, and it contained, which ORF encodes the protein.

An object of the present invention is to provide a protein which catalyzes the synthesis of a dipeptide which is different from L-Ala-L-Ala and for which no enzymatic synthesis method using peptide synthetase or the like has so far been proposed, and a protein for the synthesis of the dipeptide; DNA encoding the protein having the dipeptide-synthesizing activity; a recombinant DNA comprising the DNA; a transformant carrying the recombinant DNA; a process for producing the protein having the dipeptide-synthesizing activity; an enzymatic method for synthesizing the dipeptide using the protein having the dipeptide-synthesizing activity or the protein for the dipeptide synthesis; and a process for producing the dipeptide using, as an enzyme source, a culture of a microorganism having the ability to produce the protein having the dipeptide-synthesizing activity or the protein for the dipeptide synthesis, or the like.

An object of the present invention is to provide a protein which catalyzes the synthesis of a dipeptide which is different from L-Ala-L-Ala and for which no enzymatic synthesis method using peptide synthetase or the like has so far been proposed, and a protein for the synthesis of the dipeptide; DNA encoding the protein having the dipeptide-synthesizing activity; a recombinant DNA comprising the DNA; a transformant carrying the recombinant DNA; a process for producing the protein having the dipeptide-synthesizing activity; an enzymatic method for synthesizing the dipeptide using the protein having the dipeptide-synthesizing activity or the protein for the dipeptide synthesis; and a process for producing the dipeptide using, as an enzyme source, a culture of a microorganism having the ability to produce the protein having the dipeptide-synthesizing activity or the protein for the dipeptide synthesis, or the like.

SUMMARY OF THE INVENTION

The present invention relates to the following (1) to (20).

(1) A protein selected from the group consisting of [1] to [4] below, provided that a protein consisting of the amino acid sequence shown in SEQ ID NO: 1 is excluded:

[1] a protein comprising the amino acid sequence shown in any of SEQ ID NOS: 2 to 8;

[2] a protein comprising an amino acid sequence wherein one or more amino acid residues are deleted, substituted or added in the amino acid sequence shown in any of SEQ ID NOS: 1 to 8 and catalyzing the synthesis of a dipeptide represented by formula (I):

$$R^1—R^2 \qquad (I)$$

(wherein $R^1$ and $R^2$, which may be the same or different, each represent an amino acid, provided that both $R^1$ and $R^2$ cannot represent L-alanine at the same time);

[3] a protein comprising an amino acid sequence which shows 65% or more similarity to the amino acid sequence shown in any of SEQ ID NOS: 1 to 8 and catalyzing the synthesis of dipeptide represented by formula (I); and

[4] a protein comprising an amino acid sequence which shows 80% or more similarity to the amino acid sequence shown in SEQ ID NO: 17 and catalyzing the synthesis of a dipeptide represented by formula (I).

(2) A nucleic acid sequence selected from the group consisting of [1] to [5] below, provided that the nucleotide sequence shown in SEQ ID NO: 9 is excluded, and the RNA equivalent thereof, are:

[1] a nucleic acid sequence encoding the protein according to the above (1);

[2] a nucleic acid sequence comprising the nucleotide sequence shown in any of SEQ ID NOS: 10 to 16 and 36;

[3] a nucleic acid sequence which hybridizes with a nucleic acid sequence comprising the complement of a nucleotide sequence shown in any of SEQ ID NOS: 9 to 16 and 36 under stringent conditions and which nucleic acid sequence encodes a protein which catalyzes the synthesis of a dipeptide represented by formula (I):

$$R^1—R^2 \qquad (I)$$

(wherein $R^1$ and $R^2$, which may be the same or different, each represent an amino acid, provided that both $R^1$ and $R^2$ cannot represent L-alanine at the same time);

[4] a nucleic acid sequence comprising a nucleotide sequence which shows 80% or more similarity to the nucleotide sequence shown in SEQ ID NO: 18 and encoding a protein which catalyzes the synthesis of a dipeptide represented by formula (I); and

[5] a nucleic acid sequence which hybridizes with a nucleic acid sequence of any one of SEQ ID NOs: 9 to 16 and 36 under stringent conditions and is useful as a probe or primer for identifying, detecting, amplifying, etc. a nucleic acid sequence which catalyzes the synthesis of a dipeptide represented by formula (I).

(3) A recombinant nucleic acid sequence comprising the nucleic acid sequence according to the above (2).

(4) A transformant carrying the recombinant nucleic acid sequence according to the above (3).

(5) The transformant according to the above (4), wherein the transformant is a transformant obtained by using a microorganism as a host.

(6) The transformant according to the above (5), wherein the microorganism is a microorganism belonging to the genus Escherichia.

(7) A process for producing the protein according to the above (1), which comprises culturing the transformant according to any of the above (4) to (6) in a medium, allowing the protein according to the above (1) to form and accumulate in the culture medium, and recovering the protein from the culture medium.

(8) A process for producing the protein according to the above (1), which comprises culturing a microorganism having the ability to produce the protein according to the above (1) in a medium, allowing the protein to form and accumulate in the culture medium, and recovering the protein from the culture medium.

(9) The process according to the above (8), wherein the microorganism is a microorganism belonging to the genus *Bacillus*.

(10) The process according to the above (9), wherein the microorganism belonging to the genus *Bacillus* is a microorganism having the ability to produce bacilysin.

(11) The process according to the above (10), wherein the microorganism having the ability to produce bacilysin is a microorganism belonging to a species selected from the group consisting of *Bacillus subtilis, Bacillus amyloliquefaciens, Bacillus coagulans, Bacillus licheniformis, Bacillus megaterium* and *Bacillus pumilus*.

(12) A process for producing a dipeptide represented by formula (I):

$$R^1—R^2 \qquad (I)$$

(wherein $R^1$ and $R^2$, which may be the same or different, each represent an amino acid, provided that both $R^1$ and $R^2$ cannot represent L-alanine at the same time), which comprises:

allowing the protein according to the above (1) or a protein comprising the amino acid sequence shown in SEQ ID NO:1, at least two amino acids which may be the same or different, and ATP to be present in an aqueous medium;

allowing the dipeptide to form and accumulate in the medium; and recovering the dipeptide from the medium.

(13) A process for producing a dipeptide represented by formula (I):

$$R^1—R^2 \qquad (I)$$

(wherein $R^1$ and $R^2$, which may be the same or different, each represent an amino acid, provided that both $R^1$ and $R^2$ cannot represent L-alanine at the same time), which comprises:

allowing an enzyme source and at least two amino acids which may be the same or different to be present in an aqueous medium, said enzyme source being a culture or a treated matter of the culture selected from the group consisting of the following [1] to [3]:

[1] a culture of the transformant according to any of the above (4) to (6) or a treated matter of the culture;

[2] a culture of a microorganism having the ability to produce the protein according to the above (1) or a treated matter of the culture; and

[3] a culture of a microorganism having the ability to produce the protein comprising the amino acid sequence shown in SEQ ID NO:1 or a treated matter of the culture;

allowing the dipeptide to form and accumulate in the medium; and recovering the dipeptide from the medium.

(14) The process according to the above (13), wherein the microorganism having the ability to produce the protein according to the above (1) is a microorganism belonging to the genus *Bacillus* .

(15) The process according to the above (14), wherein the microorganism belonging to the genus *Bacillus* is a microorganism of the genus *Bacillus* having the ability to produce bacilysin.

(16) The process according to the above (15), wherein the microorganism of the genus *Bacillus* having the ability to produce bacilysin is a microorganism belonging to a species selected from the group consisting of *Bacillus subtilis, Bacillus amyloliquefaciens, Bacillus coagulans, Bacillus licheniformis, Bacillus megaterium* and *Bacillus pumilus*.

(17) The process according to the above (13), wherein the microorganism having the ability to produce the protein comprising the amino acid sequence shown in SEQ ID NO:1 is a microorganism transformed with a recombinant nucleic acid sequence comprising a nucleic acid sequence comprising the nucleotide sequence shown in SEQ ID NO: 9 or a microorganism belonging to *Bacillus subtilis*.

(18) The process according to the above (17), wherein the microorganism transformed with a recombinant nucleic acid sequence comprising a nucleic acid sequence comprising the nucleotide sequence shown in SEQ ID NO: 9 is a microorganism belonging to the genus Escherichia.

(19) The process according to any of the above (13) to (18), wherein the treated matter of the culture is a concentrated culture, a dried culture, cells obtained by centrifuging the culture, or a product obtained by subjecting the cells to drying, freeze-drying, treatment with a surfactant, ultrasonication, mechanical friction, treatment with a solvent, enzymatic treatment, protein fractionation or immobilization, or an enzyme preparation obtained by extracting the cells.

(20) The process according to any of the above (12) to (19), wherein the dipeptide is a dipeptide represented by formula (II):

$$R^3—R^4 \quad (II)$$

(wherein $R^3$ and $R^4$, which may be the same or different, each represent an amino acid selected from the group consisting of L-alanine, L-glutamine, L-glutamic acid, glycine, L-valine, L-leucine, L-isoleucine, L-proline, L-phenylalanine, L-tryptophan, L-methionine, L-serine, L-threonine, L-cysteine, L-asparagine, L-tyrosine, L-lysine, L-arginine, L-histidine, L-aspartic acid, L-α-aminobutyric acid, β-alanine, L-azaserine, L-theanine, L-4-hydroxyproline, L-3-hydroxyproline, L-ornithine, L-citrulline and L-6-diazo-5-oxo-norleucine, provided that both $R^3$ and $R^4$ cannot represent L-alanine at the same time).

In accordance with the present invention, a protein which catalyzes the synthesis of a dipeptide which is different from L-Ala-L-Ala and for which no enzymatic synthesis method has so far been proposed can be produced. Dipeptides other than L-Ala-L-Ala can be produced by using the protein, or a transformant or a microorganism having the ability to produce the protein.

Figure 1:
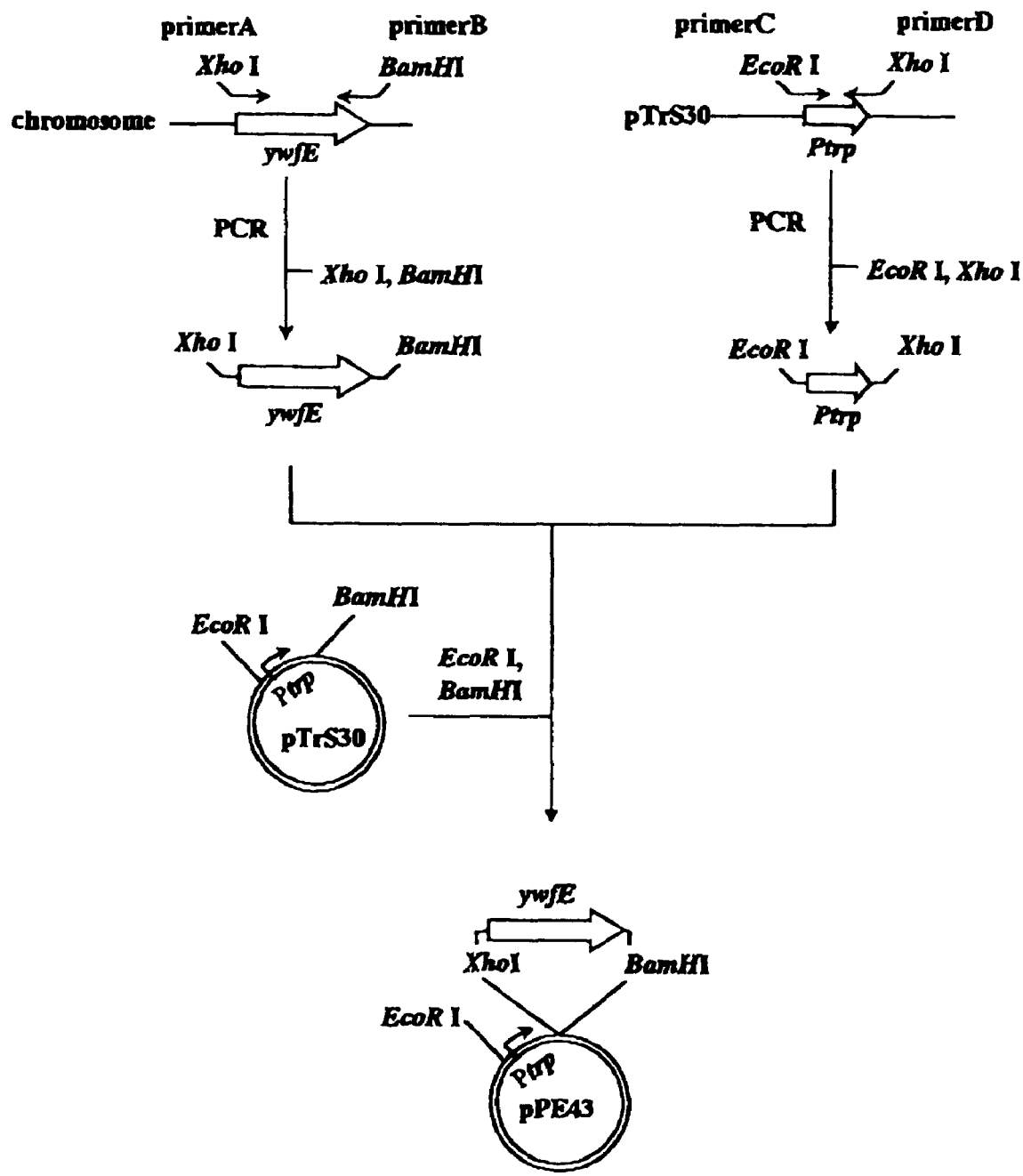
FIG. 1 shows the steps for constructing plasmid pPE43.

EXPLANATION OF SYMBOLS ywfE: ywfE gene derived from *Bacillus subtilis* 168
Ptrp: Tryptophan promoter gene
PT5: T5 promoter gene

DETAILED DESCRIPTION OF THE INVENTION

The proteins of the present invention include:
[1] a protein comprising the amino acid sequence shown in any of SEQ ID NOS: 2 to 8;
[2] a protein comprising an amino acid sequence wherein one or more amino acid residues are deleted, substituted or added in the amino acid sequence shown in any of SEQ ID NOS: 1 to 8 and catalyzing the synthesis of a dipeptide represented by formula (I)

$$R^1—R^2 \quad (I)$$

(wherein $R^1$ and $R^2$, which may be the same or different, each represent an amino acid, provided that both $R^1$ and $R^2$ cannot represent L-alanine at the same time)

[3] a protein comprising an amino acid sequence which shoes 65% or more similarity to the amino acid sequence shown in any of SEQ ID NOS: 1 to 8 and catalyzing the synthesis of a dipeptide represented by formula (I); and

[4] a protein comprising an amino acid sequence which shows 80% or more similarity to the amino acid sequence shown in SEQ ID NO: 17 and catalyzing the synthesis of a dipeptide represented by formula (I), provided that a protein consisting of the amino acid sequence shown in SEQ ID NO: 1 is excluded The proteins of the present invention are useful of the production of a dipeptide of formula (I), for example, as may be provided by the protein of SEQ ID NO: 1.

The use of the protein of SEQ ID NO: 1 in this manner forms a part of the present invention along with the further products and methods described herein.

Hereinafter, the above proteins of the present invention and proteins which catalyzes the synthesis of a dipeptide represented by formula (I) may be collectively referred to as the proteins of the present invention.

The above protein consisting of an amino acid sequence wherein one or more amino acid residues are deleted, substituted or added and catalyzing the synthesis of a dipeptide represented by formula (I) can be obtained, for example, by introducing a site-directed mutation into DNA encoding a protein consisting of the amino acid sequence shown in any of SEQ ID NOS: 1 to 8 by site-directed mutagenesis described in Molecular Cloning, A Laboratory Manual, Second Edition, Cold Spring Harbor Laboratory Press (1989) (hereinafter referred to as Molecular Cloning, Second Edition); Current Protocols in Molecular Biology, John Wiley & Sons (1987-1997) (hereinafter referred to as Current Protocols in Molecular Biology); Nucleic Acids Research, 10, 6487 (1982); Proc. Natl. Acad. Sci. USA, 79, 6409 (1982); Gene, 34, 315 (1985); Nucleic Acids Research, 13, 4431 (1985); Proc. Natl. Acad. Sci. USA, 82, 488 (1985), etc.

The number of amino acid residues which are deleted, substituted or added is not specifically limited, but is within the range where deletion, substitution or addition is possible by known methods such as the above site-directed mutagenesis. The suitable number is 1 to dozens, preferably 1 to 20, more preferably 1 to 10, further preferably 1 to 5.

The expression "one or more amino acid residues are deleted, substituted or added in the amino acid sequence shown in any of SEQ ID NOS: 1 to 8" means that the amino acid sequence may contain deletion, substitution or addition of a single or plural amino acid residues at an arbitrary position of the amino acid sequence shown in SEQ ID NO: 1 to 8.

Amino acid residues that may be substituted are, for example, those which are not conserved in all of the amino acid sequences shown in SEQ ID NOS: 1 to 8 when the sequences are compared using known alignment software. An example of known alignment software is alignment analysis software contained in gene analysis software Genetyx (Software Development Co., Ltd.). As analysis parameters for the analysis software, default values can be used.

Deletion or addition of amino acid residues may be contained, for example, in the N-terminal region or the C-terminal region of the amino acid sequence shown in any of SEQ ID NOS: 1 to 8.

Deletion, substitution and addition may be simultaneously contained in one sequence, and amino acids to be substituted or added may be either natural or not. Examples of the natural amino acids are L-alanine, L-asparagine, L-aspartic acid, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine and L-cysteine.

The following are examples of the amino acids capable of mutual substitution. The amino acids in the same group can be mutually substituted.

Group A: leucine, isoleucine, norleucine, valine, norvaline, alanine, 2-aminobutanoic acid, methionine, O-methylserine, t-butylglycine, t-butylalanine, cyclohexylalanine Group B: aspartic acid, glutamic acid, isoaspartic acid, isoglutamic acid, 2-aminoadipic acid, 2-aminosuberic acid Group C: asparagine, glutamine Group D: lysine, arginine, ornithine, 2,4-diaminobutanoic acid, 2,3-diaminopropionic acid Group E: proline, 3-hydroxyproline, 4-hydroxyproline Group F: serine, threonine, homoserine Group G: phenylalanine, tyrosine In order that the protein of the present invention may have the activity to synthesize a dipeptide represented by formula (I), it is desirable that the similarity of its amino acid sequence to the amino acid sequence shown in any of SEQ ID NOS: 1 to 8, preferably SEQ ID NO: 1, is 65% or more, preferably 75% or more, more preferably 85% or more, further preferably 90% or more, particularly preferably 95% or more, and most preferably 98% or more.

The similarity among amino acid sequences and nucleotide sequences can be determined by using algorithm BLAST by Karlin and Altschul [Proc. Natl. Acad. Sci. USA, 90, 5873 (1993)] and FASTA [Methods Enzymol., 183, 63 (1990)]. On the basis of the algorithm BLAST, programs such as BLASTN and BLASTX have been developed [J. Mol. Biol., 215, 403 (1990)]. When a nucleotide sequence is analyzed by BLASTN on the basis of BLAST, the parameters, for instance, are as follows: score=100 and wordlength=12. When an amino acid sequence is analyzed by BLASTX on the basis of BLAST, the parameters, for instance, are as follows: score=50 and wordlength=3. When BLAST and Gapped BLAST programs are used, default parameters of each program are used. The specific techniques for these analyses are known (see, the internet site: ncbi.nlm.nih.gov.).

A protein consisting of an amino acid sequence which shows 65% or more, preferably 75% or more, more preferably 85% or more, further preferably 90% or more, particularly preferably 95% or more, most preferably 98% or more similarity to the amino acid sequence shown in any of SEQ ID NOS: 1 to 8, preferably SEQ ID NO: 1, and catalying the synthesis of a dipeptide represented by formula (I) is also included in the proteins of the present invention (provided that a protein consisting of the amino acid sequence shown in SEQ ID NO: 1 is excluded). The similarity among amino acid sequences can be determined by using BLAST or FASTA as described above.

The amino acid sequence shown in SEQ ID NO: 17 is a region conserved among the proteins having the amino acid sequences shown in SEQ ID NOS: 1 to 7 and is also a region corresponding to the consensus sequence of proteins having Ala-Ala ligase activity derived from various microorganisms.

A protein comprising an amino acid sequence which shows 80% or more, preferably 90% or more, further preferably 95% or more similarity to the amino acid. sequence shown in SEQ ID NO: 17 and catalyzing the synthesis of a dipeptide represented by formula (I) is also included in the proteins of the present invention (provided that a protein consisting of the amino acid sequence shown in SEQ ID NO: 1 is excluded).

In order that the protein comprising an amino acid sequence which shows 80% or more, preferably 90% or more, further preferably 95% or more similarity to the amino acid sequence shown in SEQ ID NO: 17 may have the activity to synthesize a dipeptide represented by formula (I), it is desirable that the similarity of its amino acid sequence to the amino acid sequence shown in any of SEQ ID NOS: 1 to 8 is at least 80% or more, usually 90% or more, and particularly 95% or more.

The similarity among amino acid sequences can be determined by using BLAST or FASTA as described above.

It is possible to confirm that the protein of the present invention is a protein which catalyzes the synthesis of a dipeptide represented by the above formula (I), for example, in the following manner. That is, a transformant expressing the protein of the present invention is prepared by recombinant DNA techniques, the protein of the present invention is produced using the transformant, and then the protein of the present invention, at least two amino acids which may be the same or different (provided that L-alanine is used in combination with another L-amino acid) and ATP are allowed to be present in an aqueous medium, followed by HPLC analysis or the like to know whether a dipeptide represented by the above formula (I) is formed and accumulated in the aqueous medium.

The nucleic acid sequences of the present invention include:

[5] a nucleic acid sequence encoding the protein of the present invention according to any of the above [1] to [4];

[6] a nucleic acid sequence comprising the nucleotide sequence shown in any of SEQ ID NOS: 10 to 16 and 36;

[7] a nucleic acid sequence which hybridizes with a nucleic acid sequence comprising the complement of a nucleotide sequence shown in any of SEQ ID NOS: 9 to 16 and 36 under stringent conditions and which encodes a protein which catalyzes the synthesis of a dipeptide represented by formula (I), provided that DNA consisting of the nucleotide sequence shown in SEQ ID NO: 9 is excluded, preferably provided that DNA encoding the protein consisting of the amino acid sequence shown in SEQ ID NO: 1 is excluded; and

[8] a nucleic acid sequence comprising a nucleotide sequence which shows 80% or more similarity to the nucleotide sequence shown in SEQ ID NO: 18 and encoding a protein which catalyzes the synthesis of a dipeptide represented by formula (I), provided that DNA consisting of the nucleotide sequence shown in SEQ ID NO: 9 is excluded, preferably provided that DNA encoding the protein consisting of an amino acid sequence shown in SEQ ID NO: 1 is excluded.

The nucleic acid sequences that can be used in the process for producing a dipeptide represented by formula (I) of the present invention include the nucleic acid sequences according to the above [5] to [8] and a nucleic acid sequence comprising the nucleotide sequence shown in SEQ ID NO: 9.

The above nucleic acid sequence capable of hybridization under stringent conditions refers, for example, to a nucleic acid sequences which are obtained by colony hybridization, plaque hybridization, Southern blot hybridization, or the like using a part or the whole of a nucleic acid sequence comprising the nucleotide sequence shown in any of SEQ ID NOS: 9 to 16 and 36 as a probe. A specific example of such a nucleic acid sequence is a nucleic acid sequence which can be identified by performing hybridization at 65° C. in the presence of 0.7 to 1.0 mol/l sodium chloride using a filter with colony- or plaque-derived DNA immobilized thereon, and then washing the filter at 65° C. with a 0.1 to 2-fold conc. SSC solution (1-fold conc. SSC solution: 150 mmol/l sodium chloride and 15 mmol/l sodium citrate). Hybridization can be carried out according to the methods described in Molecular Cloning, Second Edition; Current Protocols in Molecular Biology; DNA Cloning 1: Core Techniques, A Practical Approach, Second Edition, Oxford University (1995), etc. Specifically, the hybridizable nucleic acid sequences includes DNA having at least 75% or more similarity, preferably 85% or more similarity, further preferably 90% or more similarity, particularly preferably 95% or more similarity to the nucleotide sequence shown in any of SEQ ID NOS: 9 to 16 and 36 as calculated by use of BLAST or FASTA described above based on the above parameters.

It is possible to confirm that the nucleic acid sequence which hybridizes with a nucleic acid sequence comprising the nucleotide sequence shown in any of SEQ ID NOS: 9 to 16 and 36 under stringent conditions is a nucleic acid sequence encoding a protein which catalyzes the synthesis of a dipeptide represented by formula (I), for example, by producing a protein encoded by the DNA by recombinant DNA techniques and measuring the activity of the protein as described above.

(i) Preparation of a DNA of the Present Invention and DNA Used in a Process for Producing the Protein or Dipeptide of the Present Invention A DNA of the present invention and a DNA used in the process for producing the protein or dipeptide of the present invention (hereinafter, also referred to as the production process of the present invention) can be obtained, for example, by Southern hybridization of a chromosomal DNA library from a microorganism belonging to the genus *Bacillus* using a probe designed based on the nucleotide sequence shown in any of SEQ ID NOS: 9 to 16 and 36, or by PCR [PCR Protocols, Academic Press (1990)] using primer DNAs designed based on the nucleotide sequence shown in any of SEQ ID NOS: 9 to 16 and 36 and, as a template, the chromosomal DNA of a microorganism belonging to the genus *Bacillus*.

A DNA of the present invention and a DNA used in the production process of the present invention can also be obtained by conducting a search through various gene sequence databases for a sequence showing 75% or more similarity, preferably 85% or more similarity, more preferably 90% or more similarity, further preferably 95% or more similarity, particularly preferably 98% or more similarity to the nucleotide sequence of DNA encoding the amino acid sequence shown in any of SEQ ID NOS: 1 to 8 and 17, and obtaining the desired DNA, based on the nucleotide sequence obtained by the search, from a chromosomal DNA or cDNA library of an organism having the nucleotide sequence according to the above-described method.

The obtained DNA, as such or after cleavage with appropriate restriction enzymes, is inserted into a vector by a conventional method, and the obtained recombinant DNA is introduced into a host cell. Then, the nucleotide sequence of the DNA can be determined by a conventional sequencing method such as the dideoxy method [Proc. Natl. Acad. Sci., USA, 74, 5463 (1977)] or by using a nucleotide sequencer such as 373A DNA Sequencer (Perkin-Elmer Corp.).

In cases where the obtained DNA is found to be a partial DNA by the analysis of nucleotide sequence, the full length DNA can be obtained by Southern hybridization of a chromosomal DNA library using the partial DNA as a probe.

It is also possible to prepare the desired DNA by chemical synthesis using a DNA synthesizer (e.g., Model 8905, Per-Septive Biosystems) based on the determined nucleotide sequence of the DNA.

Examples of the DNAs that can be obtained by the above-described method are DNAs having the nucleotide sequences shown in SEQ ID NOS: 9 to 16 and 36.

Examples of the vectors for inserting the DNA of the present invention or the DNA used in the production process of the present invention include pBluescriptII KS(+) (Stratagene), pDIRECT [Nucleic Acids Res., 18, 6069 (1990)], pCR-Script Amp SK(+) (Stratagene), pT7 Blue (Novagen, Inc.), pCR II (Invitrogen Corp.) and pCR-TRAP (Genhunter Corp.).

As the host cell, microorganisms belonging to the genus Escherichia, etc. can be used. Examples of the microorganisms belonging to the genus Escherichia include *Escherichia coli* XL1-Blue, *Escherichia coli* XL2-Blue, *Escherichia coli* DH1, *Escherichia coli* MC1000, *Escherichia coli* ATCC 12435, *Escherichia coli* W1485, *Escherichia coli* JM109, *Escherichia coli* HB101, *Escherichia coli* No. 49, *Escherichia coli* W3110, *Escherichia coli* NY49, *Escherichia coli* MP347, *Escherichia coli* NM522 and *Escherichia coli* ME8415.

Introduction of the recombinant DNA can be carried out by any of the methods for introducing DNA into the above host cells, for example, the method using calcium ion [Proc. Natl. Acad. Sci. USA, 69, 2110 (1972)], the protoplast method (Japanese Published Unexamined Patent Application No. 248394/88) and electroporation [Nucleic Acids Res., 16, 6127 (1988)].

An example of the microorganism carrying the DNA used in the production process of the present invention obtained by the above method is *Escherichia coli* NM522/pPE43, which is a microorganism transformed with a recombinant DNA comprising DNA having the sequence shown in SEQ ID NO: 1.

(ii) Process for Producing a Protein of the Present Invention

A protein of the present invention can be produced by expressing a DNA of the present invention or a DNA used in the production process of the present invention obtained by the methods described in the above (i) in host cells using the methods described in Molecular cloning, Second Edition, Current Protocols in Molecular Biology, etc., for example, in the following manner.

On the basis of a DNA of the present invention or a DNA used in the production process of the present invention, a nucleic acid sequence, such as a DNA, fragment of an appropriate length comprising a region encoding a protein of the present invention is prepared according to need. The productivity of the protein can be enhanced by replacing a nucleotide in the nucleotide sequence of the region encoding the protein so as to make a codon most suitable for the expression in a host cell. Codon optimized nucleic acid sequences therefore will be recognized as being a part of the presently disclosed invention.

The DNA fragment may be inserted downstream of a promoter in an appropriate expression vector to prepare a recombinant DNA.

A transformant producing a protein of the present invention can be obtained by introducing the recombinant DNA into a host cell suited for the expression vector.

As a host cell, any bacterial cells, yeast cells, animal cells, insect cells, plant cells, etc. that are capable of expressing the desired nucleic acid squence can be used.

The expression vectors that can be employed are those capable of autonomous replication or integration into the chromosome in the above host cells and comprising, for example, a promoter at a position appropriate for the transcription of a DNA of the present invention or a DNA used in the production process of the present invention.

When a procaryote such as a bacterium is used as the host cell, it is preferred that a recombinant DNA comprising a DNA of the present invention or a DNA used in the production process of the present invention is a recombinant DNA which is capable of autonomous replication in the procaryote and which comprises, for example, a promoter, a ribosome binding sequence, a DNA of the present invention or a DNA used in the production process of the present invention, and a transcription termination sequence. The recombinant DNA may further comprise a gene or nucleic acid sequence regulating the promoter.

Examples of suitable expression vectors are pBTrp2, pBTac1 and pBTac2 (products of Boehringer Mannheim GmbH), pHelix1 (Roche Diagnostics Corp.), pKK233-2 (Amersham Pharmacia Biotech), pSE280 (Invitrogen Corp.), pGEMEX-1 (Promega Corp.), pQE-8 (Qiagen, Inc.), pET-3 (Novagen, Inc.), pKYP10 (Japanese Published Unexamined Patent Application No. 110600/83), pKYP200 [Agric. Biol. Chem., 48, 669 (1984)], pLSA1 [Agric. Biol. Chem., 53, 277 (1989)], pGEL1 [Proc. Natl. Acad. Sci. USA, 92, 4306 (1985)], pBluescript II SK(+), pBluescript II KS(-) (Stratagene), pTrs30 [prepared from *Escherichia coli*JM109/pTrS30 (FERM BP-5407)], pTrs32 [prepared from *Escherichia coli* JM109/pTrS32 (FERM BP-5408)], pPAC31 (WO98/12343), pUC19 [Gene, 33, 103 (1985)], pSTV28 (Takara Shuzo Co., Ltd.), pUC118 (Takara Shuzo Co., Ltd.) and pPA1 (Japanese Published Unexamined Patent Application No. 233798/88).

As the promoter, any promoters capable of functioning in host cells such as *Escherichia coli* can be used. For example, promoters derived from *Escherichia coli* or phage, such as trp promoter ($P_{trp}$), lac promoter ($P_{lac}$), $P_L$ promoter, $P_R$ promoter and $P_{SE}$ promoter, SPO1 promoter, SPO2 promoter and penP promoter can be used. Artificially designed and modified promoters such as a promoter in which two $P_{trp}$s are combined in tandem, tac promoter, lacT7 promoter and letI promoter, etc. can also be used.

Also useful are xylA promoter for the expression in microorganisms belonging to the genus *Bacillus* [Appl. Microbiol. Biotechnol., 35, 594-599 (1991)] and P54-6 promoter for the expression in microorganisms belonging to the genus Corynebacterium [Appl. Microbiol. Biotechnol., 53, 674-679 (2000)].

It is preferred to use a plasmid in which the distance between the Shine-Dalgarno sequence (ribosome binding sequence) and the initiation codon is adjusted to an appropriate length (e.g., 6 to 18 nucleotides).

In the recombinant DNA wherein the DNA of the present invention or the DNA used in the production process of the present invention is ligated to an expression vector, the transcription termination sequence is not essential, but it is preferred to place the transcription termination sequence immediately downstream of the structural gene.

An example of such recombinant DNA is pPE43.

Examples of suitable procaryotes include microorganisms belonging to the genera *Escherichia, Serratia, Bacillus, Brevibacterium, Corynebacterium, Microbacterium, Pseudomonas, Agrobacterium, Alicyclobacillus, Anabaena, Anacystis, Arthrobacter, Azotobacter, Chromatium, Erwinia, Methylobacterium, Phormidium, Rhodobacter, Rhodopseudomonas, Rhodospirillum, Scenedesmus, Streptomyces, Synechoccus* and *Zymomonas*. Specific examples are *Escherichia coli* XL1-Blue, *Escherichia coli* XL2-Blue, *Escherichia coli* DH1, *Escherichia coli* DH5α, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* MP347, *Escherichia coli* NM522, *Bacillus subtilis* ATCC 33712, *Bacillus megaterium*, *Bacillus* sp. FERM BP-6030, *Bacillus amyloliguefaciens*, *Bacillus coagulans, Bacillus licheniformis, Bacillus pumilus, Brevibacterium ammoniagenes, Brevibacterium immariophilum* ATCC 14068, *Brevibacterium saccharolyticum* ATCC 14066, *Brevibacterium flavum* ATCC 14067, *Brevibacterium lactofermentum* ATCC 13869, *Corynebacterium glutamicum* ATCC 13032, *Corynebacterium glutamicum* ATCC 14297, *Corynebacterium acetoacidophilum* ATCC 13870, *Microbacterium ammoniaphilum* ATCC 15354, *Serratia ficaria, Serratia fonticola, Serratia liquefaciens, Serratia marcescens*, *Pseudomonas* sp D-0110, *Agrobacterium radiobacter, Agrobacterium rhizogenes, Agrobacterium rubi, Anabaena cylindrica, Anabaena doliolum, Anabaena flosaquae, Arthrobacter aurescens, Arthrobacter citreus, Arthrobacter globformis, Arthrobacter hydrocarboglutamicus, Arthrobacter mysorens, Arthrobacter nicotianae, Arthrobacter paraffineus, Arthrobacter protophormiae, Arthrobacter roseoparaffinus, Arthrobacter sulfureus, Arthrobacter ureafaciens, Chromatium buderi, Chromatium tepidum, Chromatium vinosum, Chromatium warmingii, Chromatium fluviatile, Erwinia uredovora, Erwinia carotovora, Erwinia ananas, Erwinia herbicola, Erwinia punctata, Erwinia terreus, Methylobacterium rhodesianum, Methylobacterium extorquens*, *Phormidium* sp. ATCC 29409, *Rhodobacter capsulatus, Rhodobacter sphaeroides, Rhodopseudomonas blastica, Rhodopseudomonas marina, Rhodopseudomonas palustris, Rhodospirillum rubrum, Rhodospirillum salexigens, Rhodospirillum salinarum, Streptomyces ambofaciens, Streptomyces aureofaciens, Streptomyces aureus, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus* and *Zymomonas mobilis*.

Introduction of the recombinant DNA can be carried out by any of the methods for introducing DNA into the above host cells, for example, the method using calcium ion [Proc. Natl. Acad. Sci. USA, 69, 2110 (1972)], the protoplast method (Japanese Published Unexamined Patent Application No. 248394/88) and electroporation [Nucleic Acids Res., 16, 6127 (1988)].

When a yeast strain is used as the host cell, YEp13 (ATCC 37115), YEp24 (ATCC 37051), YCp50 (ATCC 37419), pHS19, pHS15, etc. can be used as the expression vector.

As the promoter, any promoters capable of functioning in yeast strains can be used. Suitable promoters include PHO5 promoter, PGK promoter, GAP promoter, ADH promoter, gal 1 promoter, gal 10 promoter, heat shock polypeptide promoter, MFα1 promoter and CUP 1 promoter.

Examples of suitable host cells are yeast strains belonging to the genera Saccharomyces, Schizosaccharomyces, Kluyveromyces, Trichosporon, Schwanniomyces, Pichia and Candida, specifically, *Saccharomyces cerevisiae, Schizosaccharomyces pombe, Kluyveromyces lactis, Trichosporon pullulans, Schwanniomyces alluvius, Pichia pastoris* and *Candida utilis*.

Introduction of the recombinant DNA can be carried out by any of the methods for introducing DNA into yeast, for example, electroporation [Methods Enzymol., 194, 182

(1990)], the spheroplast method [Proc. Natl. Acad. Sci. USA, 81, 4889 (1984)] and the lithium acetate method [J. Bacteriol., 153, 163 (1983)].

When an animal cell is used as the host cell, pcDNAI, pcDM8 (commercially available from Funakoshi Co., Ltd.), pAGE107 (Japanese Published Unexamined Patent Application No. 22979/91), pAS3-3 (Japanese Published Unexamined Patent Application No. 227075/90), pCDM8 [Nature, 329, 840 (1987)], pcDNAI/Amp (Invitrogen Corp.), pREP4 (Invitrogen Corp.), pAGE103 [J. Biochem., 101, 1307 (1987)], pAGE210, pAMo, pAMoA, etc. can be used as the expression vector.

As the promoter, any promoters capable of functioning in animal cells can be used. Suitable promoters include the promoter of IE (immediate early) gene of cytomegalovirus (CMV), SV40 early promoter, metallothionein promoter, the promoter of a retrovirus, heat shock promoter, SRα promoter, etc. The enhancer of IE gene of human CMV may be used in combination with the promoter.

Examples of suitable host cells are mouse myeloma cells, rat myeloma cells, mouse hybridomas, human-derived Namalwa cells and Namalwa KJM-1 cells, human embryonic kidney cells, human leukemia cells, African green monkey kidney cells, Chinese hamster-derived CHO cells, and HBT5637 (Japanese Published Unexamined Patent Application No. 299/88).

The mouse myeloma cells include SP2/0 and NS0; the rat myeloma cells include YB2/0; the human embryonic kidney cells include HEX293 (ATCC CRL-1573); the human leukemia cells include BALL-1; and the African green monkey kidney cells include COS-1 and COS-7.

Introduction of the recombinant DNA can be carried out by any of the methods for introducing DNA into animal cells, for example, electroporation [Cytotechnology, 3, 133 (1990)], the calcium phosphate method (Japanese Published Unexamined Patent Application No. 227075/90), lipofection [Proc. Natl. Acad. Sci. USA, 84, 7413 (1987)], and the method described in Virology, 52, 456 (1973).

When an insect cell is used as the host cell, the protein can be produced by using the methods described in Baculovirus Expression vectors, A Laboratory Manual, W. H. Freeman and Company, New York (1992); Current Protocols in Molecular Biology; Molecular Biology, A Laboratory Manual; Bio/Technology, 6, 47 (1988), etc.

That is, the recombinant gene transfer vector and a baculovirus are cotransfected into insect cells to obtain a recombinant virus in the culture supernatant of the insect cells, and then insect cells are infected with the recombinant virus, whereby the protein can be produced.

The gene transfer vectors useful in this method include pVL1392, pVL1393 and pBlueBacIII (products of Invitrogen Corp.).

An example of the baculovirus is Autographa californica nuclear polyhedrosis virus, which is a virus infecting insects belonging to the family Barathra.

Examples of the insect cells are ovarian cells of *Spodoptera frugiperda*, ovarian cells of *Trichoplusia ni,* and cultured cells derived from silkworm ovary.

The ovarian cells of *Spodoptera frugiperda* include Sf9 and Sf21 (Baculovirus Expression Vectors, A Laboratory Manual); the ovarian cells of *Trichoplusia ni* include High 5 and BTI-TN-5B1-4 (Invitrogen Corp.); and the cultured cells derived from silkworm ovary include *Bombyx mori* N4.

Cotransfection of the above recombinant gene transfer vector and the above baculovirus into insect cells for the preparation of the recombinant virus can be carried out by the calcium phosphate method (Japanese Published Unexamined Patent Application No. 227075/90), lipofection [Proc. Natl. Acad. Sci. USA, 84, 7413 (1987)], etc.

When a plant cell is used as the host cell, Ti plasmid, tobacco mosaic virus vector, etc. can be used as the expression vector.

As the promoter, any promoters capable of functioning in plant cells can be used. Suitable promoters include 35S promoter of cauliflower mosaic virus (CaMV), rice actin 1 promoter, etc.

Examples of suitable host cells are cells of plants such as tobacco, potato, tomato, carrot, soybean, rape, alfalfa, rice, wheat and barley.

Introduction of the recombinant vector can be carried out by any of the methods for introducing DNA into plant cells, for example, the method using Agrobacterium (Japanese Published Unexamined Patent Application Nos. 140885/84 and 70080/85, WO94/00977), electroporation (Japanese Published Unexamined Patent Application No. 251887/85) and the method using particle gun (gene gun) (Japanese Patent Nos. 2606856 and 2517813).

When the DNA is expressed in yeast, an animal cell, an insect cell or a plant cell, a glycosylated protein can be obtained.

The protein of the present invention can be produced by culturing the transformant obtained as above in a medium, allowing a protein of the present invention to form and accumulate in the culture, and recovering the protein from the culture.

The host of the above transformant for producing the protein of the present invention may be any bacterium, yeast, animal cell, insect cell, plant cell or the like, but is preferably a bacterium, more preferably a microorganism belonging to the genus Escherichia, and further preferably a microorganism belonging to *Escherichia coli.*

Culturing of the above transformant in a medium can be carried out by conventional methods for culturing the host.

For the culturing of the transformant obtained by using a procaryote such as *Escherichia coli* or a eucaryote such as yeast as the host, any of natural media and synthetic media can be used insofar as it is a medium suitable for efficient culturing of the transformant which contains carbon sources, nitrogen sources, inorganic salts, etc. which can be assimilated by the host used.

As the carbon sources, any carbon sources that can be assimilated by the host can be used. Examples of suitable carbon sources include carbohydrates such as glucose, fructose, sucrose, molasses containing them, starch and starch hydrolyzate; organic acids such as acetic acid and propionic acid; and alcohols such as ethanol and propanol.

As the nitrogen sources, ammonia, ammonium salts of organic or inorganic acids such as ammonium chloride, ammonium sulfate, ammonium acetate and ammonium phosphate, and other nitrogen-containing compounds can be used as well as peptone, meat extract, yeast extract, corn steep liquor, casein hydrolyzate, soybean cake, soybean cake hydrolyzate, and various fermented microbial cells and digested products thereof.

Examples of the inorganic salts include potassium dihydrogenphosphate, dipotassium hydrogenphosphate, magnesium phosphate, magnesium sulfate, sodium chloride, ferrous sulfate, manganese sulfate, copper sulfate and calcium carbonate.

Culturing is usually carried out under aerobic conditions, for example, by shaking culture or submerged spinner culture under aeration. The culturing temperature is preferably 15 to 40° C., and the culturing period is usually 5 hours to 7 days. The pH is maintained at 3.0 to 9.0 during the culturing. The pH adjustment is carried out by using an organic or inorganic acid, an alkali solution, urea, calcium carbonate, ammonia, etc.

If necessary, antibiotics such as ampicillin and tetracycline may be added to the medium during the culturing.

When a microorganism transformed with an expression vector comprising an inducible promoter is cultured, an inducer may be added to the medium, if necessary. For example, in the case of a microorganism transformed with an expression vector comprising lac promoter, isopropyl-β-D-thiogalactopyranoside or the like may be added to the medium; and in the case of a microorganism transformed with an expression vector comprising trp promoter, indoleacrylic acid or the like may be added.

For the culturing of the transformant obtained by using an animal cell as the host cell, generally employed media such as RPMI1640 medium [J. Am. Med. Assoc., 199, 519 (1967)], Eagle's MEM [Science, 122, 501 (1952)], DMEM [Virology, 8, 396 (1959)] and 199 medium [Proc. Soc. Biol. Med., 73, 1 (1950)], media prepared by adding fetal calf serum or the like to these media, etc. can be used as the medium.

Culturing is usually carried out at pH 6 to 8 at 25 to 40° C. for 1 to 7 days in the presence of 5% $CO_2$.

If necessary, antibiotics such as kanamycin, penicillin and streptomycin may be added to the medium during the culturing.

For the culturing of the transformant obtained by using an insect cell as the host cell, generally employed media such as TNM-FH medium (PharMingen, Inc.), Sf-900 II SFM medium (Life Technologies, Inc.), ExCell 400 and ExCell 405 (JRH Biosciences, Inc.) and Grace's Insect Medium [Nature, 195, 788 (1962)] can be used as the medium.

Culturing is usually carried out at pH 6 to 7 at 25 to 30° C. for 1 to 5 days.

If necessary, antibiotics such as gentamicin may be added to the medium during the culturing.

The transformant obtained by using a plant cell as the host cell may be cultured in the form of cells as such or after differentiation into plant cells or plant organs. For the culturing of such transformant, generally employed media such as Murashige-Skoog (MS) medium and White medium, media prepared by adding phytohormones such as auxin and cytokinin to these media, etc. can be used as the medium.

Culturing is usually carried out at pH 5 to 9 at 20 to 40° C. for 3 to 60 days.

If necessary, antibiotics such as kanamycin and hygromycin may be added to the medium during the culturing.

As described above, a protein of the present invention can be produced by culturing, according to a conventional culturing method, the transformant derived from a microorganism, an insect cell, an animal cell or a plant cell and carrying a recombinant DNA prepared by ligating a DNA of the present invention or a DNA used in the production process of the present invention to an expression vector, allowing the protein to form and accumulate, and recovering the protein from the culture.

A protein of the present invention may be produced by intracellular production by host cells, extracellular secretion by host cells or production on outer membranes by host cells, and depending on the method selected, the structure of the protein produced is suitably modified.

When a protein of the present invention is produced in host cells or on outer membranes of host cells, it is possible to force the protein to be secreted outside the host cells by applying the method of Paulson, et al. [J. Biol. Chem., 264, 17619 (1989)], the method of Lowe, et al. [Proc. Natl. Acad. Sci. USA, 86, 8227 (1989); Genes Develop., 4, 1288 (1990)], or the methods described in Japanese Published Unexamined Patent Application No. 336963/93, WO94/23021, etc.

That is, extracellular secretion of a protein of the present invention by host cells can be caused by producing it in the form of a protein in which a signal peptide is added upstream of a protein containing the active site of the protein of a present invention by the use of recombinant DNA techniques.

It is also possible to increase the protein production by utilizing a gene amplification system using a dihydrofolate reductase gene or the like according to the method described in Japanese Published unexamined Patent Application No. 227075/90.

Further, a protein of the present invention can be produced using an animal having an introduced gene (non-human transgenic animal) or a plant having an introduced gene (transgenic plant) constructed by redifferentiation of animal or plant cells carrying the introduced gene or nucleic acid sequence.

When a transformant producing a protein of the present invention is an animal or plant, the protein can be produced by raising or culturing the animal or plant in a usual manner, allowing the protein to form and accumulate therein, and recovering the protein from the animal or plant.

Production of a protein of the present invention using an animal can be carried out, for example, by producing the protein in an animal constructed by introducing the gene according to known methods [Am. J. Clin. Nutr., 63, 639S (1996); Am. J. Clin. Nutr., 63, 627S (1996); Bio/Technology, 9, 830 (1991)].

In the case of an animal, a protein of the present invention can be produced, for example, by raising a non-human transgenic animal carrying an introduced DNA of the present invention or DNA used in the production process of the present invention, allowing the protein to form and accumulate in the animal, and recovering the protein from the animal. The places where the protein is formed and accumulated include milk (Japanese Published Unexamined Patent Application No. 309192/88), egg, etc. of the animal. As the promoter in this process, any promoters capable of functioning in an animal can be used. Preferred promoters include mammary gland cell-specific promoters such as α casein promoter, β casein promoter, β lactoglobulin promoter and whey acidic protein promoter.

Production of the protein of the present invention using a plant can be carried out, for example, by culturing a transgenic plant carrying the introduced DNA encoding the protein of the present invention according to known methods [Soshiki Baiyo (Tissue Culture), 20 (1994); Soshiki Baiyo, 21 (1995); Trends Biotechnol., 15, 45 (1997)], allowing the protein to form and accumulate in the plant, and recovering the protein from the plant. Tissue specific promoters may also be used in plant production by means known to one of ordinary skill.

Isolation and purification of a protein of the present invention produced using the transformant producing a protein of the present invention can be carried out by conventional methods for isolating and purifying enzymes.

For example, when a protein of the present invention is produced in a soluble form in cells, the cells may be recovered by centrifugation after the completion of culturing and suspended in an aqueous buffer, followed by disruption using a sonicator, French press, Manton Gaulin homogenizer, Dynomill or the like to obtain a cell-free extract.

A purified protein preparation can be obtained by centrifuging the cell-free extract to obtain the supernatant and then subjecting the supernatant to ordinary means for isolating and purifying enzymes, e.g., extraction with a solvent, salting-out with ammonium sulfate, etc., desalting, precipitation with an organic solvent, anion exchange chromatography using resins such as diethylaminoethyl (DEAE)-Sepharose and DIAION HPA-75 (Mitsubishi Chemical Corporation), cation exchange chromatography using resins such as S-Sepharose FF (Pharmacia), hydrophobic chromatography using resins such as butyl Sepharose and phenyl Sepharose, gel filtration using a molecular sieve, affinity chromatography, chromatofocusing, and electrophoresis such as isoelectric focusing, alone or in combination.

When the protein is produced as an inclusion body in cells, the cells are similarly recovered and disrupted, followed by centrifugation to obtain a precipitate fraction. After the protein is recovered from the precipitate fraction by an ordinary method, the inclusion body of the protein is solubilized with a protein-denaturing agent.

The solubilized protein solution is diluted with or dialyzed against a solution containing no protein-denaturing agent or a solution containing the protein-denaturing agent at such a low concentration that denaturation of protein is not caused, whereby the protein is renatured to have normal higher-order structure. Then, a purified protein preparation can be obtained by the same isolation and purification steps as described above.

When a protein of the present invention or its derivative such as a glycosylated form is extracellularly secreted, the protein or its derivative such as a glycosylated form can be recovered in the culture supernatant.

That is, the culture is treated by the same means as above, e.g., centrifugation, to obtain a soluble fraction. A purified protein preparation can be obtained from the soluble fraction by using the same isolation and purification methods as described above.

Examples of the proteins obtained in the above manner are proteins respectively consisting of the amino acid sequences shown in SEQ ID NOS: 1 to 8.

It is also possible to produce a protein of the present invention as a fusion protein with another protein and to purify it by affinity chromatography using a substance having affinity for the fused protein. For example, according to the method of Lowe, et al. [Proc. Natl. Acad. Sci. USA, 86, 8227 (1989); Genes Develop., 4, 1288 (1990)] and the methods described in Japanese Published Unexamined Patent Application No. 336963/93 and WO94/23021, a protein of the present invention can be produced as a fusion protein with protein A and can be purified by affinity chromatography using immunoglobulin G.

Further, it is possible to produce a protein of the present invention as a fusion protein with a Flag peptide and to purify it by affinity chromatography using anti-Flag antibody [Proc. Natl. Acad. Sci. USA, 86, 8227 (1989); Genes Develop., 4, 1288 (1990)]. The protein can also be purified by affinity chromatography using an antibody against said protein.

A protein of the present invention can also be produced by chemical synthetic methods such as the Fmoc method (the fluorenylmethyloxycarbonyl method) and the tBoc method (the t-butyloxycarbonyl method) based on the amino acid sequence information on the protein obtained above. Further, a protein of the present invention can be chemically synthesized by using peptide synthesizers from Advanced ChemTech, Perkin-Elmer, Pharmacia, Protein Technology Instrument, Synthecell-Vega, PerSeptive, Shimadzu Corporation, etc.

(iii) Process for Producing a Dipeptide of the Present Invention (1) Enzymatic Process An example of the enzymatic process for producing a dipeptide is a process which comprises: allowing a protein of the present invention, at least two amino acids which may be the same or different, and ATP to be present in an aqueous medium; allowing a dipeptide represented by formula (I) to form and accumulate in the medium; and recovering the dipeptide from the medium.

At least two amino acids, preferably one or two kinds of amino acids used as substrates in the above process are selected from the group consisting of amino acids, preferably L-amino acids, glycine (Gly) and β-alanine (β-Ala), and can be used in any combination except for the use of L-alanine as one kind of amino acid. Examples of L-amino acids are L-alanine (L-Ala), L-glutamine (L-Gln), L-glutamic acid (L-Glu), L-valine (L-Val), L-leucine (L-Leu), L-isoleucine (L-Ile), L-proline (L-Pro), L-phenylalanine (L-Phe), L-tryptophan (L-Trp), L-methionine (L-Met), L-serine (L-Ser), L-threonine (L-Thr), L-cysteine (L-Cys), L-asparagine (L-Asn), L-tyrosine (L-Tyr), L-lysine (L-Lys), L-arginine (L-Arg), L-histidine (L-His), L-aspartic acid (L-Asp), L-α-aminobutyric acid (L-α-AB), L-azaserine, L-theanine, L-4-hydroxyproline (L-4-HYP), L-3-hydroxyproline (L-3-HYP), L-ornithine (L-Orn), L-citrulline (L-Cit) and L-6-diazo-5-oxo-norleucine.

The amino acids which are more preferably used in the above process include the following: a combination of one kind of amino acid selected from the group consisting of L-Ala, Gly, L-Met, L-Ser, L-Thr and β-Ala, and one kind of amino acid selected from the group consisting of L-Ala, L-Gln, L-Glu, Gly, L-Val, L-Leu, L-Ile, L-Pro, L-Phe, L-Trp, L-Met, L-Ser, L-Thr, L-Cys, L-Asn, L-Tyr, L-Lys, L-Arg, L-His, L-Asp, L-α-AB, O-Ala, L-azaserine, L-theanine, L-4-HYP, L-3-HYP, L-Orn, L-Cit and L-6-diazo-5-oxo-norleucine (excluding a combination of L-Ala and L-Ala); a combination of L-Gln and L-Phe; and a combination of L-α-AB and L-Gln, L-Arg or L-α-AB. Further preferred amino acids are: a combination of L-Ala and one kind of amino acid selected from the group consisting of L-Gln, Gly, L-Val, L-Leu, L-Ile, L-Phe, L-Trp, L-Met, L-Ser, L-Thr, L-Cys, L-Asn, L-Tyr, L-Lys, L-Arg, L-His, L-α-AB, L-azaserine, L-Cit and L-theanine; a combination of Gly and one kind of amino acid selected from the group consisting of L-Gln, Gly, L-Phe, L-Trp, L-Met, L-Ser, L-Thr, L-Cys, L-Tyr, L-Lys, L-Arg, L-α-AB and L-Cit; a combination of L-Met and one kind of amino acid selected from the group consisting of L-Phe, L-Met, L-Ser, L-Thr, L-Cys, L-Tyr, L-Lys and L-His; a combination of L-Ser and one kind of amino acid selected from the group consisting of L-Gln, L-Phe, L-Ser, L-Thr, L-Tyr, L-His and L-α-AB; a combination of L-Thr and one kind of amino acid selected from the group consisting of L-Gln, L-Phe, L-Leu, L-Thr and L-α-AB; a combination of L-Gln and L-Phe; a combination of β-Ala and one kind of amino acid selected from the group consisting of L-Phe, L-Met, L-His and L-Cit; and a combination of L-a-AB and L-Gln, L-Arg or L-α-AB.

In the above process, a protein of the present invention is added in an amount of 0.01 to 100 mg, preferably 0.1 to 10 mg per mg of amino acid used as a substrate.

In the above process, the amino acid used as a substrate is added to the aqueous medium at the start or in the course of reaction to give a concentration of 0.1 to 500 g/l, preferably 0.2 to 200 g/l.

In the above process, ATP used as an energy source is used at a final concentration of 0.5 mmol to 10 mol/l.

The aqueous medium used in the above process may comprise any components and may have any composition so far as the dipeptide-forming reaction is not inhibited. Suitable aqueous media include water and buffers such as phosphate buffer, carbonate buffer, acetate buffer, borate buffer, citrate buffer and Tris buffer. The aqueous medium may comprise alcohols such as methanol and ethanol, esters such as ethyl acetate, ketones such as acetone, and amides such as acetamide.

The dipeptide-forming reaction is carried out in the aqueous medium at pH 5 to 11, preferably pH 6 to 10, at 20 to 50° C., preferably 25 to 45° C., for 2 to 150 hours, preferably 6 to 120 hours.

The dipeptides produced by the above process include the dipeptides represented by formula (I). Preferred dipeptides are those represented by formula (I) wherein $R^1$ and $R^2$, which may be the same or different, each represent an amino acid selected from the group consisting of L-Ala, L-Gln, L-Glu, Gly, L-Val, L-Leu, L-Ile, L-Pro, L-Phe, L-Trp, L-Met, L-Ser, L-Thr, L-Cys, L-Asn, L-Tyr, L-Lys, L-Arg, L-His, L-Asp, L-α-AB, β-Ala, L-azaserine, L-theanine, L-4-HYP, L-3-HYP, L-Orn, L-Cit and L-6-diazo-5-oxo-norleucine (excluding that wherein both $R^1$ and $R^2$ are L-Ala at the same time). More preferred are dipeptides wherein $R^1$ is L-Ala, Gly, L-Met, L-Ser, L-Thr or β-Ala, and $R^2$ is L-Gln, L-Glu, Gly, L-Val, L-Leu, L-Ile, L-Pro, L-Phe, L-Trp, L-Met, L-Ser, L-Thr, L-Cys, L-Asn, L-Tyr, L-Lys, L-Arg, L-His, L-Asp, L-α-AB, β-Ala, L-azaserine, L-theanine, L-4-HYP, L-3-HYP, L-Orn, L-Cit or L-6-diazo-5-oxo-norleucine. Further preferred dipeptides are: dipeptides wherein $R^1$ is L-Ala and $R^2$ is L-Gln, Gly, L-Val, L-Leu, L-Ile, L-Phe, L-Trp, L-Met, L-Ser, L-Thr, L-Cys, L-Asn, L-Tyr, L-Lys, L-Arg, L-His, L-α-AB, L-azaserine, L-theanine or L-Cit; dipeptides wherein $R^1$ is Gly and $R^2$ is L-Gln, Gly, L-Phe, L-Trp, L-Met, L-Ser, L-Thr, L-Cys, L-Tyr, L-Lys, L-Arg, L-α-AB or L-Cit; dipeptides wherein $R^1$ is L-Met and $R^2$ is L-Phe, L-Met, L-Cys, L-Tyr, L-Lys or L-His; dipeptides wherein $R^1$ is L-Ser and $R^2$ is L-Gln, Gly, L-Phe, L-Met, L-Ser, L-Thr, L-Tyr, L-His or L-α-AB; dipeptides wherein $R^1$ is L-Thr and $R^2$ is L-Gln, L-Leu, L-Phe, L-Met, L-Ser, L-Thr or L-α-AB; dipeptides wherein $R^1$ is L-Gln and $R^2$ is L-Phe or L-α-AB; a dipeptide wherein $R^1$ is L-Phe and $R^2$ is L-Gln; a dipeptide wherein $R^1$ is L-Trp and $R^2$ is Gly; dipeptides wherein $R^1$ is L-Cys and $R^2$ is L-Ala, L-Gln, Gly or L-Met; dipeptides wherein $R^1$ is L-Lys and $R^2$ is L-Ala, Gly or L-Met; dipeptides wherein $R^1$ is β-Ala and $R^2$ is L-Phe, L-Met or L-His; a dipeptide wherein $R^1$ is L-Arg and $R^2$ is L-α-AB; a dipeptide wherein $R^1$ is L-His and $R^2$ is L-Met; and dipeptides wherein $R^1$ is L-α-AB and $R^2$ is L-Ala, L-Gln, Gly, L-Ser, L-Thr, L-Arg or L-α-AB.

(2) Process using a Culture of a Transformant or Microorganism or a Treated Matter of the Culture as an Enzyme Source An example of the process for producing a dipeptide using a culture of a transformant or microorganism or a treated matter of the culture as an enzyme source is a process which comprises: allowing an enzyme source and at least two amino acids which may be same or different to be present in an aqueous medium, said enzyme source being a culture of a transformant having the ability to produce a protein of the present invention or a microorganism having the ability to produce a protein of the present invention, or a treated matter of the culture; allowing a dipeptide represented by formula (I) to form and accumulate in the medium; and recovering the dipeptide from the medium.

Transformants useful in the above process include the transformants producing a protein of the present invention that can be produced by the method of the above (ii). As the hosts of the transformants, bacteria, yeast, animal cells, insect cells, plant cells, etc. can be used. Preferred hosts are bacteria, among which microorganisms belonging to the genera Escherichia, Bacillus and Corynebacterium are more preferred.

Preferred microorganisms belonging to the genus Escherichia include those belonging to Escherichia coli; preferred microorganisms belonging to the genus Bacillus include those belonging to Bacillus subtilis and Bacillus megaterium; and preferred microorganisms belonging to the genus Corynebacterium include those belonging to Corynebacterium glutamicum and Corynebacterium ammoniagenes.

The microorganism used in the above process may be any microorganism having the ability to produce a protein of the present invention, but is preferably a microorganism belonging to the genus Bacillus, more preferably a microorganism belonging to the genus Bacillus and having the bacilysin-synthesizing activity, further preferably a microorganism belonging to a species selected from the group consisting of Bacillus subtilis, Bacillus amyloliquefaciens, Bacillus coagulans, Bacillus licheniformis, Bacillus megaterium and Bacillus pumilus, and most preferably a strain selected from the group consisting of Bacillus subtilis ATCC 15245, Bacillus subtilis ATCC 6633, Bacillus subtilis IAM 1213, Bacillus subtilis IAM 1107, Bacillus subtilis IAM 1214, Bacillus subtilis ATCC 9466, Bacillus subtilis IAM 1033, Bacillus subtilis ATCC 21555, Bacillus amyloliquefaciens IFO 3022 and Bacillus pumilus NRRL B-12025.

The treated matters of the culture include a concentrated culture, a dried culture, cells obtained by centrifuging the culture, products obtained by treating the cells by various means such as drying, freeze-drying, treatment with a surfactant, ultrasonication, mechanical friction, treatment with a solvent, enzymatic treatment, protein fractionation and immobilization, an enzyme preparation obtained by extracting the cells, etc.

In the above process, the kinds of amino acids used as substrates, their concentrations, the time of their addition, and the dipeptides produced are similar to those in the enzymatic process described in the above (iii) (1).

In the process using a culture of a microorganism or a treated matter of the culture as an enzyme source, the culture of the transformant or microorganism used as an enzyme source can also be used as the aqueous medium in addition to the aqueous media used in the enzymatic process described in the above (iii) (1).

Further, in the above process, ATP or compounds which can be metabolized by the transformant or microorganism to produce ATP, for example, sugars such as glucose, alcohols such as ethanol, and organic acids such as acetic acid may be added, as ATP source, to the aqueous medium according to need.

If necessary, a surfactant or an organic solvent may further be added to the aqueous medium. Any surfactant that promotes the formation of a dipeptide can be used. Suitable surfactants include nonionic surfactants such as polyoxyethylene octadecylamine (e.g., Nymeen S-215, NOF Corporation), cationic surfactants such as cetyltrimethylammonium bromide and alkyldimethylbenzylammonium chloride (e.g., Cation F2-40E, NOF Corporation), anionic surfactants such as lauroyl sarcosinate, and tertiary amines such as alkyldimethylamine (e.g., Tertiary Amine FB, NOF Corporation), which may be used alone or in combination. The surfactant is usually used at a concentration of 0.1 to 50 g/l. As the organic solvent, xylene, toluene, aliphatic alcohols, acetone, ethyl acetate, etc. may be used usually at a concentration of 0.1 to 50 ml/l.

When the culture or a treated matter of the culture is used as the enzyme source, the amount of the enzyme source to be added varies according to its specific activity, etc., but is, for example, 5 to 1000 mg (wet cell weight), preferably 10 to 400 mg per mg of amino acid used as a substrate.

The dipeptide-forming reaction is carried out in the aqueous medium at pH 5 to 11, preferably pH 6 to 10, at 20 to 65° C., preferably 25 to 55° C., more preferably 30 to 45° C., for 1 minute to 150 hours, preferably 3 minutes to 120 hours, preferably 30 minutes to 100 hours.

In the processes described in the above (iii) (1) and (2), recovery of the dipeptide formed and accumulated in the aqueous medium can be carried out by ordinary methods using active carbon, ion-exchange resins, etc. or by means such as extraction with an organic solvent, crystallization, thin layer chromatography and high performance liquid chromatography.

Certain embodiments of the present invention are illustrated in the following examples. These examples are not to be construed as limiting the scope of the invention.

EXAMPLE 1

Search for a Protein Having the Dipeptide-Synthesizing Activity utilizing a Database By using, as a query, the amino acid sequence of D-Ala-D-Ala ligase gene derived from *Bacillus subtilis* 168 [Nature, 390, 249-256 (1997)], a search for a gene encoding a protein showing similarity which is present in the genomic DNA sequences of *Bacillus subtilis* 168 was carried out using the similarity search function of Subtilist (http://genolist.pasteur.fr/SubtiList/) which is a database of the genomic DNA of *Bacillus subtilis* 168.

From the sequences obtained as a result of the search, genes encoding the amino acid sequences shown in SEQ ID NOS: 33, 34 and 35 which are D-Ala-D-Ala ligase motifs [Biochemistry, 30, 1673 (1991)] and encoding proteins whose function had already been clarified were excluded. Of the remaining sequences, the sequence showing the highest similarity (29.1%) to the D-Ala-D-Ala ligase motif was selected as a gene of unknown function ywfE.

The nucleotide sequence of ywfE is shown in SEQ ID NO: 9, and the amino acid sequence of the protein encoded by the nucleotide sequence is shown in SEQ ID NO: 1.

EXAMPLE 2

Construction of a Strain Expressing ywfE Gene

On the basis of the information on the nucleotide sequence obtained in Example 1, a ywfE gene fragment of *Bacillus subtilis* was obtained in the following manner.

That is, *Bacillus subtilis* 168 (ATCC 23857) was inoculated into LB medium [10 g/l Bacto-tryptone (Difco), 5 g/l yeast extract (Difco) and 5 g/l sodium chloride] and subjected to static culture overnight at 30° C. After the culturing, the chromosomal DNA of the microorganism was isolated and purified according to the method using saturated phenol described in Current Protocols in Molecular Biology.

By using a DNA synthesizer (Model 8905, PerSeptive Biosystems, Inc.), DNAs having the nucleotide sequences shown in SEQ ID NOS: 19 to 22 (hereinafter referred to as primer A, primer B, primer C and primer D, respectively) were synthesized. Primer A has a sequence wherein a nucleotide sequence containing the XhoI recognition sequence is added to the 5' end of a region of the *Bacillus subtilis* chromosomal DNA containing the initiation codon of ywfE. Primer B has a sequence wherein a nucleotide sequence containing the BamHI recognition sequence is added to the 5' end of a nucleotide sequence complementary to a sequence containing the termination codon of ywfE. Primer C has a sequence wherein a nucleotide sequence containing the EcoRI recognition sequence is added to the 5' end of the nucleotide sequence of trp promoter region of expression vector pTrS30 containing trp promoter [prepared from *Escherichia coli* JM109/pTrS30 (FERM BP-5407)]. Primer D has a sequence wherein a nucleotide sequence containing the XhoI recognition sequence is added to the 5' end of a sequence complementary to the sequence of trp promoter region of expression vector pTrS30 containing trp promoter.

A ywfE gene fragment was amplified by PCR using the above primer A and primer B, and as a template, the chromosomal DNA of *Bacillus subtilis*. A trp promoter region fragment was amplified by PCR using primer C and primer D, and as a template, pTrS30. PCR was carried out by 30 cycles, one cycle consisting of reaction at 94° C. for one minute, reaction at 55° C. for 2 minutes and reaction at 72° C. for 3 minutes, using 40 µl of a reaction mixture comprising 0.1 µg of the chromosomal DNA or 10 ng of pTrS30 as a template, 0.5 µmol/l each of the primers, 2.5 units of Pfu DNA polymerase (Stratagene), 4 µl of buffer for Pfu DNA polymerase (10×) (Stratagene) and 200 µmol/l each of dNTPs (dATP, dGTP, dCTP and dTTP).

One-tenth of each of the resulting reaction mixtures was subjected to agarose gel electrophoresis to confirm that a ca. 1.4 kb DNA fragment corresponding to the ywfE gene fragment and a ca. 0.3 kb DNA fragment corresponding to the trp promoter region fragment were respectively amplified in the PCR using primer A and primer B and the PCR using primer C and primer D. Then, the remaining reaction mixture was mixed with an equal amount of phenol/chloroform (1 vol/1 vol) saturated with TE [10 mmol/l Tris-HCl (pH 8.0), 1 mmol/l EDTA]. The resulting solution was centrifuged, and the obtained upper layer was mixed with a two-fold volume of cold ethanol and allowed to stand at −80° C. for 30 minutes. The resulting solution was centrifuged to precipitate DNA, and the obtained DNA was dissolved in 20 µl of TE.

The thus obtained solutions (5 µl each) were respectively subjected to reaction to cleave the DNA amplified using primer A and primer B with restriction enzymes XhoI and BamHI and to reaction to cleave the DNA amplified using primer C and primer D with restriction enzymes EcoRI and XhoI. DNA fragments were separated by agarose gel electrophoresis, and a 1.4 kb fragment containing ywfE and a 0.3 kb fragment containing trp promoter region were respectively recovered using GENECLEAN II Kit (BIO 101).

pTrs30 [a trp promoter-containing expression vector prepared from *Escherichia coli* JM109/pTrS30 (FERM BP-5407), 0.2 µg] was cleaved with restriction enzymes EcoRI and BamHI. DNA fragments were separated by agarose gel electrophoresis and a 4.5 kb DNA fragment was recovered in the same manner as above.

The 1.4 kb fragment containing ywfE, the 0.3 kb fragment containing trp promoter region and the 4.5 kb DNA fragment obtained above were subjected to ligation reaction using a ligation kit (Takara Shuzo Co., Ltd.) at 16° C. for 16 hours.

*Escherichia coli* NM522 (Stratagene) was transformed using the reaction mixture according to the method using calcium ion [Proc. Natl. Acad. Sci. USA, 69, 2110 (1972)], spread on LB agar medium containing 50 µg/ml ampicillin, and cultured overnight at 30° C.

A plasmid was extracted from a colony of the transformant that grew on the medium according to a known method and the structure of the plasmid was analyzed using restriction enzymes, whereby it was confirmed that expression vector pPE43 containing ywfE ligated downstream of the trp promoter was obtained (FIG. 1).

EXAMPLE 3

Production of a Dipeptide

*Escherichia coli* NM522 carrying pPE43 (*Escherichia coli* NM522/pPE43) obtained in Example 2 was inoculated into 8 ml of LB medium containing 50 μg/ml ampicillin in a large test tube, and cultured at 28° C. for 17 hours. The 10 resulting culture was centrifuged to obtain wet cells.

A reaction mixture (0.1 ml) comprising 60 mg/ml (final concentration) wet cells, 120 mmol/l potassium phosphate buffer (pH 7.4), 60 mmol/l magnesium chloride, 60 mmol/l ATP, 30 mmol/l L-Ala, 30 mmol/l L-Gln and 0.4% Nymeen S-215 was prepared, and reaction was carried out at 37° C. for 3 minutes.

After the completion of reaction, the reaction product was derivatized by the dinitrophenol method and then analyzed by HPLC. The HPLC analysis was carried out using, as a separation column, Lichrosorb-RP-18 column (Kanto Kagaku) and, as an eluent, 1% (v/v) phosphoric acid and 25% (v/v) acetonitrile at a flow rate of 0.7 ml/min. As a result, it was confirmed that 120 mg/l L-alanyl-L-glutamine (L-Ala-L-Gln) was formed and accumulated in the reaction mixture.

Formation of L-Ala-L-Gln was not observed when the reaction was carried out using cells of *Escherichia coli* NM522/pTrS31, which is a control strain carrying only a vector.

EXAMPLE 4

Purification of C-Terminal His-Tagged Recombinant Dipeptide Synthetase

By using the above DNA synthesizer, DNAs having the nucleotide sequences shown in SEQ ID NOS: 23 and 24 (hereinafter referred to as primer E and primer F, respectively) were synthesized. Primer E has a nucleotide sequence containing a region wherein the initiation codon of ywfE (atg) is substituted by the NcoI recognition sequence (ccatgg). Primer F has a nucleotide sequence containing a region wherein the termination codon of ywfE is substituted by the BamHI recognition sequence (ggatcc).

PCR was carried out using the chromosomal DNA of *Bacillus subtilis* 168 (ATCC 23857) as a template and the above primer E and primer F as a set of primers. That is, PCR was carried out by 30 cycles, one cycle consisting of reaction at 94° C. for one minute, reaction at 55° C. for 2 minutes and reaction at 72° C. for 3 minutes, using 40 μl of a reaction mixture comprising 0.1 μg of the chromosomal DNA, 0.5 μmol/l each of the primers, 2.5 units of Pfu DNA polymerase, 4 μl of buffer for Pfu DNA polymerase (10×) and 200 μmol/l each of dNTPs.

One-tenth of the resulting reaction mixture was subjected to agarose gel electrophoresis to confirm that a ca. 1.4 kb fragment corresponding to the ywfE fragment was amplified. Then, the remaining reaction mixture was mixed with an equal amount of phenol/chloroform saturated with TE. The resulting solution was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 μl of TE.

The thus obtained solution (5 μl) was subjected to reaction to cleave the amplified DNA with restriction enzymes NcoI and BamHI. DNA fragments were separated by agarose gel electrophoresis, and a 1.4 kb DNA fragment containing ywfE was recovered using GENECLEAN II Kit.

C-Terminal His-tagged recombinant expression vector pQE60 (Qiagen, Inc.) (0.2 μg) was cleaved with restriction enzymes NcoI and BamHI. DNA fragments were separated by agarose gel electrophoresis, and a 3.4 kb DNA fragment was recovered in the same manner as above.

The 1.4 kb DNA fragment containing ywfE and the 3.4 kb DNA fragment obtained above were subjected to ligation reaction using a ligation kit at 16° C. for 16 hours.

*Escherichia coli* NM522 was transformed using the ligation reaction mixture according to the method using calcium ion, spread on LB agar medium containing 50 μg/ml ampicillin, and cultured overnight at 30° C.

Figure 2:
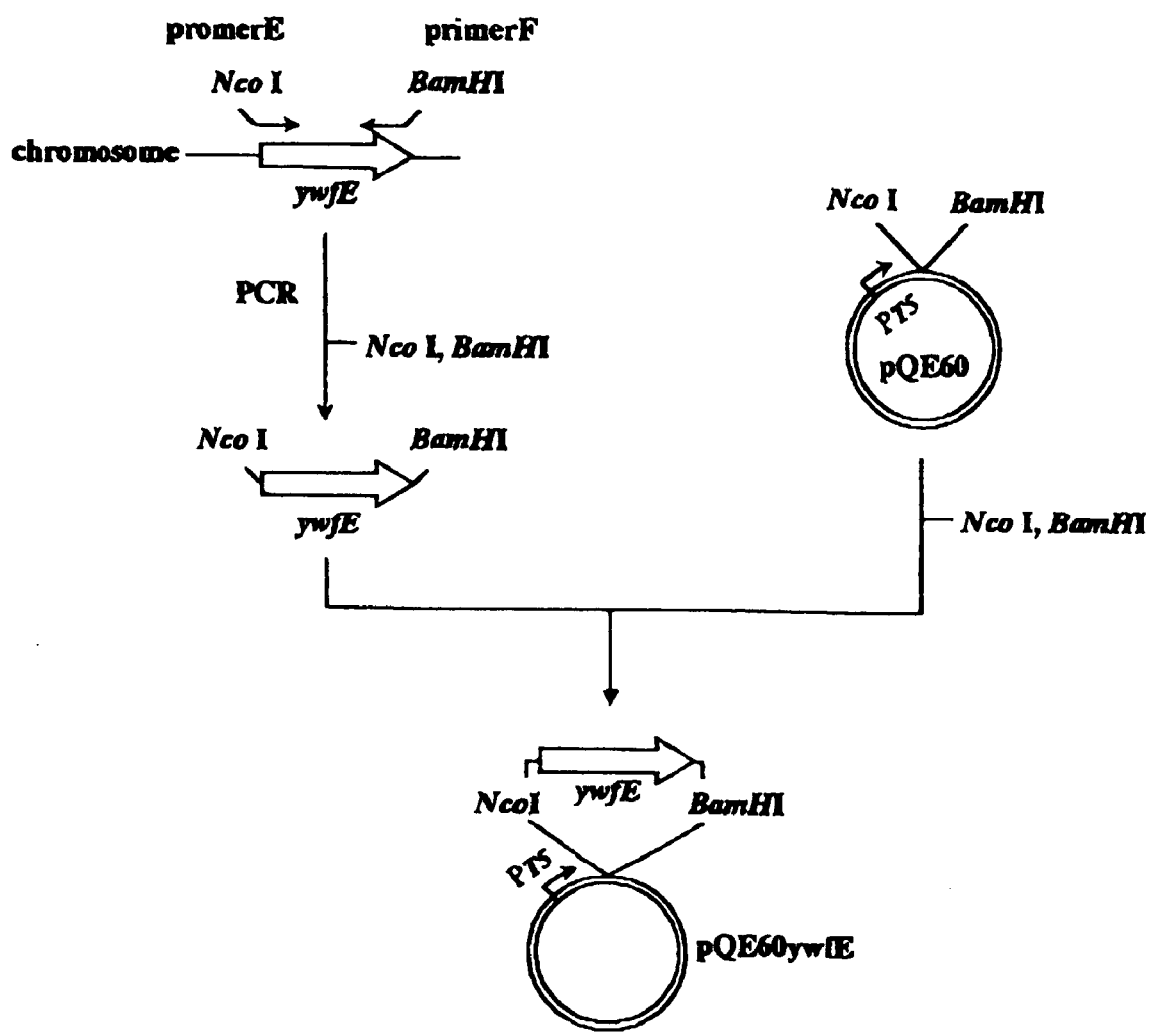
FIG. 2 shows the steps for constructing plasmid pQE60ywfE.

A plasmid was extracted from a colony of the transformant that grew on the medium according to a known method and the structure of the plasmid was analyzed using restriction enzymes, whereby it was confirmed that pQE60ywfE, which is a C-terminal His-tagged ywfE expression vector, was obtained (FIG. 2).

*Escherichia coli* NM522 carrying pQE60ywfE (*Escherichia coli* NM522/pQE60ywfE) was inoculated into 8 ml of LB medium containing 50 μg/ml ampicillin in a large test tube, and cultured at 28° C. for 17 hours. The resulting culture was inoculated into 50 ml of LB medium containing 50 μg/ml ampicillin in a 250-ml Erlenmeyer flask, and cultured at 30° C. for 3 hours. Then, isopropyl-β-D-thiogalactopyranoside (IPTG) was added to give a final concentration of 1 mmol/l, followed by further culturing at 30° C. for 4 hours. The resulting culture was centrifuged to obtain wet cells, and a His-tagged recombinant enzyme was purified from the wet cells using HisTrap (His-tagged protein purification kit, Amersham Pharmacia Biotech) according to the instructions attached thereto.

EXAMPLE 5

Production of Dipeptides Using the His-Tagged Recombinant Enzyme (1)

(i) A reaction mixture (0.1 ml) comprising 0.04 mg of the purified His-tagged recombinant enzyme obtained in Example 4, 100 mmol/l Tris-HCl (pH 8.0), 60 mmol/l magnesium chloride, 60 mmol/l ATP, 30mmol/l L-Ala and 30 mmol/l L-Gln was prepared, and reaction was carried out at 37° C. for 16 hours.

After the completion of reaction, the reaction product was analyzed in the same manner as in Example 3 above, whereby it was confirmed that 3.7 g/l L-Ala-L-Gln and 0.3 g/l L-alanyl-L-alanine (L-Ala-L-Ala) were formed and accumulated in the reaction mixture.

(ii) Reactions were carried out under the same conditions as in the above (i) using reaction mixtures having the same composition as that of the reaction mixture of the above (i) except that 0.01 mg of the enzyme was used and L-Phe, L-Met, L-Leu and L-Val, respectively, were used in place of L-Gln.

After the completion of reactions, the reaction products were analyzed in the same manner as in Example 3 above, whereby it was confirmed that the following dipeptides were formed and accumulated in the respective reaction mixtures: 7.0 g/l L-alanyl-L-phenylalanine (L-Ala-L-Phe) alone; 7.0 g/l L-alanyl-L-methionine (L-Ala-L-Met) and 0.03 g/l L-Ala-L-Ala; 5.0 g/l L-alanyl-L-leucine (L-Ala-L-Leu) and 0.2 g/l L-Ala-L-Ala; and 1.6 g/l L-alanyl-L-valine (L-Ala-L-Val) and 0.3 g/l L-Ala-L-Ala.

(iii) Reactions were carried out under the same conditions as in the above (i) using reaction mixtures having the same composition as that of the reaction mixture of the above (i)

except that 0.01 mg of the enzyme was used, Gly was used in place of L-Ala, and L-Phe and L-Met, respectively, were used in place of L-Gln.

After the completion of reactions, the reaction products were analyzed in the same manner as in Example 3 above, whereby it was confirmed that 5.2 g/l glycyl-L-phenylalanine (Gly-L-Phe) and 1.1 g/l glycyl-L-methionine (Gly-L-Met) were formed and accumulated in the respective reaction mixtures.

When ATP was excluded from the compositions of the above reaction mixtures, no dipeptide was formed.

The above results revealed that the ywfE gene product has the activity to produce, in the presence of ATP, the following dipeptides: L-Ala-L-Gln plus L-Ala-L-Ala, L-Ala-L-Phe, L-Ala-L-Met plus L-Ala-L-Ala, L-Ala-L-Leu plus L-Ala-L-Ala, or L-Ala-L-Val plus L-Ala-L-Ala from L-Ala plus L-Gln, L-Phe, L-Met, L-Leu or L-Val; and Gly-L-Phe or Gly-L-Met from Gly plus L-Phe or L-Met.

EXAMPLE 6

Production of Dipeptides Using the His-Tagged Recombinant Enzyme (2)

A reaction mixture (0.1 ml) comprising 0.04 mg of the purified His-tagged recombinant enzyme obtained in Example 4, 100 mmol/l Tris-HCl (pH 8.0), 60 mmol/l magnesium chloride and 60 mmol/l ATP was prepared. To this mixture were respectively added combinations of L-amino acids, Gly or β-Ala shown in the first row of Table 1 and L-amino acids, Gly or β-Ala shown in the leftmost column of Table 1 to give a concentration of 30 mmol/l each, and the resulting mixtures were subjected to reaction at 37° C. for 16 hours. After the completion of reactions, the reaction products were analyzed by HPLC, whereby it was confirmed that the dipeptides shown in Table 1 were formed.

TABLE 1

|  | Ala | Gln | Glu | Gly | Val | Leu | Ile | Pro |
|---|---|---|---|---|---|---|---|---|
| Ala | AlaAla | AlaGln AlaAla | AlaAla | AlaGly AlaAla | AlaVal AlaAla | AlaLeu AlaAla | AlaIle AlaAla | AlaAla |
| Gln |  | X | X | GlyGln GlyGly | X | X | X | X |
| Glu |  |  |  | GlyGly |  |  |  |  |
| Gly |  |  |  | GlyGly |  |  |  | GlyGly |
| Val |  |  |  |  |  |  |  |  |
| Leu |  |  |  |  |  |  |  |  |
| Ile |  |  |  |  |  |  |  |  |
| Pro |  |  |  |  |  |  |  |  |
| Phe |  |  |  |  |  |  |  |  |
| Trp |  |  |  |  |  |  |  |  |
| Met |  |  |  |  |  |  |  |  |
| Ser |  |  |  |  |  |  |  |  |
| Thr |  |  |  |  |  |  |  |  |
| Cys |  |  |  |  |  |  |  |  |
| Asn |  |  |  |  |  |  |  |  |
| Tyr |  |  |  |  |  |  |  |  |
| Lys |  |  |  |  |  |  |  |  |
| Arg |  |  |  |  |  |  |  |  |
| His |  |  |  |  |  |  |  |  |
| Asp |  |  |  |  |  |  |  |  |
| α AB |  |  |  |  |  |  |  |  |
| β-Ala |  |  |  |  |  |  |  |  |
| Cit |  |  |  |  |  |  |  |  |

|  | Phe | Trp | Met | Ser | Thr | Cys | Asn | Tyr |
|---|---|---|---|---|---|---|---|---|
| Ala | AlaPhe AlaAla | AlaTrp AlaAla | AlaMet | AlaSer AlaAla | AlaThr AlaAla | AlaAla O | AlaAsn AlaAla | AlaTyr AlaAla |
| Gln | O | X | MetMet | SerGln SerSer | ThrGln ThrThr | O | X | X |
| Glu |  |  |  |  |  |  |  |  |
| Gly | GlyPhe | GlyGly O | GlyMet GlyGly | GlySer GlyGly SerGly SerSer | GlyThr GlyGly ThrGly ThrThr | GlyGly O | GlyGly | GlyTyr GlyGly |
| Val |  | X |  |  |  |  |  |  |
| Leu |  |  | MetMet |  | ThrLeu |  |  |  |
| Ile |  |  | MetMet |  |  |  |  |  |
| Pro |  |  | MetMet | SerSer | ThrThr |  |  |  |
| Phe |  |  | MetPhe MetMet | SerPhe | ThrPhe ThrThr |  |  |  |
| Trp |  |  |  |  |  |  |  |  |
| Met |  |  | MetMet | SerMet | ThrMet ThrThr | MetMet O |  | MetTyr MetMet |

TABLE 1-continued

|     |   |   |   |          | SerThr SerSer ThrSer ThrThr |   |   | SerTyr SerSer |
|-----|---|---|---|----------|-----------------------------|---|---|---------------|
| Ser | \ | \ | \ | SerSer   |                             |   |   |               |
| Thr | \ | \ | \ |          | ThrThr                      |   |   |               |
| Cys | \ | \ | \ | \        | \                           |   |   |               |
| Asn | \ | \ | \ | \        | \                           |   |   |               |
| Tyr | \ | \ | \ | \        | \                           |   |   |               |
| Lys | \ | \ | \ | \        | \                           | \ |   |               |
| Arg | \ | \ | \ | \        | \                           | \ | \ |               |
| His | \ | \ | \ | \        | \                           | \ | \ | \             |
| Asp | \ | \ | \ | \        | \                           | \ | \ | \             |
| α-AB| \ | \ | \ | \        | \                           | \ | \ | \             |
| β-Ala| \| \ | \ | \        | \                           | \ | \ | \             |
| Cit | \ | \ | \ | \        | \                           | \ | \ | \             |

|       | Lys            | Arg                       | His             | Asp           | α-AB         | β-Ala   | Cit     | Azaserine | Theanine |
|-------|----------------|---------------------------|-----------------|---------------|--------------|---------|---------|-----------|----------|
| Ala   | AlaAla ○       | AlaArg AlaAla             | AlaHis AlaAla   | AlaAla        | AlaAla ○     |         | AlaAla ○| AlaAla ○  | AlaAla ○ |
| Gln   | X              | X                         | X               | X             | ○            |         |         |           |          |
| Glu   |                |                           |                 |               |              |         |         |           |          |
| Gly   | GlyGly ○       | GlyArg GlyGly             | GlyGly          | GlyGly        | GlyGly ○     |         | ○       |           |          |
| Val   |                |                           |                 |               |              |         |         |           |          |
| Leu   |                |                           |                 |               |              |         |         |           |          |
| Ile   |                |                           |                 |               |              |         |         |           |          |
| Pro   |                |                           |                 |               |              |         |         |           |          |
| Phe   |                |                           |                 | X             | ○            |         |         |           |          |
| Trp   |                |                           |                 |               |              |         |         |           |          |
| Met   | MetMet ○       |                           | MetMet ○        |               | ○            |         |         |           |          |
| Ser   |                |                           | SerHis          | SerSer ○      |              |         |         |           |          |
| Thr   |                |                           |                 | ThrThr ○      |              |         |         |           |          |
| Cys   |                |                           |                 |               |              |         |         |           |          |
| Asn   |                |                           |                 |               |              |         |         |           |          |
| Tyr   |                |                           |                 |               |              |         |         |           |          |
| Lys   |                |                           |                 |               |              |         |         |           |          |
| Arg   | \              |                           |                 |               | ○            |         |         |           |          |
| His   | \              | \                         |                 |               | β-AlaHis     |         |         |           |          |
| Asp   | \              | \                         | \               |               |              |         |         |           |          |
| α-AB  | \              | \                         | \               | \             | ○            |         |         |           |          |
| β-Ala | \              | \                         | \               | \             | \            |         |         |           |          |
| Cit   | \              | \                         | \               | \             | \            | ○       |         |           |          |

The dipeptides formed by the reaction using, as substrates, two (or one) kinds of L-amino acids, Gly or β-Ala shown in the first row and the leftmost column of Table 1 are shown in the respective cell of the table. In the table, ○ means that a dipeptide was formed though its sequence was unidentified; X means that formation of a dipeptide was not confirmed; and a blank means that reaction was not carried out.

EXAMPLE 7

Production of a Dipeptide using the Strain Expressing the His-Tagged Recombinant Enzyme

*Escherichia coli* NM522/pQE60ywfE obtained in Example 4 was inoculated into 8 ml of LB medium containing 50 μg/ml ampicillin in a large test tube, and cultured at 28° C. for 17 hours. The resulting culture was inoculated into 50 ml of LB medium containing 50 μg/ml ampicillin in a 250-ml Erlenmeyer flask, and cultured at 30° C. for 3 hours. Then, isopropyl-β-D-thiogalactopyranoside (IPTG) was added to give a final concentration of 1 mmol/l, followed by further culturing at 30° C. for 4 hours. The resulting culture was centrifuged to obtain wet cells.

A reaction mixture (20 ml, pH 7.2) comprising 200 g/l wet cells, 50 g/l glucose, 5 g/l phytic acid (diluted to neutrality with 33% conc. sodium hydroxide solution), 15 g/l potassium dihydrogenphosphate, 5 g/l magnesium sulfate heptahydrate, 4 g/l Nymeen S-215, 10 ml/l xylene, 200 mmol/l L-Ala and 200 mmol/l L-Gln was put in a 50-ml beaker, and reaction was carried out at 32° C. at 900 rpm for 2 hours. During the reaction, the pH of the reaction mixture was maintained at 7.2 by using 2 mol/l potassium hydroxide.

The reaction product was analyzed by the same method as in Example 3, whereby it was confirmed that 25 mg/l L-Ala-L-Gln was accumulated.

29

EXAMPLE 8

Cloning of Genes Corresponding to the ywfE Gene from Various Microorganisms of the Genus *Bacillus* and Analysis Thereof On the basis of the nucleotide sequence shown in SEQ ID NO: 9, genes corresponding to the ywfE gene which exist in *Bacillus subtilis* ATCC 15245, ATCC 6633, IAM 1213, IAM 1107, IAM 1214, ATCC 9466, IAM 1033 and ATCC 21555, *Bacillus amyloliquefaciens* IFO 3022 and *Bacillus pumilus* NRRL B-12025 were obtained in the following manner.

That is, *Bacillus subtilis* ATCC 15245, ATCC 6633, IAM 1213, IAM 1107, IAM 1214, ATCC 9466, IAM 1033 and ATCC 21555, *Bacillus amyloliquefaciens* IFO 3022 and *Bacillus pumilus* NRRL B-12025 were respectively inoculated into LB medium and subjected to static culture overnight at 30° C. After the culturing, the chromosomal DNAs of the respective microorganisms were isolated and purified according to the method using saturated phenol described in Current Protocols in Molecular Biology.

By using a DNA synthesizer (Model 8905, PerSeptive Biosystems, Inc.), DNAs having the nucleotide sequences shown in SEQ ID NOS: 25 and 26 (hereinafter referred to as primer G and primer H, respectively) were synthesized. Primer G has a sequence containing a region upstream of the initiation codon of ywfE of the chromosomal DNA of *Bacillus subtilis* 168, and primer H has a sequence complementary to a sequence containing a region downstream of the termination codon of ywfE.

PCR was carried out using each of the chromosomal DNAs of *Bacillus subtilis* ATCC 15245, ATCC 6633, IAM 1213, IAM 1107, IAM 1214, ATCC 9466, IAM 1033 and ATCC 21555 and *Bacillus amyloliquefaciens* IFO 3022 as a template and the above primer G and primer H as a set of primers. That is, PCR was carried out by 30 cycles, one cycle consisting of reaction at 94° C. for one minute, reaction at 55° C. for 2 minutes and reaction at 72° C. for 3 minutes, using 40 µl of a reaction mixture comprising 0.1 µg of the chromosomal DNA, 0.5 µmol/l each of the primers, 2.5 units of Pfu DNA polymerase, 4 µl of buffer for Pfu DNA polymerase (10×) and 200 µmol/l each of dNTPs.

One-tenth of each of the resulting reaction mixtures was subjected to agarose gel electrophoresis to confirm that a ca. 1.4 kb fragment corresponding to the ywfE fragment was amplified. Then, the remaining reaction mixture was mixed with an equal amount of phenol/chloroform saturated with TE. The resulting solution was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 µl of TE.

Each of the thus obtained 1.4 kb DNA fragments derived from the chromosomal DNAs of the respective strains and pCR-blunt (Invitrogen Corp.) were subjected to ligation reaction using a ligation kit at 16° C. for 16 hours.

*Escherichia coli* NM522 was transformed using each ligation reaction mixture according to the method using calcium ion, spread on LB agar medium containing 50 µg/ml ampicillin, and cultured overnight at 30° C.

A plasmid was extracted from a colony of each transformant that grew on the medium according to a known method and the structure of each plasmid was analyzed using restriction enzymes. As a result, it was confirmed that the following plasmids containing a gene corresponding to the ywfE gene were obtained: pYWFE1 (derived from ATCC 15245(SEQ ID NO: 36)), pYWFE2 (derived from ATCC 6633(SEQ ID NO: 10)), pYWFE3 (derived from IAM 1213(SEQ ID NO: 11)), pYWFE4 (derived from IAM 1107(SEQ ID NO: 12)), pYWFE5 (derived from IAM 1214(SEQ ID NO: 13)), pYWFE6 (derived from ATCC 9466), pYWFE7 (derived from IAM 1033(SEQ ID NO: 36)), pYWFE8 (derived from ATCC 21555(SEQ ID NO: 14)) and pYWFE9 (derived from IFO 3022(SEQ ID NO: 15)).

On the other hand, a gene corresponding to ywfE derived from *Bacillus pumilus* NRRL B-12025(SEQ ID NO: 16) was obtained in the following manner.

PCR was carried out using the chromosomal DNA of the NRRL B-12025 strain prepared above as a template and DNAs respectively consisting of the nucleotide sequences shown in SEQ ID NOS: 27 and 28 as a set of primers. That is, PCR was carried out by 30 cycles, one cycle consisting of reaction at 98° C. for 5 seconds, reaction at 55° C. for 30 seconds and reaction at 72° C. for one minute, using 50 µl of a reaction mixture comprising 0.1 µg of the chromosomal DNA, 0.5 µmol/l each of the primers, 2.5 units of Z-taq polymerase (Takara Shuzo Co., Ltd.), 5 µl of buffer for Z-taq polymerase (10×) (Takara Shuzo Co., Ltd.) and 200 µmol/l each of dNTPs.

One-tenth of the resulting reaction mixture was subjected to agarose gel electrophoresis to confirm that a ca. 0.8 kb fragment was amplified. Then, the remaining reaction mixture was mixed with an equal amount of phenol/chloroform saturated with TE. The resulting mixture was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 µl of TE.

The thus obtained 0.8 kb fragment derived from the chromosomal DNA and pGEM T-easy (Promega Corp.) were subjected to ligation reaction using a ligation kit at 16° C. for 16 hours.

*Escherichia coli* DH5α was transformed using the reaction mixture according to the method using calcium ion, spread on LB agar medium containing 50 µg/ml ampicillin, and cultured overnight at 30° C.

A plasmid was extracted from the transformant obtained above and the nucleotide sequence of the ca. 0.8 kb DNA insert was determined, whereby a sequence from nucleotides 358 to 1160 in the nucleotide sequence shown in SEQ ID NO: 16 was confirmed.

The above plasmid was cleaved with EcoRI and then subjected to agarose gel electrophoresis to separate a DNA fragment. The DNA fragment was purified using GENECLEAN II Kit, and about 0.5 µg of the purified DNA fragment was DIG-labeled using DIG-High Prime DNA Labeling & Detection Starter Kit I (Roche Diagnostics Corp.) according to the instructions attached thereto.

Southern analysis of the chromosomal DNA of the NRRL B-12025 strain was carried out using the DIG-labeled DNA obtained above.

The chromosomal DNA of the NRRL B-12025 strain was completely digested with BamHI, EcoRI, HindIII, KpnI, PstI, SacI, SalI and SphI, respectively, and subjected to agarose gel electrophoresis to separate DNA fragments, followed by transfer to nylon membrane plus charge (Roche Diagnostics Corp.) according to an ordinary method.

After the DNA fragments were fixed on the nylon membrane by UV irradiation, Southern hybridization was carried out using the above probe DNA and the nylon membrane. The hybridization was carried out by bringing the nylon membrane into contact with the probe DNA at 65° C. for 16 hours, washing the nylon membrane twice with a solution consisting of 0.1% SDS and 2×SSC at room temperature for 5 minutes, and further washing the membrane twice with a solution consisting of 0.1% SDS and 0.5×SSC at 65° C. for 15 minutes. The other operations and conditions and detection of the hybridized DNA were carried out according to the instructions attached to the above-mentioned DIG-High Prime DNA Labeling & Detection Starter Kit I.

As a result, color development was observed at around 3.5 kbp of the fragments completely digested with HindIII and PstI.

Subsequently, the chromosomal DNA of the NRRL B-12025 strain was completely digested with HindIII and PstI, respectively, and subjected to agarose gel electrophoresis to separate DNA fragments. From the respective restriction enzyme-digested DNAs, 3-4 kbp fragments were purified using GENECLEAN II Kit, followed by autocyclization using a ligation kit.

On the basis of the nucleotide sequence of the 0.8 kb DNA fragment determined above, the nucleotide sequences shown in SEQ ID NOS: 29 and 30 were designed and synthesized, and they were used in PCR, as primers, using the cyclized DNA obtained above as a template. PCR was carried out by 30 cycles, one cycle consisting of reaction at 98° C. for 5 seconds, reaction at 55° C. for 30 seconds and reaction at 72° C. for 3 minutes and 30 seconds, using 50 µl of a reaction mixture comprising 10 ng of the cyclized DNA, 0.5 µmol/l each of the primers, 2.5 units of pyrobest polymerase (Takara Shuzo Co., Ltd.), 5 µl of buffer for pyrobest polymerase (10×) (Takara Shuzo Co., Ltd.) and 200 µmol/l each of dNTPs.

One-tenth of the resulting reaction mixture was subjected to agarose gel electrophoresis to confirm that a ca. 3.0 kb fragment was amplified. Then, the remaining reaction mixture was mixed with an equal amount of phenol/chloroform saturated with TE. The resulting mixture was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 µl of TE.

The thus obtained DNA fragment and Zero Blunt PCR Cloning Kit (Invitrogen Corp.) were subjected to ligation reaction using a ligation kit.

*Escherichia coli* NM522 was transformed using the reaction mixture according to the method using calcium ion, spread on LB agar medium containing 50 µg/ml ampicillin, and cultured overnight at 30° C.

A plasmid was extracted from a colony of the transformant that grew on the medium according to a known method and the structure of the plasmid was analyzed using restriction enzymes. As a result, it was confirmed that plasmid pYWFE10 (derived from NRRL B-12025) containing a gene corresponding to the ywfE gene was obtained.

The nucleotide sequences of the genes corresponding to the ywfE gene which are respectively contained in the plasmids pYWFE1 to pYWFE10 obtained above were determined using 373A DNA Sequencer.

The amino acid sequences of the proteins encoded by the genes respectively contained in pYWFE1, pYWFE6 and pYWFE7 were identical with the amino acid sequence of the protein encoded by the ywfE gene, whereas those of the proteins encoded by the genes respectively contained in pYWFE2, pYWFE3, pYWFE4, pYWFE5, pYWFE8, pYWFE9 and pYWFE10 were different from the amino acid sequence of the protein encoded by the ywfE gene.

The amino acid sequences of the proteins encoded by the genes corresponding to ywfE which are contained in pYWFE2, pYWFE3, pYWFE4, pYWFE5, pYWFE8, pYWFE9, pYWFE10, and pYWFE1 and pYWFE7 are shown in SEQ ID NOS: 2 to 8 and 1, respectively, and the nucleotide sequences of these genes are shown in SEQ ID NOS: 10 to 16 and 36, respectively.

EXAMPLE 9

Purification of C-Terminal His-Tagged Recombinant Dipeptide Synthetase

PCR was carried out using each of the chromosomal DNAS of *Bacillus subtilis* ATCC 15245, ATCC 6633, IAM 1213, IAM 1107, IAM 1214, ATCC 9466, IAM 1033 and ATCC 21555 and *Bacillus amyloliquefaciens* IFO 3022 as a template and primer A and primer B described in Example 2 as a set of primers. That is, PCR was carried out by 30 cycles, one cycle consisting of reaction at 94° C. for one minute, reaction at 55° C. for 2 minutes and reaction at 72° C. for 3 minutes, using 40 µl of a reaction mixture comprising 0.1 µg of the chromosomal DNA, 0.5 µmol/l each of the primers, 2.5 units of Pfu DNA polymerase, 4 µl of buffer for Pfu DNA polymerase (10×) and 200 µmol/l each of dNTPs.

When the chromosomal DNA of *Bacillus pumilus* NRRL B-12025 was used as a template, PCR was carried out using DNAs respectively having the nucleotide sequences shown in SEQ ID NOS: 31 and 32 as a set of primers under the same conditions as above.

One-tenth of each of the resulting reaction mixtures was subjected to agarose gel electrophoresis to confirm that a ca. 1.4 kb DNA fragment corresponding to the ywfE fragment was amplified. Then, the remaining reaction mixture was mixed with an equal amount of phenol/chloroform saturated with TE. The resulting mixture was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 µl of TE.

Each of the thus obtained solutions (5 µl) was subjected to reaction to cleave the amplified DNA with restriction enzymes NcoI and BamHI. DNA fragments were separated by agarose gel electrophoresis, and a 1.4 kb DNA fragment containing a gene corresponding to ywfE was recovered using GENECLEAN II Kit.

Subsequently, 0.2 µg of the C-terminal His-tagged recombinant expression vector pQE60 was cleaved with restriction enzymes NcoI and BamHI. DNA fragments were separated by agarose gel electrophoresis, and a 3.4 kb DNA fragment was recovered in the same manner as above.

Each of the 1.4 kb DNA fragments containing a gene corresponding to ywfE of *Bacillus subtilis* 168 and the 3.4 kb DNA fragment obtained above were subjected to ligation reaction using a ligation kit at 16° C. for 16 hours.

*Escherichia coli* NM522 was transformed using each ligation reaction mixture according to the method using calcium ion, spread on LB agar medium containing 50 µg/ml ampicillin, and cultured overnight at 30° C.

A plasmid was extracted from a colony of each transformant that grew on the medium according to a known method and the structure of each plasmid was analyzed using restriction enzymes. As a result, it was confirmed that the following C-terminal His-tagged gene expression vectors were obtained: pQE60ywfE1 (a vector containing the gene derived from ATCC 15245), pQE60ywfE2 (a vector containing the gene derived from ATCC 6633), pQE60ywfE3 (a vector containing the gene derived from IAM 1213), pQE60ywfE4 (a vector containing the gene derived from IAM 1107), pQE60ywfE5 (a vector containing the gene derived from IAM 1214), pQE60ywfE6 (a vector containing the gene derived from ATCC 9466), pQE60ywfE7 (a vector containing the gene derived from IAM 1033), pQE60ywfE8 (a vector containing the gene derived from ATCC 21555), pQE60ywfE9 (a vector containing the gene derived from IFO 3022) and pQE60ywfE10 (a vector containing the gene derived from NRRL B-12025).

*Escherichia coli* NM522/pQE60ywfE1 to NM522/pQE60ywfE10 strains obtained above were respectively inoculated into 8 ml of LB medium containing 50 μg/ml ampicillin in a large test tube, and cultured at 28° C. for 17 hours. Each of the resulting cultures was inoculated into 50 ml of LB medium containing 50 μg/ml ampicillin in a 250-ml Erlenmeyer flask, and cultured at 30° C. for 3 hours. Then, isopropyl-β-D-thiogalactopyranoside was added to give a final concentration of 1 mmol/l, followed by further culturing at 30° C. for 4 hours. The resulting culture was centrifuged to obtain wet cells, and His-tagged recombinant enzymes were purified from the respective wet cells using HisTrap according to the instructions attached thereto.

EXAMPLE 10

Production of Dipeptides Using Purified Enzymes

Reaction mixtures (0.1 ml each) comprising 0.04 mg of the respective recombinant enzymes obtained in Example 9, 100 mmol/l Tris-HCl (pH 8.0), 60 mmol/l magnesium chloride, 60 mmol/l ATP, 30 mmol/l L-Ala and 30 mmol/l L-Gln were prepared, and reactions were carried out at 37° C. for 16 hours.

After the completion of reactions, the reaction mixtures were analyzed by the method described in Example 3, whereby it was confirmed that 3.0 to 3.5 g/l L-Ala-L-Gln and 0.25 to 0.3 g/l L-Ala-L-Ala were formed and accumulated.

When ATP was excluded from the compositions of the above reaction mixtures, L-Ala-L-Gln or L-Ala-L-Ala was not formed at all.

The above results revealed that all of the products of the genes obtained in Example 8 have the activity to produce L-Ala-L-Gln and L-Ala-L-Ala from L-Ala and L-Gln in the presence of ATP.

The entire content of each reference, application, publication, patent and document cited herein is hereby incorporated herein in its entirely by reference.

SEQUENCE LISTING FREE TEXT

SEQ ID NO: 19—Description of Artificial Sequence: Primer
SEQ ID NO: 20—Description of Artificial Sequence: Primer
SEQ ID NO: 21—Description of Artificial Sequence: Primer
SEQ ID NO: 22—Description of Artificial Sequence: Primer
SEQ ID NO: 23—Description of Artificial Sequence: Primer
SEQ ID NO: 24—Description of Artificial Sequence: Primer
SEQ ID NO: 25—Description of Artificial Sequence: Primer
SEQ ID NO: 26—Description of Artificial Sequence: Primer
SEQ ID NO: 27—Description of Artificial Sequence: Primer
SEQ ID NO: 28—Description of Artificial Sequence: Primer
SEQ ID NO: 29—Description of Artificial Sequence: Primer
SEQ ID NO: 30—Description of Artificial Sequence: Primer
SEQ ID NO: 31—Description of Artificial Sequence: Primer
SEQ ID NO: 32—Description of Artificial Sequence: Primer
SEQ ID NO: 33—Description of Artificial Sequence: Amino acid sequence used in database search
SEQ ID NO: 34—Description of Artificial Sequence: Amino acid sequence used in database search
SEQ ID NO: 35—Description of Artificial Sequence: Amino acid sequence used in database search

---

What is claimed is:

1. A process for producing a dipeptide represented by formula (I):

R-R2    (I)

wherein R1 is an amino acid selected from the group consisting of L-alanine, L-methionine, L-serine, β-alanine, L-threonine, glycine, L-cysteine and L-α-aminobutyric acid, and $R^2$ is an amino acid selected from the group consisting of L-alanine, L-glutamine, L-glutamic acid, glycine, L-valine, L-leucine, L-isoleucine, L-proline, L-phenylalanine, L-tryptophan, L-methionine, L-serine, L-threonine, L-cysteine, L-asparagine, L-tyrosine, L-lysine, L-arginine, L-histidine, L-aspartic acid, L-α-aminobutyric acid, βalanine, L-azaserine, L-theanine, L-4- hydroxyprol me, L-3-hydroxyproline, L-ornithine, L-citrulline and L-6-diazo-5-oxo-norleucine except L-alanyl-L-alanine, which comprises:

contacting, in an aqueous medium, at least two amino acids which may be the same or different, and a transformed microorganism comprising a polynucleotide encoding a protein selected from the group consisting of the following [1] to [3]:

[1] a protein comprising the amino acid sequence of SF0 ID NO:1;

[2] a protein comprising an amino acid sequence wherein 1 to 20 amino acid residues are deleted, substituted or added in the amino acid sequence of SEQ ID NO: 1 and catalyzing the synthesis of a dipeptide represented by formula (I); and

[3] a protein comprising an amino acid sequence which shows 98% or more similarity determined by BLAST program to the amino acid sequence of SEQ ID NO: 1 and catalyzes the synthesis of a dipeptide represented by formula (I);

forming and accumulating the dipeptide in the medium; and recovering the dipeptide from the medium.

2. A process for producing a dipeptide represented by formula (I);

$R^1$-$R^2$    (I)

wherein $R^1$ is an amino acid selected from the group consisting of L-alanine, L-methionine, L-serine, β-alanine, L-threonine, glycine, L-cysteine and L-α-aminobutyric acid, and R2 is an amino acid selected from the group consisting of L-alanine, L-glutamine, L-glutamic acid, glycine, L-valine, L-leucine, L-isoleucine, L-proline, L-phenylalanine, L-tryptophan, L-methionine, L-serine, L-threonine, L-cysteine, L-asparagine, L-tyrosine, L-lysine, L-arginine, L-histidine, L-aspartic acid, L-α-aminobutyric acid, β-alanine, L-azaserine, L-theanine, L-4-hydroxyproline, L-3-hydroxyproline, L-ornithine, L-citrulline and L-6-diazo-5 -oxo-norleucine except L-alanyl-L-alanine, which comprises:

contacting an enzyme source and at least two amino acids which may be the same or different in an aqueous medium, said enzyme source being a culture of a microorganism transformed with a nucleic acid sequence selected from the group consisting of (a) to (e), or a treated matter of the culture:

(a) a nucleic acid sequence encoding the protein comprising the amino acid sequence of SEQ ID NO:1;

(b) a nucleic acid comprising the nucleotide sequence of SEQ ID NO:9;

(c) a nucleic acid sequence encoding a protein comprising an amino acid sequence wherein 1 to 20 amino acid residues are deleted, substituted or added in the amino acid sequence of SEQ ID NO: 1 and catalyzing the synthesis of the dipeptide represented by formula (I); and (d) a nucleic acid sequence which hybridizes with a nucleic acid sequence comprising the complement of a nucleotide sequence of SEQ ID NOS: 9 in the presence of 0.7 to 1.0 mol/l sodium chloride at 65° C., followed by washing in 0.1 to 2-fold concentrated SSC solution at 65° C. and which nucleic acid sequence encodes a protein which catalyzes the synthesis of a dipeptide represented by formula (I); and (e) a protein comprising an amino acid sequence which shows 98% or more similarity to the amino acid sequence of SEQ ID NO: 1 and catalyzes the synthesis of the dipeptide represented by formula (I);

forming and accumulating the dipeptide in the medium; and recovering the dipeptide from the medium wherein the treated matter of the culture is selected from the group consisting of a concentrated culture, a dried culture, cells obtained by centrifuging the culture and a product obtained by subjecting the cells to drying, freeze-drying, treatment with a surfactant and treatment with a solvent, and the treated matter of the culture has same enzymatic activity as the culture.

3. The process according to claim 2, wherein the microorganism is transformed with DNA derived from the genus *Bacillus*.

4. The process according to claim 3, wherein the microorganism belonging to the genus *Bacillus* has the ability to produce bacilysin.

5. The process according to claim 4, wherein the microorganism of the genus *Bacillus* is selected from the group consisting of *Bacillus subtilis, Bacillus amyloliquefaciens, Bacillus coagulans, Bacillus licheniformis, Bacillus megaterium* and *Bacillus pumilus*.

6. The process according to claim 2, wherein the microorganism is transformed with a recombinant nucleic acid sequence comprising the nucleotide sequence of SEQ ID NO: 9.

7. The process according to claim 6, wherein the microorganism transformed with a nucleic acid sequence comprising the nucleotide sequence of SEQ ID NO: 9 belongs to the genus *Escherichia*.

* * * * *

UNITED STATES PATENT AND TRADEMARK OFFICE
CERTIFICATE OF CORRECTION

| | |
|---|---|
| PATENT NO. | : 7,514,242 B2 |
| APPLICATION NO. | : 10/746264 |
| DATED | : April 7, 2009 |
| INVENTOR(S) | : Shin-ichi Hashimoto et al. |

It is certified that error appears in the above-identified patent and that said Letters Patent is hereby corrected as shown below:

In the Drawings:

SHEET 2:

Figure 2, "promerE" should read --primerE--.

COLUMN 1:

Line 42, "No. 209992/83,and" should read --No. 209992/83, and--.

COLUMN 2:

Line 21, "it contained," should read --if contained,--.

COLUMN 3:

Line 57, "Escherichia." should read --*Escherichia*--.

COLUMN 4:

Line 57, "*Bacillus* ." should read --*Bacillus.*--.

COLUMN 5:

Line 11, "Escherichia." should read --*Escherichia.*--; and
    Line 65, "formula (I)" should read --formula (I):--.

COLUMN 6:

Line 5, "shoes" should read --shows--; and
    Line 21, "catalyzes" should read --catalyze--.

UNITED STATES PATENT AND TRADEMARK OFFICE
CERTIFICATE OF CORRECTION

| | | |
|---|---|---|
| PATENT NO. | : 7,514,242 B2 | |
| APPLICATION NO. | : 10/746264 | |
| DATED | : April 7, 2009 | |
| INVENTOR(S) | : Shin-ichi Hashimoto et al. | |

It is certified that error appears in the above-identified patent and that said Letters Patent is hereby corrected as shown below:

COLUMN 7:

Line 49, "catalying" should read --catalyzing--; and
Line 63, "acid." should read --acid--.

COLUMN 8:

Line 57, "a nucleic" should read --nucleic--.

COLUMN 9:

Line 7, "includes" should read --include--.

COLUMN 10:

Line 16, "Eschericia," should read --*Eschericia*,--; and
Line 17, "Eschericia," (first occurrence) should read --*Eschericia*,--.

COLUMN 11:

Line 28, "coliJM109/" should read --coli JM109/--.

COLUMN 12:

Line 9, "*amyloliguefaciens.*" should read --*amyloliguefaciens,*--;
Line 19, "Pseudomonas" should read --*Pseudomonas*--; and "sp D-0110," should read --sp. D-0110,--;
Line 32, "Phormidium" should read --*Phormidium*--;
Line 58, "Saccharomyces, Schizosaccharomyces," should read --*Saccharomyces, Schizosaccharomyces,*--;
Line 59, "Kluyveromyces, Trichosporon, Schwanniomyces, Pichia" should read --*Kluyveromyces, Trichosporon, Schwanniomyces, Pichia*--; and
Line 60, "Candida," should read --*Candida,*--.

UNITED STATES PATENT AND TRADEMARK OFFICE
CERTIFICATE OF CORRECTION

PATENT NO. : 7,514,242 B2
APPLICATION NO. : 10/746264
DATED : April 7, 2009
INVENTOR(S) : Shin-ichi Hashimoto et al.

It is certified that error appears in the above-identified patent and that said Letters Patent is hereby corrected as shown below:

COLUMN 13:

Line 41, "vectors," should read --Vectors,--; and
Line 55, "Barathra." should read --*Barathra.*--.

COLUMN 14:

Line 33, "Eschericia," should read --*Eschericia,*--.

COLUMN 16:

Line 11, "unexamined" should read --Unexamined--.

COLUMN 18:

Line 29, "O-Ala," should read --β-Ala,--; and
Line 50, "L-a-AB and" should read --L-α-AB and--.

COLUMN 21:

Line 20, "utilizing" should read --Utilizing--.

COLUMN 24:

Line 42, "30mmol/l" should read --30 mmol/1--; and
Line 43, "mmol/1 L-Gin" should read --mmol/1 L-Gln--.

COLUMN 32:

Line 10, "DNAS" should read --DNAs--.

COLUMN 34:

Line 10, "in its entirely" should read --in its entirety--.

UNITED STATES PATENT AND TRADEMARK OFFICE
CERTIFICATE OF CORRECTION

PATENT NO. : 7,514,242 B2
APPLICATION NO. : 10/746264
DATED : April 7, 2009
INVENTOR(S) : Shin-ichi Hashimoto et al.

It is certified that error appears in the above-identified patent and that said Letters Patent is hereby corrected as shown below:

COLUMN 97:

Line 27, "wherein R1" should read --wherein $R^1$--;
Line 36, "βalanine," should read --β-alanine,--;
Line 37, "L-4- hydroxyprol me," should read --L-4-hydroxyproline,--;
Line 45, "[1]a" should read --[1] a--;
Line 46, "SF0ID" should read --SEQ ID--;
Line 47, "[2]a" should read --[2] a--; and
Line 53, "[3]a" should read --[3] a--.

COLUMN 98:

Line 23, "and R2" should read --and $R^2$--.

Signed and Sealed this

Twenty-fifth Day of August, 2009

David J. Kappos
*Director of the United States Patent and Trademark Office*

SEQUENCE LISTING

```
<160> NUMBER OF SEQ ID NOS: 36

<210> SEQ ID NO 1
<211> LENGTH: 472
<212> TYPE: PRT
<213> ORGANISM: Bacillus subtilis 168

<400> SEQUENCE: 1

Met Glu Arg Lys Thr Val Leu Val Ile Ala Asp Leu Gly Gly Cys Pro
 1               5                  10                  15

Pro His Met Phe Tyr Lys Ser Ala Ala Glu Lys Tyr Asn Leu Val Ser
            20                  25                  30

Phe Ile Pro Arg Pro Phe Ala Ile Thr Ala Ser His Ala Ala Leu Ile
        35                  40                  45

Glu Lys Tyr Ser Val Ala Val Ile Lys Asp Lys Asp Tyr Phe Lys Ser
    50                  55                  60

Leu Ala Asp Phe Glu His Pro Asp Ser Ile Tyr Trp Ala His Glu Asp
65                  70                  75                  80

His Asn Lys Pro Glu Glu Glu Val Val Glu Gln Ile Val Lys Val Ala
                85                  90                  95

Glu Met Phe Gly Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
```

```
            130                 135                 140
Phe Asn Lys Ala Gly Val Lys Ser Ile Lys Asn Lys Arg Val Thr Thr
145                 150                 155                 160

Leu Glu Asp Phe Arg Ala Ala Leu Glu Ile Gly Thr Pro Leu Ile
                165                 170                 175

Leu Lys Pro Thr Tyr Leu Ala Ser Ser Ile Gly Val Thr Leu Ile Thr
                180                 185                 190

Asp Thr Glu Thr Ala Glu Asp Glu Phe Asn Arg Val Asn Asp Tyr Leu
                195                 200                 205

Lys Ser Ile Asn Val Pro Lys Ala Val Thr Phe Glu Ala Pro Phe Ile
210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
                260                 265                 270

Glu Thr Ser His Ile Thr Pro Ser Ile Leu Asp Glu Glu Ala Lys Lys
                275                 280                 285

Lys Ile Val Glu Ala Ala Lys Lys Ala Asn Glu Gly Leu Gly Leu Gln
                290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
                340                 345                 350

Val Leu Cys Phe Gly Lys Asp Ala Asp Leu Pro Asp Gly Leu Leu Asp
                355                 360                 365

Gln Glu Pro Tyr Tyr Val Ala Asp Cys His Leu Tyr Pro Gln His Phe
                370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Ser Phe Ser Ala Ala Ala Pro Gly Thr Ser Val Asp Leu Thr Leu Phe
                420                 425                 430

Glu Ala Phe Asn Ser Ile Ala Ala Phe Glu Leu Lys Gly Ser Asn Ser
                435                 440                 445

Gln Asp Val Ala Glu Ser Ile Arg Gln Ile Gln Gln His Ala Lys Leu
450                 455                 460

Thr Ala Lys Tyr Val Leu Pro Val
465                 470

<210> SEQ ID NO 2
<211> LENGTH: 472
<212> TYPE: PRT
<213> ORGANISM: Bacillus subtilis ATCC6633

<400> SEQUENCE: 2

Met Glu Arg Lys Thr Val Leu Val Ile Ala Asp Leu Gly Gly Cys Pro
  1               5                  10                  15

Pro His Met Phe Tyr Lys Ser Ala Ala Glu Lys Tyr Asn Leu Val Ser
                 20                  25                  30
```

-continued

Phe Ile Pro Arg Pro Phe Ala Ile Thr Ala Ser His Ala Ala Leu Ile
         35                  40                  45

Glu Lys Tyr Ser Val Ala Val Ile Lys Asp Lys Asp Tyr Phe Gln Ser
 50                  55                  60

Leu Ala Asp Phe Glu His Pro Asp Ser Ile Tyr Trp Ala His Glu Asp
 65                  70                  75                  80

His Asp Lys Pro Glu Glu Val Val Glu Gln Ile Val Lys Val Ala
                 85                  90                  95

Gln Met Phe Glu Ala Asp Ala Ile Thr Thr Asn Asn Glu Leu Phe Ile
                100                 105                 110

Ala Pro Met Ala Lys Ala Cys Glu Arg Leu Gly Leu Arg Gly Ala Gly
             115                 120                 125

Val Gln Ala Ala Glu Asn Ala Arg Asp Lys Asn Lys Met Arg Asp Ala
         130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
                180                 185                 190

Asp Thr Glu Thr Ala Glu Asp Glu Phe Asn Arg Val Asn Asp Tyr Leu
            195                 200                 205

Lys Ser Ile Asn Val Pro Lys Ala Val Thr Phe Glu Ala Pro Phe Ile
            210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
                260                 265                 270

Glu Thr Ser His Ile Thr Pro Ser Ile Leu Asp Glu Glu Ala Lys Lys
            275                 280                 285

Lys Ile Val Glu Ala Ala Lys Lys Ala Asn Glu Gly Leu Gly Leu Gln
290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
                340                 345                 350

Val Leu Cys Phe Gly Lys Asp Ala Asp Leu Pro Asp Gly Leu Leu Asp
            355                 360                 365

Gln Glu Pro Tyr Tyr Val Ala Asp Cys His Leu Tyr Pro Gln His Phe
        370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Thr Phe Ser Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
        435                 440                 445

Gln Asp Val Ala Glu Ser Ile Arg Gln Ile Gln Gln His Ala Lys Leu

```
        450                 455                 460
Thr Ala Lys Tyr Val Leu Pro Val
465                 470

<210> SEQ ID NO 3
<211> LENGTH: 472
<212> TYPE: PRT
<213> ORGANISM: Bacillus subtilis IAM1213

<400> SEQUENCE: 3

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
            20                  25                  30

Phe Ile Pro Arg Pro Phe Ala Ile Thr Ala Ser His Ala Ala Leu Ile
        35                  40                  45

Glu Lys Tyr Ser Val Ala Val Ile Lys Asp Lys Asp Tyr Phe Lys Ser
    50                  55                  60

Leu Ala Asp Phe Glu His Pro Asp Ser Ile Tyr Trp Ala His Glu Asp
65                  70                  75                  80

His Asn Lys Pro Glu Glu Val Val Glu Gln Ile Val Lys Val Ala
                85                  90                  95

Glu Met Phe Gly Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
    130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
        275                 280                 285

Lys Ile Val Glu Ala Ala Lys Lys Ala Asn Glu Gly Leu Gly Leu Gln
    290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350
```

```
Val Leu Cys Phe Gly Lys Asp Ala Asp Leu Pro Asp Gly Leu Leu Asp
        355                 360                 365

Gln Glu Pro Tyr Tyr Val Ala Asp Cys His Leu Tyr Pro Gln His Phe
        370                 375                 380

Lys Gln Asn Gly Gln Ile Pro Glu Thr Ala Glu Asp Leu Val Ile Glu
385                 390                 395                 400

Ala Ile Asp Leu Pro Asp Gly Leu Leu Lys Gly Asp Thr Glu Ile Val
                405                 410                 415

Ser Phe Ser Ala Ala Pro Gly Thr Ser Val Asp Leu Thr Leu Phe
                420                 425                 430

Glu Ala Phe Asn Ser Ile Ala Ala Phe Glu Leu Lys Gly Ser Asn Ser
        435                 440                 445

Gln Asp Val Ala Glu Ser Ile Arg Gln Ile Gln Gln His Ala Lys Leu
        450                 455                 460

Thr Ala Lys Tyr Val Leu Pro Val
465                 470

<210> SEQ ID NO 4
<211> LENGTH: 472
<212> TYPE: PRT
<213> ORGANISM: Bacillus subtilis IAM1107

<400> SEQUENCE: 4

Met Glu Arg Lys Thr Val Leu Val Ile Ala Asp Leu Gly Gly Cys Pro
 1               5                  10                  15

Pro His Met Phe Tyr Lys Ser Ala Ala Glu Lys Tyr Asn Leu Val Ser
                20                  25                  30

Phe Ile Pro Arg Pro Phe Ala Ile Thr Ala Ser His Ala Ala Leu Ile
            35                  40                  45

Glu Lys Tyr Ser Val Ala Val Val Lys Asp Lys Asp Tyr Phe Lys Ser
        50                  55                  60

Leu Ala Asp Phe Glu His Pro Asp Ser Ile Tyr Trp Ala His Glu Asp
 65                  70                  75                  80

His Asn Lys Pro Glu Glu Val Val Glu Gln Ile Val Lys Val Ala
                85                  90                  95

Glu Met Phe Gly Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
    130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255
```

```
Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Ala Lys Lys
        275                 280                 285

Lys Ile Val Glu Ala Ala Lys Lys Ala Asn Glu Gly Leu Gly Leu Gln
        290                 295                 300

Asn Cys Ala Thr His Thr Glu Val Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
                340                 345                 350

Val Leu Cys Phe Gly Lys Asp Ala Asp Leu Pro Asp Gly Leu Leu Asp
                355                 360                 365

Gln Glu Pro Tyr Tyr Val Ala Asp Cys His Leu Tyr Pro Gln His Phe
            370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Phe
                405                 410                 415

Ser Phe Ser Ala Ala Pro Gly Thr Ser Val Asp Leu Thr Leu Phe
                420                 425                 430

Glu Ala Phe Asn Ser Ile Ala Ala Phe Glu Leu Lys Gly Ser Asn Ser
                435                 440                 445

Gln Asp Val Ala Glu Ser Ile Arg Gln Ile Gln Gln His Ala Lys Leu
            450                 455                 460

Thr Ala Lys Tyr Val Leu Pro Val
465                 470

<210> SEQ ID NO 5
<211> LENGTH: 472
<212> TYPE: PRT
<213> ORGANISM: Bacillus subtilis IAM1214

<400> SEQUENCE: 5

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
                20                  25                  30

Phe Ile Pro Arg Pro Phe Ala Ile Thr Ala Ser His Ala Ala Leu Ile
            35                  40                  45

Glu Lys Tyr Ser Val Ala Val Ile Lys Asp Lys Asp Tyr Phe Gln Ser
        50                  55                  60

Leu Ala Asp Phe Glu His Pro Asp Ser Ile Tyr Trp Ala His Glu Asp
65                  70                  75                  80

His Asp Lys Pro Glu Glu Val Val Glu Gln Ile Val Lys Val Ala
                85                  90                  95

Gln Met Phe Glu Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
        130                 135                 140

Phe Asn Lys Ala Gly Val Lys Ser Ile Lys Asn Lys Arg Val Thr Thr
```

```
                    145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Gly Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Ala Lys Lys
        275                 280                 285

Lys Ile Val Glu Ala Ala Lys Lys Ala Asn Glu Gly Leu Gly Leu Gln
    290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
        355                 360                 365

Gln Glu Pro Tyr Tyr Val Ala Asp Cys His Leu Tyr Pro Gln His Phe
    370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Thr Phe Ser Ala Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
        435                 440                 445

Gln Asp Val Ala Glu Ser Ile Arg Gln Ile Gln His Ala Lys Leu
    450                 455                 460

Thr Ala Lys Tyr Val Leu Pro Val
465                 470

<210> SEQ ID NO 6
<211> LENGTH: 472
<212> TYPE: PRT
<213> ORGANISM: Bacillus subtilis ATCC21555

<400> SEQUENCE: 6

Met Glu Arg Lys Thr Val Leu Val Ile Ala Asp Leu Gly Gly Cys Pro
1               5                   10                  15

Pro His Met Phe Tyr Lys Ser Ala Glu Lys Tyr Asn Leu Val Ser
                20                  25                  30

Phe Ile Pro Arg Pro Phe Ala Ile Thr Ala Ser His Ala Ala Leu Ile
            35                  40                  45
```

```
Glu Lys Tyr Ser Ile Ala Val Ile Lys Asp Lys Asp Tyr Phe Lys Ser
 50                  55                  60
Leu Ala Asp Phe Glu His Pro Asp Ser Ile Tyr Trp Ala His Glu Asp
 65                  70                  75                  80
His Asp Lys Pro Glu Glu Val Val Glu Ile Val Lys Val Ala
                 85                  90                  95
Asp Met Phe Gly Val Asp Ala Ile Thr Thr Asn Asn Glu Leu Phe Ile
                100                 105                 110
Ala Pro Met Ala Lys Ala Cys Lys Arg Leu Gly Leu Arg Gly Ala Gly
            115                 120                 125
Val Gln Ala Ala Glu Asn Ala Arg Asp Lys Asn Lys Met Arg Ala Ala
        130                 135                 140
Phe Asn Arg Ala Gly Val Lys Ser Ile Lys Asn Lys Arg Val Thr Thr
145                 150                 155                 160
Leu Glu Asp Phe Arg Ala Ala Leu Gln Glu Ile Gly Thr Pro Leu Ile
                165                 170                 175
Leu Lys Pro Thr Tyr Leu Ala Ser Ser Ile Gly Val Thr Leu Ile Lys
            180                 185                 190
Glu Met Glu Thr Ala Glu Ala Glu Phe Asn Arg Val Asn Glu Tyr Leu
        195                 200                 205
Lys Ser Ile Asn Val Pro Lys Ala Val Thr Phe Glu Ala Pro Phe Ile
210                 215                 220
Ala Glu Glu Phe Leu Gln Gly Glu Tyr Asp Asp Trp Tyr Glu Thr Ser
225                 230                 235                 240
Gly Tyr Ser Asp Tyr Ile Ser Ile Glu Gly Ile Met Ala Asp Gly Glu
                245                 250                 255
Tyr Phe Pro Val Ala Ile His Asp Lys Thr Pro Gln Ile Gly Phe Thr
            260                 265                 270
Glu Thr Ala His Ile Thr Pro Ser Ile Leu Asp Asp Ala Lys Arg
        275                 280                 285
Lys Ile Val Glu Ala Ala Lys Lys Ala Asn Glu Gly Leu Gly Leu Glu
290                 295                 300
Asn Cys Ala Thr His Thr Glu Ile Lys Leu Met Lys Asn Arg Glu Ala
305                 310                 315                 320
Gly Leu Ile Glu Ser Ala Ala Arg Phe Ala Gly Trp Asn Met Ile Pro
                325                 330                 335
Asn Ile Lys Lys Val Phe Gly Val Asp Met Ala Gln Leu Leu Leu Asp
            340                 345                 350
Val Leu Cys Tyr Gly Lys Glu Ala Asp Leu Pro Lys Gly Leu Leu Glu
        355                 360                 365
Gln Glu Pro Cys Tyr Val Ala Asp Cys His Leu Tyr Pro Gln His Phe
370                 375                 380
Lys Glu Asn Gly Gln Leu Pro Glu Thr Val Val Asp Phe Val Ile Glu
385                 390                 395                 400
Ser Ile Glu Ile Pro Asp Gly Val Leu Lys Gly Asp Thr Glu Leu Val
                405                 410                 415
Ser Phe Ser Ala Ala Glu Ala Gly Thr Ser Val Asp Leu Arg Leu Phe
            420                 425                 430
Glu Ala Phe Asn Ser Ile Ala Ala Phe Glu Leu Lys Gly Ser Asn Ser
        435                 440                 445
Asn Asp Val Ala Glu Ser Ile Lys Gln Ile Gln Gln Ala Lys Leu
450                 455                 460
Thr Ala Lys Tyr Ala Leu Ser Val
```

```
                        465                 470
```

<210> SEQ ID NO 7
<211> LENGTH: 472
<212> TYPE: PRT
<213> ORGANISM: Bacillus amyloliquefaciens IFO3022

<400> SEQUENCE: 7

```
Met Glu Arg Lys Thr Val Leu Val Ile Ala Asp Leu Gly Gly Cys Pro
 1               5                  10                  15

Pro His Met Phe Tyr Lys Ser Ala Ala Glu Lys Tyr Asn Leu Val Ser
             20                  25                  30

Phe Ile Pro Arg Pro Phe Ala Ile Thr Ala Ser His Ala Ala Leu Ile
         35                  40                  45

Glu Lys Tyr Ser Val Ala Val Ile Lys Asp Lys Asp Tyr Phe Lys Ser
     50                  55                  60

Leu Ala Asp Phe Glu His Pro Asp Ser Ile Tyr Trp Ala His Glu Asp
 65                  70                  75                  80

His Asp Lys Pro Glu Glu Val Val Glu Ile Val Lys Val Ala
                 85                  90                  95

Gly Met Phe Ala Val Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Ala Ala
    130                 135                 140

Phe Asn Arg Ala Gly Val Lys Ser Ile Lys Asn Arg Val Thr Thr
145                 150                 155                 160

Leu Glu Asp Phe Arg Ala Ala Leu Gln Glu Ile Gly Thr Pro Leu Ile
                165                 170                 175

Leu Lys Pro Thr Tyr Leu Ala Ser Ser Ile Gly Val Thr Leu Ile Lys
            180                 185                 190

Glu Arg Glu Thr Ala Glu Ala Glu Phe Asn Arg Val Asn Glu Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Asp Asp Trp Tyr Glu Thr Ser
225                 230                 235                 240

Gly Tyr Ser Asp Tyr Ile Ser Ile Glu Gly Ile Met Ala Asp Gly Glu
                245                 250                 255

Tyr Phe Pro Val Ala Ile His Asp Lys Thr Pro Gln Ile Gly Phe Thr
            260                 265                 270

Glu Thr Ser His Ile Thr Pro Ser Ile Leu Asp Asp Ala Lys Arg
        275                 280                 285

Lys Ile Val Glu Ala Ala Lys Lys Ala Asn Glu Gly Leu Gly Leu Glu
    290                 295                 300

Asn Cys Ala Thr His Thr Glu Ile Lys Leu Met Lys Asn Arg Glu Ala
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Val Asp Met Ala Gln Leu Leu Leu Asp
            340                 345                 350

Val Leu Cys Phe Gly Lys Glu Ala Asp Leu Pro Lys Gly Leu Leu Glu
        355                 360                 365
```

```
Gln Glu Pro Cys Tyr Val Ala Asp Cys His Leu Tyr Pro Gln His Phe
    370                 375                 380

Lys Glu Asn Gly Gln Leu Pro Glu Thr Ala Val Asp Phe Val Ile Glu
385                 390                 395                 400

Ser Ile Asp Ile Pro Asp Gly Val Leu Lys Gly Asp Thr Glu Ile Val
                405                 410                 415

Ser Phe Ser Ala Ala Glu Ala Gly Thr Ser Val Asp Leu Arg Leu Phe
                420                 425                 430

Glu Ala Phe Asn Ser Ile Ala Ala Phe Glu Leu Lys Gly Ser Asn Ser
                435                 440                 445

Gly Asp Val Ala Glu Ser Ile Lys Gln Ile Gln Gln Ala Lys Leu
    450                 455                 460

Thr Ala Lys Tyr Ala Leu Pro Val
465                 470

<210> SEQ ID NO 8
<211> LENGTH: 476
<212> TYPE: PRT
<213> ORGANISM: Bacillus pumilus NRRL B-12025

<400> SEQUENCE: 8

Val Leu Ser Leu Ser Lys Lys Thr Val Leu Val Ile Ala Asp Leu Gly
1               5                   10                  15

Gly Cys Pro Pro His Met Phe Tyr Glu Ser Val Ala Ala Ser Tyr His
                20                  25                  30

Ile Val Ser Tyr Ile Pro Arg Pro Phe Ala Ile Thr Lys Gly His Ala
            35                  40                  45

Glu Leu Ile Glu Lys Tyr Ser Ile Ala Val Ile Lys Asp Arg Asp Tyr
        50                  55                  60

Phe Glu Thr His Pro Ser Phe Glu His Pro Asp Ser Ile Tyr Trp Ala
65                  70                  75                  80

His Asp Asp Tyr Pro Lys Ser Glu Glu Val Val Glu Asp Phe Ile
                85                  90                  95

Arg Val Ala Ser Phe Phe Lys Asp Ala Ile Thr Thr Asn Asn Glu
            100                 105                 110

Leu Phe Ile Ala Pro Met Ala Lys Ala Ala Glu Arg Leu Gly Leu Arg
        115                 120                 125

Gly Ala Gly Val Lys Ala Ala Glu Met Ala Arg Asp Lys Ser Gln Met
    130                 135                 140

Arg Ala Ala Phe Asn Ala Ser Gly Val Lys Ala Val Lys Thr Gln Pro
145                 150                 155                 160

Val Thr Thr Leu Ser Asp Phe Gln Gln Ala Ile Glu Ser Ile Gly Thr
                165                 170                 175

Pro Leu Ile Leu Lys Pro Thr Tyr Leu Ala Ser Ser Ile Gly Val Thr
            180                 185                 190

Leu Phe His Asp Lys Ala Gly Ser Asp Asp Leu Phe Leu Gln Val Gln
        195                 200                 205

Ser Tyr Leu Glu Thr Ile Pro Val Pro Asp Ala Val Thr Tyr Glu Ala
    210                 215                 220

Pro Phe Val Ala Glu Thr Tyr Leu Glu Gly Ala Tyr Glu Asp Trp Tyr
225                 230                 235                 240

Glu Asp Glu Gly Tyr Ala Asp Tyr Val Ser Val Gly Leu Val Val
                245                 250                 255

Glu Gly Glu Tyr Leu Pro Phe Val Ile His Asp Lys Thr Pro Gln Ile
            260                 265                 270
```

```
Gly Phe Thr Glu Thr Ala His Ile Thr Pro Thr Ile Leu Asp Asn Glu
                275                 280                 285

Ala Lys Gln Ile Ile Glu Ala Ala Arg Lys Ala Asn Glu Gly Leu
        290                 295                 300

Gly Leu Glu His Cys Ala Thr His Thr Glu Ile Lys Leu Met Lys Asn
305                 310                 315                 320

Arg Glu Thr Gly Leu Ile Glu Ala Ala Arg Phe Ala Gly Trp Asn
                325                 330                 335

Met Ile Pro Asn Ile Lys Lys Val Phe Gly Val Asp Met Ala Lys Leu
                340                 345                 350

Leu Ile Asp Val Leu Val Asp Gly Lys Lys Ala Val Leu Pro Lys Gln
                355                 360                 365

Leu Leu Ser Gly His Thr Phe Tyr Val Ala Asp Cys His Leu Tyr Pro
                370                 375                 380

Gln His Phe Lys Glu Ser Gly Leu Ile Pro Pro Glu Ala Thr His Ile
385                 390                 395                 400

Thr Ile Asp His Val Ser Ile Pro Gln Glu Ala Phe Val Gly Asp Thr
                405                 410                 415

Ala Ile Val Ser Gln Ser Phe Pro Ala Lys Gly Thr Ile Val Asp Leu
                420                 425                 430

Glu Leu Phe Glu Ala Phe Asn Gly Ile Val Ser Leu Glu Leu Lys Gly
                435                 440                 445

Ser Ser Ser Gln Asp Val Ala Ala Ser Ile Arg Asn Ile Gln Lys Gln
                450                 455                 460

Ala Thr Ile Gln Leu Met Asp Glu Leu Val Lys Gly
465                 470                 475

<210> SEQ ID NO 9
<211> LENGTH: 1416
<212> TYPE: DNA
<213> ORGANISM: Bacillus subtilis 168

<400> SEQUENCE: 9 atg gag aga aaa aca gta ttg gtc atc gct gat ctt gga ggc tgc ccg      48
Met Glu Arg Lys Thr Val Leu Val Ile Ala Asp Leu Gly Gly Cys Pro
  1               5                  10                  15 ccg cac atg ttt tat aaa agc gct gct gaa aaa tat aac ctg gtc agc      96
Pro His Met Phe Tyr Lys Ser Ala Ala Glu Lys Tyr Asn Leu Val Ser
             20                  25                  30 ttt att cca aga cct ttt gca att aca gcc tcc cat gca gca ttg att     144
Phe Ile Pro Arg Pro Phe Ala Ile Thr Ala Ser His Ala Ala Leu Ile
         35                  40                  45 gaa aaa tac tcg gtc gcg gtc ata aaa gat aaa gac tat ttt aag agt     192
Glu Lys Tyr Ser Val Ala Val Ile Lys Asp Lys Asp Tyr Phe Lys Ser
     50                  55                  60 tta gct gat ttt gaa cac cct gat tcc att tat tgg gcg cat gaa gat     240
Leu Ala Asp Phe Glu His Pro Asp Ser Ile Tyr Trp Ala His Glu Asp
 65                  70                  75                  80 cat aac aag cct gag gaa gag gtc gtc gag caa atc gtc aag gtt gcc     288
His Asn Lys Pro Glu Glu Glu Val Val Glu Gln Ile Val Lys Val Ala
                 85                  90                  95 gaa atg ttt ggg gcg gat gcc atc aca aca aac aat gaa tta ttc att     336
Glu Met Phe Gly Ala Asp Ala Ile Thr Thr Asn Asn Glu Leu Phe Ile
            100                 105                 110 gct ccg atg gcg aaa gcc tgt gaa cgt ctg ggc ttg aga ggt gcc ggc     384
Ala Pro Met Ala Lys Ala Cys Glu Arg Leu Gly Leu Arg Gly Ala Gly
        115                 120                 125
```

```
gtg cag gca gcc gaa aat gcc aga gat aaa aat aaa atg agg gac gct      432
Val Gln Ala Ala Glu Asn Ala Arg Asp Lys Asn Lys Met Arg Asp Ala
    130                 135                 140 ttt aat aag gcc gga gtc aaa tcg atc aaa aac aaa cga gtc aca act      480
Phe Asn Lys Ala Gly Val Lys Ser Ile Lys Asn Lys Arg Val Thr Thr
145                 150                 155                 160 ctt gaa gat ttc cgt gct gct ctt gaa gag atc ggc aca cct ctt atc      528
Leu Glu Asp Phe Arg Ala Ala Leu Glu Glu Ile Gly Thr Pro Leu Ile
                165                 170                 175 tta aag cct aca tac tta gcg agt tct atc ggt gta acg ctg att acg      576
Leu Lys Pro Thr Tyr Leu Ala Ser Ser Ile Gly Val Thr Leu Ile Thr
            180                 185                 190 gac act gag acg gca gaa gat gaa ttt aac aga gtc aat gac tat ctg      624
Asp Thr Glu Thr Ala Glu Asp Glu Phe Asn Arg Val Asn Asp Tyr Leu
        195                 200                 205 aaa tca att aac gtg cca aag gcg gtt acg ttt gaa gcg ccg ttt atc      672
Lys Ser Ile Asn Val Pro Lys Ala Val Thr Phe Glu Ala Pro Phe Ile
    210                 215                 220 gct gaa gaa ttt tta cag ggt gag tac gga gac tgg tat caa aca gaa      720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag      768
Gly Tyr Ser Asp Tyr Ile Ser Ile Glu Gly Ile Met Ala Asp Gly Glu
                245                 250                 255 tat ttc ccg atc gcc att cat gat aaa acg ccg caa atc ggg ttt aca      816
Tyr Phe Pro Ile Ala Ile His Asp Lys Thr Pro Gln Ile Gly Phe Thr
            260                 265                 270 gag aca tcc cac att acg ccg tcc att ctg gat gaa gag gca aaa aag      864
Glu Thr Ser His Ile Thr Pro Ser Ile Leu Asp Glu Glu Ala Lys Lys
        275                 280                 285 aaa att gtc gaa gct gcc aaa aag gca aat gaa ggg ctt gga ctg caa      912
Lys Ile Val Glu Ala Ala Lys Lys Ala Asn Glu Gly Leu Gly Leu Gln
    290                 295                 300 aat tgc gca aca cat aca gag atc aag cta atg aaa aac aga gaa ccg      960
Asn Cys Ala Thr His Thr Glu Ile Lys Leu Met Lys Asn Arg Glu Pro
305                 310                 315                 320 ggt tta ata gag tcg gca gcc aga ttt gcc ggc tgg aat atg atc ccc     1008
Gly Leu Ile Glu Ser Ala Ala Arg Phe Ala Gly Trp Asn Met Ile Pro
                325                 330                 335 aat att aaa aag gtc ttt ggc ctt gat atg gcg caa tta tta tta gat     1056
Asn Ile Lys Lys Val Phe Gly Leu Asp Met Ala Gln Leu Leu Leu Asp
            340                 345                 350 gtc ctc tgt ttc gga aaa gac gcc gat ctg ccg gac gga tta ttg gat     1104
Val Leu Cys Phe Gly Lys Asp Ala Asp Leu Pro Asp Gly Leu Leu Asp
        355                 360                 365 caa gag cct tat tat gtt gcc gac tgc cat ttg tac ccg cag cat ttc     1152
Gln Glu Pro Tyr Tyr Val Ala Asp Cys His Leu Tyr Pro Gln His Phe
    370                 375                 380 aaa caa aat ggc caa att cct gaa act gct gag gat ttg gtc att gaa     1200
Lys Gln Asn Gly Gln Ile Pro Glu Thr Ala Glu Asp Leu Val Ile Glu
385                 390                 395                 400 gcg atc gat att ccg gac ggg ctt tta aaa ggg gat act gaa atc gtt     1248
Ala Ile Asp Ile Pro Asp Gly Leu Leu Lys Gly Asp Thr Glu Ile Val
                405                 410                 415 tct ttt tcg gcc gca gca cca ggc act tca gtt gat ttg aca ttg ttt     1296
Ser Phe Ser Ala Ala Ala Pro Gly Thr Ser Val Asp Leu Thr Leu Phe
            420                 425                 430 gaa gct ttc aat tcc att gct gca ttt gaa ctg aaa ggc agt aat tca     1344
Glu Ala Phe Asn Ser Ile Ala Ala Phe Glu Leu Lys Gly Ser Asn Ser
```

```
                      435                 440                 445
cag gat gtg gct gaa tca atc aga caa att cag cag cat gcg aag ctg    1392
Gln Asp Val Ala Glu Ser Ile Arg Gln Ile Gln Gln His Ala Lys Leu
        450                 455                 460 acg gca aag tat gtg ctg cca gta                                    1416
Thr Ala Lys Tyr Val Leu Pro Val
465                 470

<210> SEQ ID NO 10
<211> LENGTH: 1416
<212> TYPE: DNA
<213> ORGANISM: Bacillus subtilis ATCC6633

<400> SEQUENCE: 10 atg gag aga aaa aca gta ttg gtc atc gct gat ctt gga ggc tgc ccg    48
Met Glu Arg Lys Thr Val Leu Val Ile Ala Asp Leu Gly Gly Cys Pro
1               5                  10                  15 ccg cac atg ttt tat aaa agc gct gct gaa aaa tat aac ctg gtt agc    96
Pro His Met Phe Tyr Lys Ser Ala Ala Glu Lys Tyr Asn Leu Val Ser
                20                  25                  30 ttt att ccg aga cct ttt gca ata aca gcc tcc cat gca gca ctg att    144
Phe Ile Pro Arg Pro Phe Ala Ile Thr Ala Ser His Ala Ala Leu Ile
            35                  40                  45 gaa aaa tac tcg gtc gcg gta ata aaa gat aaa gac tat ttt cag agc    192
Glu Lys Tyr Ser Val Ala Val Ile Lys Asp Lys Asp Tyr Phe Gln Ser
        50                  55                  60 tta gct gat ttt gag cat ccc gat tca att tat tgg gcg cat gag gat    240
Leu Ala Asp Phe Glu His Pro Asp Ser Ile Tyr Trp Ala His Glu Asp
65                  70                  75                  80 cat gac aag cct gaa gaa gag gtt gtc gag caa atc gtc aag gtt gcc    288
His Asp Lys Pro Glu Glu Glu Val Val Glu Gln Ile Val Lys Val Ala
                85                  90                  95 caa atg ttt gag gcg gac gcc atc aca aca aac aat gaa tta ttc att    336
Gln Met Phe Glu Ala Asp Ala Ile Thr Thr Asn Asn Glu Leu Phe Ile
            100                 105                 110 gcc ccg atg gcg aaa gcc tgt gaa cgc ctt ggc ctg agg ggc gcc gga    384
Ala Pro Met Ala Lys Ala Cys Glu Arg Leu Gly Leu Arg Gly Ala Gly
        115                 120                 125 gtg cag gca gcg gaa aat gcc aga gat aaa aat aaa atg agg gac gct    432
Val Gln Ala Ala Glu Asn Ala Arg Asp Lys Asn Lys Met Arg Asp Ala
    130                 135                 140 ttt aat aag gcg gga gtc aaa tcg atc aaa aac aaa cga gtc aca act    480
Phe Asn Lys Ala Gly Val Lys Ser Ile Lys Asn Lys Arg Val Thr Thr
145                 150                 155                 160 ctt gag gat ttt cgt gct gca ctt gaa gag atc ggc aca cct cta atc    528
Leu Glu Asp Phe Arg Ala Ala Leu Glu Glu Ile Gly Thr Pro Leu Ile
                165                 170                 175 tta aag cct aca tac tta gcg agt tca atc ggc gta acg ctg att acc    576
Leu Lys Pro Thr Tyr Leu Ala Ser Ser Ile Gly Val Thr Leu Ile Thr
            180                 185                 190 gac acg gag acg gca gaa gat gaa ttt aac aga gtc aat gac tac ctg    624
Asp Thr Glu Thr Ala Glu Asp Glu Phe Asn Arg Val Asn Asp Tyr Leu
        195                 200                 205 aaa tcg att aac gtg ccg aag gcg gtc aca ttt gaa gca ccg ttt att    672
Lys Ser Ile Asn Val Pro Lys Ala Val Thr Phe Glu Ala Pro Phe Ile
    210                 215                 220 gct gag gaa ttt tta cag ggt gag tac gga gac tgg tat caa aca gaa    720
Ala Glu Glu Phe Leu Gln Gly Glu Tyr Gly Asp Trp Tyr Gln Thr Glu
225                 230                 235                 240 ggg tac tcc gac tat atc agc ata gaa ggc att atg gca gat ggt gag    768
```

```
Gly Tyr Ser Asp Tyr Ile Ser Ile Glu Gly Ile Met Ala Asp Gly Glu
            245                 250                 255 tat ttt ccg atc gcc att cat gac aaa acg ccg caa att gga ttt aca      816
Tyr Phe Pro Ile Ala Ile His Asp Lys Thr Pro Gln Ile Gly Phe Thr
        260                 265                 270 gag aca tca cat att acg cca tcc att ctg gat gaa gag gcg aaa aag      864
Glu Thr Ser His Ile Thr Pro Ser Ile Leu Asp Glu Glu Ala Lys Lys
    275                 280                 285 aaa att gtc gaa gcg gct aaa aag gca aat gaa ggg ctt gga ctg caa      912
Lys Ile Val Glu Ala Ala Lys Lys Ala Asn Glu Gly Leu Gly Leu Gln
290                 295                 300 aat tgc gca aca cat aca gaa atc aag cta atg aaa aac aga gaa ccg      960
Asn Cys Ala Thr His Thr Glu Ile Lys Leu Met Lys Asn Arg Glu Pro
305                 310                 315                 320 ggt tta ata gag tcg gct gcc aga ttc gca ggc tgg aat atg att cct     1008
Gly Leu Ile Glu Ser Ala Ala Arg Phe Ala Gly Trp Asn Met Ile Pro
                325                 330                 335 aac att aaa aag gtt ttc ggc ctt gat atg gcg caa tta tta tta gat     1056
Asn Ile Lys Lys Val Phe Gly Leu Asp Met Ala Gln Leu Leu Leu Asp
            340                 345                 350 gtt ctc tgt ttc gga aaa gat gct gat ctg ccg gac ggg tta ttg gat     1104
Val Leu Cys Phe Gly Lys Asp Ala Asp Leu Pro Asp Gly Leu Leu Asp
        355                 360                 365 caa gag cct tac tat gtt gct gac tgc cat ctg tac cct cag cat ttc     1152
Gln Glu Pro Tyr Tyr Val Ala Asp Cys His Leu Tyr Pro Gln His Phe
    370                 375                 380 aaa caa aat ggc cag atc cct gaa act gcc gag gat ttg gta atc gaa     1200
Lys Gln Asn Gly Gln Ile Pro Glu Thr Ala Glu Asp Leu Val Ile Glu
385                 390                 395                 400 gcg atc gat att ccg gat ggg ctt ttg aag ggt gat aca gaa atc gtt     1248
Ala Ile Asp Ile Pro Asp Gly Leu Leu Lys Gly Asp Thr Glu Ile Val
                405                 410                 415 act ttt tcg gct gcg gca cca gga aca tca gtt gat ttg aca ctg ttt     1296
Thr Phe Ser Ala Ala Ala Pro Gly Thr Ser Val Asp Leu Thr Leu Phe
            420                 425                 430 gaa gcc ttc aac tcc att gct gca ttt gaa ctg aaa ggc agc aat tca     1344
Glu Ala Phe Asn Ser Ile Ala Ala Phe Glu Leu Lys Gly Ser Asn Ser
        435                 440                 445 cag gat gtg gct gaa tca atc aga caa att cag cag cat gcg aag ctg     1392
Gln Asp Val Ala Glu Ser Ile Arg Gln Ile Gln Gln His Ala Lys Leu
    450                 455                 460 acg gca aag tat gtg ctg cca gta                                      1416
Thr Ala Lys Tyr Val Leu Pro Val
465                 470

<210> SEQ ID NO 11
<211> LENGTH: 1416
<212> TYPE: DNA
<213> ORGANISM: Bacillus subtilis IAM1213

<400> SEQUENCE: 11 atg gag aga aaa aca gta ttg gtc atc gct gat ctt gga ggc tgc ccg       48
Met Glu Arg Lys Thr Val Leu Val Ile Ala Asp Leu Gly Gly Cys Pro
1               5                  10                  15 ccg cac atg ttt tat aaa agc gct gct gaa aaa tat aac ctg gtc agc       96
Pro His Met Phe Tyr Lys Ser Ala Ala Glu Lys Tyr Asn Leu Val Ser
            20                  25                  30 ttt att cca aga cct ttt gca att aca gcc tcc cat gca gca ttg att      144
Phe Ile Pro Arg Pro Phe Ala Ile Thr Ala Ser His Ala Ala Leu Ile
        35                  40                  45
```

```
gaa aaa tac tcg gtc gcg gtc ata aaa gat aaa gac tat ttt aag agt    192
Glu Lys Tyr Ser Val Ala Val Ile Lys Asp Lys Asp Tyr Phe Lys Ser
     50              55                  60 tta gct gat ttt gag cat cct gac tcc att tat tgg gcg cat gag gat    240
Leu Ala Asp Phe Glu His Pro Asp Ser Ile Tyr Trp Ala His Glu Asp
 65              70                  75                  80 cat aac aag cct gag gaa gag gtc gtc gag caa atc gtc aag gtt gcc    288
His Asn Lys Pro Glu Glu Glu Val Val Glu Gln Ile Val Lys Val Ala
                 85                  90                  95 gaa atg ttt ggg gcg gat gcc atc aca aca aac aat gaa tta ttc att    336
Glu Met Phe Gly Ala Asp Ala Ile Thr Thr Asn Asn Glu Leu Phe Ile
                100                 105                 110 gct ccg atg gcg aaa gcc tgt gaa cgt ctg ggc ctg aga ggt gcc ggc    384
Ala Pro Met Ala Lys Ala Cys Glu Arg Leu Gly Leu Arg Gly Ala Gly
            115                 120                 125 gtg cag gca gcc gaa aat gcc aga gat aaa aat aaa atg agg gac gct    432
Val Gln Ala Ala Glu Asn Ala Arg Asp Lys Asn Lys Met Arg Asp Ala
130                 135                 140 ttt aat aag gcc gga gtc aaa tcg atc aaa aac aaa cga gtc aca act    480
Phe Asn Lys Ala Gly Val Lys Ser Ile Lys Asn Lys Arg Val Thr Thr
145                 150                 155                 160 ctc gaa gat ttc cgt gct gct ctt gaa gag atc ggc aca cct ctt atc    528
Leu Glu Asp Phe Arg Ala Ala Leu Glu Glu Ile Gly Thr Pro Leu Ile
                165                 170                 175 tta aag cct aca tac tta gcg agt tca atc ggt gta acg ctg att acg    576
Leu Lys Pro Thr Tyr Leu Ala Ser Ser Ile Gly Val Thr Leu Ile Thr
            180                 185                 190 gac act gag acg gca gaa gat gaa ttt aac aga gtc aat gac tat ctg    624
Asp Thr Glu Thr Ala Glu Asp Glu Phe Asn Arg Val Asn Asp Tyr Leu
        195                 200                 205 aaa tca att aac gtg cca aag gcg gtt acg ttt gaa gcg ccg ttt atc    672
Lys Ser Ile Asn Val Pro Lys Ala Val Thr Phe Glu Ala Pro Phe Ile
210                 215                 220 gct gaa gaa ttt tta cag ggt gag tac gga gac tgg tat caa aca gaa    720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag    768
Gly Tyr Ser Asp Tyr Ile Ser Ile Glu Gly Ile Met Ala Asp Gly Glu
                245                 250                 255 tat ttc ccg atc gcc att cat gat aaa acg ccg caa atc ggg ttt aca    816
Tyr Phe Pro Ile Ala Ile His Asp Lys Thr Pro Gln Ile Gly Phe Thr
            260                 265                 270 gag aca tcc cac att acg ccg tcc att ctg gat gaa gag gca aaa aag    864
Glu Thr Ser His Ile Thr Pro Ser Ile Leu Asp Glu Glu Ala Lys Lys
        275                 280                 285 aaa att gtc gaa gct gcc aaa aag gca aat gaa ggt ctt ggc ctg caa    912
Lys Ile Val Glu Ala Ala Lys Lys Ala Asn Glu Gly Leu Gly Leu Gln
290                 295                 300 aat tgc gca aca cat aca gag atc aag cta atg aaa aat aga gaa ccg    960
Asn Cys Ala Thr His Thr Glu Ile Lys Leu Met Lys Asn Arg Glu Pro
305                 310                 315                 320 ggt tta att gaa tcg gca gcc aga ttc gcc ggc tgg aat atg atc ccc   1008
Gly Leu Ile Glu Ser Ala Ala Arg Phe Ala Gly Trp Asn Met Ile Pro
                325                 330                 335 aat att aaa aag gtc ttt ggc ctt gat atg gcg caa tta tta tta gat   1056
Asn Ile Lys Lys Val Phe Gly Leu Asp Met Ala Gln Leu Leu Leu Asp
            340                 345                 350 gtc ctt tgt ttc gga aaa gac gcc gat ctg ccg gac gga tta ttg gat   1104
Val Leu Cys Phe Gly Lys Asp Ala Asp Leu Pro Asp Gly Leu Leu Asp
        355                 360                 365
```

```
caa gag cct tat tat gtt gcc gac tgc cat ttg tac ccg caa cat ttc      1152
Gln Glu Pro Tyr Tyr Val Ala Asp Cys His Leu Tyr Pro Gln His Phe
        370                 375                 380 aaa caa aat ggc cag att cca gaa act gct gag gat ttg gtc att gaa      1200
Lys Gln Asn Gly Gln Ile Pro Glu Thr Ala Glu Asp Leu Val Ile Glu
385                 390                 395                 400 gcg atc gat ctg cct gac ggg ctt tta aaa ggg gat act gag atc gtt      1248
Ala Ile Asp Leu Pro Asp Gly Leu Leu Lys Gly Asp Thr Glu Ile Val
                405                 410                 415 tct ttt tcg gcc gca gca cca gga act tca gtt gat ttg aca ttg ttt      1296
Ser Phe Ser Ala Ala Ala Pro Gly Thr Ser Val Asp Leu Thr Leu Phe
            420                 425                 430 gaa gct ttc aat tcc att gct gca ttt gaa ctg aaa ggc agt aat tca      1344
Glu Ala Phe Asn Ser Ile Ala Ala Phe Glu Leu Lys Gly Ser Asn Ser
        435                 440                 445 cag gat gtg gct gaa tca atc aga caa att cag cag cat gcg aag ctg      1392
Gln Asp Val Ala Glu Ser Ile Arg Gln Ile Gln Gln His Ala Lys Leu
450                 455                 460 acg gca aag tat gtg ctg cca gta                                       1416
Thr Ala Lys Tyr Val Leu Pro Val
465                 470

<210> SEQ ID NO 12
<211> LENGTH: 1416
<212> TYPE: DNA
<213> ORGANISM: Bacillus subtilis IAM1107

<400> SEQUENCE: 12 atg gag aga aaa aca gta ttg gtc atc gct gat ctt gga ggc tgc ccg       48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtc agc       96
Pro His Met Phe Tyr Lys Ser Ala Ala Glu Lys Tyr Asn Leu Val Ser
                20                  25                  30 ttt att cca aga cct ttt gca att aca gcc tcc cat gca gca ttg att      144
Phe Ile Pro Arg Pro Phe Ala Ile Thr Ala Ser His Ala Ala Leu Ile
            35                  40                  45 gaa aaa tac tcg gtc gcg gtc gta aaa gat aaa gac tat ttt aag agt      192
Glu Lys Tyr Ser Val Ala Val Val Lys Asp Lys Asp Tyr Phe Lys Ser
        50                  55                  60 tta gct gat ttt gag cat cct gac tcc att tat tgg gcg cat gag gat      240
Leu Ala Asp Phe Glu His Pro Asp Ser Ile Tyr Trp Ala His Glu Asp
65                  70                  75                  80 cat aac aag cct gag gaa gag gtc gtc gag caa atc gtc aag gtt gcc      288
His Asn Lys Pro Glu Glu Glu Val Val Glu Gln Ile Val Lys Val Ala
                85                  90                  95 gaa atg ttc ggg gcg gat gcc atc aca aca aac aat gaa tta ttc att      336
Glu Met Phe Gly Ala Asp Ala Ile Thr Thr Asn Asn Glu Leu Phe Ile
                100                 105                 110 gct ccg atg gcg aaa gcc tgt gaa cgt ctg ggc ttg aga ggt gcc ggc      384
Ala Pro Met Ala Lys Ala Cys Glu Arg Leu Gly Leu Arg Gly Ala Gly
            115                 120                 125 gtg cag gca gcc gaa aat gcc aga gat aaa aat aaa atg agg gac gct      432
Val Gln Ala Ala Glu Asn Ala Arg Asp Lys Asn Lys Met Arg Asp Ala
        130                 135                 140 ttt aat aag gcc gga gtc aaa tcg atc aaa aac aaa cga gtc aca act      480
Phe Asn Lys Ala Gly Val Lys Ser Ile Lys Asn Lys Arg Val Thr Thr
145                 150                 155                 160 ctt gaa gat ttc cgt gct gct ctt gaa gag atc ggc aca cct ctt atc      528
Leu Glu Asp Phe Arg Ala Ala Leu Glu Glu Ile Gly Thr Pro Leu Ile
```

-continued

|  | 165 |  |  |  | 170 |  |  |  | 175 |  |  |  |
|---|---|---|---|---|---|---|---|---|---|---|---|---|
| tta | aag | cct | aca | tac | tta | gcg | agt | tct | atc | ggt | gta | acg | ctg | att | acg | 576 |
| Leu | Lys | Pro | Thr | Tyr | Leu | Ala | Ser | Ser | Ile | Gly | Val | Thr | Leu | Ile | Thr |  |
|  |  |  | 180 |  |  |  | 185 |  |  |  | 190 |  |  |  |  |  |

```
tta aag cct aca tac tta gcg agt tct atc ggt gta acg ctg att acg      576
Leu Lys Pro Thr Tyr Leu Ala Ser Ser Ile Gly Val Thr Leu Ile Thr
            180                 185                 190 gac act gag acg gca gaa gat gaa ttt aac aga gtc aat gac tat ctg      624
Asp Thr Glu Thr Ala Glu Asp Glu Phe Asn Arg Val Asn Asp Tyr Leu
            195                 200                 205 aaa tca att aac gtg cca aag gcg gtt acg ttt gaa gcg ccg ttt atc      672
Lys Ser Ile Asn Val Pro Lys Ala Val Thr Phe Glu Ala Pro Phe Ile
    210                 215                 220 gct gaa gaa ttt tta cag ggt gag tac gga gac tgg tat caa aca gaa      720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag      768
Gly Tyr Ser Asp Tyr Ile Ser Ile Glu Gly Ile Met Ala Asp Gly Glu
                245                 250                 255 tat ttc ccg atc gcc att cat gat aaa acg ccg caa atc ggg ttt aca      816
Tyr Phe Pro Ile Ala Ile His Asp Lys Thr Pro Gln Ile Gly Phe Thr
            260                 265                 270 gag aca tcc cac att acg ccg tcc att ctg gat gaa gag gca aaa aag      864
Glu Thr Ser His Ile Thr Pro Ser Ile Leu Asp Glu Glu Ala Lys Lys
        275                 280                 285 aaa att gtc gaa gct gcc aaa aag gca aat gaa ggg ctt ggc ctg caa      912
Lys Ile Val Glu Ala Ala Lys Lys Ala Asn Glu Gly Leu Gly Leu Gln
290                 295                 300 aat tgc gca aca cat aca gag gtc aag cta atg aaa aac aga gaa ccg      960
Asn Cys Ala Thr His Thr Glu Val Lys Leu Met Lys Asn Arg Glu Pro
305                 310                 315                 320 ggt tta att gaa tcg gca gcc aga ttt gcc ggc tgg aat atg atc cct     1008
Gly Leu Ile Glu Ser Ala Ala Arg Phe Ala Gly Trp Asn Met Ile Pro
                325                 330                 335 aac att aaa aag gtt ttc ggc ctt gat atg gcg caa tta tta tta gat     1056
Asn Ile Lys Lys Val Phe Gly Leu Asp Met Ala Gln Leu Leu Leu Asp
            340                 345                 350 gtc ctc tgt ttc gga aaa gat gcc gat ctg ccg gac gga tta ttg gat     1104
Val Leu Cys Phe Gly Lys Asp Ala Asp Leu Pro Asp Gly Leu Leu Asp
        355                 360                 365 caa gag cct tac tat gtc gcc gac tgc cat ttg tac ccg cag cat ttc     1152
Gln Glu Pro Tyr Tyr Val Ala Asp Cys His Leu Tyr Pro Gln His Phe
370                 375                 380 aaa caa aat ggc cag att cca gaa acc gct gag gat ttg gtc att gaa     1200
Lys Gln Asn Gly Gln Ile Pro Glu Thr Ala Glu Asp Leu Val Ile Glu
385                 390                 395                 400 gcg atc gat att ccg gac ggg ctt tta aaa ggg gat act gaa atc ttt     1248
Ala Ile Asp Ile Pro Asp Gly Leu Leu Lys Gly Asp Thr Glu Ile Phe
                405                 410                 415 tct ttt tcg gcc gca gca cca ggc act tca gtt gat ttg aca ttg ttt     1296
Ser Phe Ser Ala Ala Ala Pro Gly Thr Ser Val Asp Leu Thr Leu Phe
            420                 425                 430 gaa gct ttc aat tcc att gct gca ttt gaa ctg aaa ggc agt aat tca     1344
Glu Ala Phe Asn Ser Ile Ala Ala Phe Glu Leu Lys Gly Ser Asn Ser
        435                 440                 445 cag gat gtg gct gaa tca atc aga caa att cag cag cat gcg aag ctg     1392
Gln Asp Val Ala Glu Ser Ile Arg Gln Ile Gln Gln His Ala Lys Leu
450                 455                 460 acg gca aag tat gtg ctg cca gta                                     1416
Thr Ala Lys Tyr Val Leu Pro Val
465                 470
```

<210> SEQ ID NO 13
<211> LENGTH: 1416
<212> TYPE: DNA
<213> ORGANISM: Bacillus subtilis IAM1214

<400> SEQUENCE: 13

```
atg gag aga aaa aca gta ttg gtc atc gct gat ctt gga ggc tgc ccg      48
Met Glu Arg Lys Thr Val Leu Val Ile Ala Asp Leu Gly Gly Cys Pro
1               5                   10                  15
ccg cac atg ttt tat aaa agc gct gct gaa aaa tat aac ctg gtt agc      96
Pro His Met Phe Tyr Lys Ser Ala Ala Glu Lys Tyr Asn Leu Val Ser
                20                  25                  30
ttt att ccg aga cct ttt gca ata aca gcc tcc cat gca gca ctg att     144
Phe Ile Pro Arg Pro Phe Ala Ile Thr Ala Ser His Ala Ala Leu Ile
            35                  40                  45
gaa aaa tac tcg gtc gcg gta ata aaa gat aaa gac tat ttt cag agc     192
Glu Lys Tyr Ser Val Ala Val Ile Lys Asp Lys Asp Tyr Phe Gln Ser
        50                  55                  60
tta gct gat ttt gag cat ccc gat tca att tat tgg gcg cat gag gat     240
Leu Ala Asp Phe Glu His Pro Asp Ser Ile Tyr Trp Ala His Glu Asp
65                  70                  75                  80
cat gac aag cct gaa gaa gag gtt gtc gag caa atc gtc aag gtt gcc     288
His Asp Lys Pro Glu Glu Glu Val Val Glu Gln Ile Val Lys Val Ala
                85                  90                  95
caa atg ttt gag gcg gac gcc atc aca aca aac aat gaa tta ttc att     336
Gln Met Phe Glu Ala Asp Ala Ile Thr Thr Asn Asn Glu Leu Phe Ile
                100                 105                 110
gcc ccg atg gcg aaa gcc tgt gaa cgc ctt ggc ctg agg ggc gcc gga     384
Ala Pro Met Ala Lys Ala Cys Glu Arg Leu Gly Leu Arg Gly Ala Gly
            115                 120                 125
gtg cag gca gcg gaa aat gcc aga gat aaa aat aaa atg agg gac gct     432
Val Gln Ala Ala Glu Asn Ala Arg Asp Lys Asn Lys Met Arg Asp Ala
        130                 135                 140
ttt aat aag gcg gga gtc aaa tcg atc aaa aac aaa cga gtc aca act     480
Phe Asn Lys Ala Gly Val Lys Ser Ile Lys Asn Lys Arg Val Thr Thr
145                 150                 155                 160
ctt gag gat ttt cgt gct gca ctt gaa gag atc ggc aca cct cta atc     528
Leu Glu Asp Phe Arg Ala Ala Leu Glu Glu Ile Gly Thr Pro Leu Ile
                165                 170                 175
tta aag cct aca tac tta gcg agt tca atc ggc gta acg ctg att acc     576
Leu Lys Pro Thr Tyr Leu Ala Ser Ser Ile Gly Val Thr Leu Ile Thr
                180                 185                 190
gac acg gag acg gca gaa gat gaa ttt aac aga gtc aat gac tac ctg     624
Asp Thr Glu Thr Ala Glu Asp Glu Phe Asn Arg Val Asn Asp Tyr Leu
            195                 200                 205
aaa tcg att aac gtg ccg aag gcg gtc aca ttt gaa gca ccg ttt att     672
Lys Ser Ile Asn Val Pro Lys Ala Val Thr Phe Glu Ala Pro Phe Ile
        210                 215                 220
gct gag gaa ttt tta cag ggt gag tac gga gac tgg tat caa aca gaa     720
Ala Glu Glu Phe Leu Gln Gly Glu Tyr Gly Asp Trp Tyr Gln Thr Glu
225                 230                 235                 240
ggg tac tcc gac tat atc agc ata gaa ggc att atg gca gat ggt gag     768
Gly Tyr Ser Asp Tyr Ile Ser Ile Glu Gly Ile Met Ala Asp Gly Glu
                245                 250                 255
tat ttt ccg atc gcc att cat gac aaa acg ccg caa att gga ttt aca     816
Tyr Phe Pro Ile Ala Ile His Asp Lys Thr Pro Gln Ile Gly Phe Thr
                260                 265                 270
gag aca tca cat att acg cca tcc att ctg gat gaa gag gcg aaa aag     864
Glu Thr Ser His Ile Thr Pro Ser Ile Leu Asp Glu Glu Ala Lys Lys
            275                 280                 285
aaa att gtc gaa gcg gct aaa aag gca aat gaa ggg ctt gga ctg caa     912
Lys Ile Val Glu Ala Ala Lys Lys Ala Asn Glu Gly Leu Gly Leu Gln
        290                 295                 300
aat tgc gca aca cat aca gaa atc aag cta atg aaa aac aga gaa ccg     960
Asn Cys Ala Thr His Thr Glu Ile Lys Leu Met Lys Asn Arg Glu Pro
305                 310                 315                 320
ggt tta ata gag tcg gct gcc aga ttc gca ggc tgg aat atg att cct    1008
Gly Leu Ile Glu Ser Ala Ala Arg Phe Ala Gly Trp Asn Met Ile Pro
                325                 330                 335
aac att aaa aag gtt ttc ggc ctt gat atg gcg caa tta tta tta gat    1056
Asn Ile Lys Lys Val Phe Gly Leu Asp Met Ala Gln Leu Leu Leu Asp
                340                 345                 350
gtt ctc tgt ttc gga aaa gat gct gat ctg ccg gac ggg tta ttg gat    1104
Val Leu Cys Phe Gly Lys Asp Ala Asp Leu Pro Asp Gly Leu Leu Asp
            355                 360                 365
caa gag cct tac tat gtt gct gac tgc cat ctg tac cct cag cat ttc    1152
Gln Glu Pro Tyr Tyr Val Ala Asp Cys His Leu Tyr Pro Gln His Phe
        370                 375                 380
```

```
aaa caa aat ggc cag atc cct gaa act gcc gag gat ttg gta atc gaa      1200
Lys Gln Asn Gly Gln Ile Pro Glu Thr Ala Glu Asp Leu Val Ile Glu
385                 390                 395                 400
gcg atc gat att ccg gat ggg ctt ttg aag ggt gat aca gaa atc gtt      1248
Ala Ile Asp Ile Pro Asp Gly Leu Leu Lys Gly Asp Thr Glu Ile Val
            405                 410                 415
act ttt tcg gct gcg gca cca gga aca tca gtt gat ttg aca ctg ttt      1296
Thr Phe Ser Ala Ala Ala Pro Gly Thr Ser Val Asp Leu Thr Leu Phe
420                 425                 430
gaa gcc ttc aac tcc att gct gca ttt gaa ctg aaa ggc agc aat tca      1344
Glu Ala Phe Asn Ser Ile Ala Ala Phe Glu Leu Lys Gly Ser Asn Ser
        435                 440                 445
cag gat gtg gct gaa tca atc aga caa att cag cag cat gcg aag ctg      1392
Gln Asp Val Ala Glu Ser Ile Arg Gln Ile Gln Gln His Ala Lys Leu
    450                 455                 460
acg gca aag tat gtg ctg cca gta                                      1416
Thr Ala Lys Tyr Val Leu Pro Val
465                 470

<210> SEQ ID NO 14
<211> LENGTH: 1416
<212> TYPE: DNA
<213> ORGANISM: Bacillus subtilis ATCC21555

<400> SEQUENCE: 14 atg gag aga aaa aca gta ttg gtt atc gct gat ctt ggg ggc tgc ccg      48
Met Glu Arg Lys Thr Val Leu Val Ile Ala Asp Leu Gly Gly Cys Pro
1               5                   10                  15 ccg cat atg ttt tac aaa agc gca gcc gaa aaa tac aac ctc gtc agc      96
Pro His Met Phe Tyr Lys Ser Ala Ala Glu Lys Tyr Asn Leu Val Ser
            20                  25                  30 ttt att ccg aga ccc ttt gca att aca gcc tct cat gcg gcc tta att      144
Phe Ile Pro Arg Pro Phe Ala Ile Thr Ala Ser His Ala Ala Leu Ile
        35                  40                  45 gaa aaa tac tcg att gcg gtc att aaa gat aaa gac tat ttt aag agt      192
Glu Lys Tyr Ser Ile Ala Val Ile Lys Asp Lys Asp Tyr Phe Lys Ser
    50                  55                  60 ctg gct gat ttt gaa cat ccc gat tcg att tat tgg gct cat gaa gat      240
Leu Ala Asp Phe Glu His Pro Asp Ser Ile Tyr Trp Ala His Glu Asp
65                  70                  75                  80 cat gac aaa cct gag gaa gaa gtc gtc gaa gaa atc gtg aaa gtg gcc      288
His Asp Lys Pro Glu Glu Glu Val Val Glu Glu Ile Val Lys Val Ala
                85                  90                  95 gac atg ttt ggg gtt gac gcc att acg acc aac aat gaa ctg ttt atc      336
Asp Met Phe Gly Val Asp Ala Ile Thr Thr Asn Asn Glu Leu Phe Ile
            100                 105                 110 gct ccg atg gca aaa gcg tgt aaa cgt ctc ggc ctg cgg gga gcg ggc      384
Ala Pro Met Ala Lys Ala Cys Lys Arg Leu Gly Leu Arg Gly Ala Gly
        115                 120                 125 gta cag gcc gct gaa aac gcc aga gat aaa aat aaa atg aga gcc gcc      432
Val Gln Ala Ala Glu Asn Ala Arg Asp Lys Asn Lys Met Arg Ala Ala
    130                 135                 140 ttc aac cgg gcc ggc gtc aaa tcc atc aaa aac aaa cgg gtg acg acc      480
Phe Asn Arg Ala Gly Val Lys Ser Ile Lys Asn Lys Arg Val Thr Thr
145                 150                 155                 160 ctg gaa gat ttc cgc gcc gcg ctt cag gaa atc gga acg ccg ctt att      528
Leu Glu Asp Phe Arg Ala Ala Leu Gln Glu Ile Gly Thr Pro Leu Ile
                165                 170                 175 ctg aag cct aca tat ctg gca agc tcg atc ggc gtg acg ctt att aaa      576
Leu Lys Pro Thr Tyr Leu Ala Ser Ser Ile Gly Val Thr Leu Ile Lys
            180                 185                 190 gag atg gaa acg gcc gaa gct gaa ttc aac aga gtc aat gag tac ttg      624
Glu Met Glu Thr Ala Glu Ala Glu Phe Asn Arg Val Asn Glu Tyr Leu
        195                 200                 205
```

| | | |
|---|---|---|
| aaa tcg att aat gta ccg aaa gcg gtg acg ttt gaa gcg ccg ttt atc<br>Lys Ser Ile Asn Val Pro Lys Ala Val Thr Phe Glu Ala Pro Phe Ile<br>210                                 215                           220 | 672 |
| gcg gaa gaa ttc ttg cag ggc gag tat gat gac tgg tac gaa aca agc<br>Ala Glu Glu Phe Leu Gln Gly Glu Tyr Asp Asp Trp Tyr Glu Thr Ser<br>225                       230                       235                   240 | 720 |
| ggt tat tcc gac tat atc agc atc gaa ggc atc atg gcc gac gga gaa<br>Gly Tyr Ser Asp Tyr Ile Ser Ile Glu Gly Ile Met Ala Asp Gly Glu<br>                   245                       250                   255 | 768 |
| tac ttc ccc gtt gcg atc cat gat aaa aca ccg caa atc gga ttc acg<br>Tyr Phe Pro Val Ala Ile His Asp Lys Thr Pro Gln Ile Gly Phe Thr<br>                  260                       265                   270 | 816 |
| gag aca gcg cat att acg ccg tcc atc ctg gat gat gac gcc aag cgg<br>Glu Thr Ala His Ile Thr Pro Ser Ile Leu Asp Asp Asp Ala Lys Arg<br>275                                 280                       285 | 864 |
| aaa atc gtc gaa gct gcc aag aag gcg aat gaa gga ctc ggc ctc gaa<br>Lys Ile Val Glu Ala Ala Lys Lys Ala Asn Glu Gly Leu Gly Leu Glu<br>         290                       295                       300 | 912 |
| aac tgt gca acg cat aca gaa ata aaa tta atg aaa aac cgg gaa gcc<br>Asn Cys Ala Thr His Thr Glu Ile Lys Leu Met Lys Asn Arg Glu Ala<br>305                                 310                       315                   320 | 960 |
| gga ctg att gag tca gcg gcc aga ttc gcg gga tgg aat atg att ccg<br>Gly Leu Ile Glu Ser Ala Ala Arg Phe Ala Gly Trp Asn Met Ile Pro<br>                       325                       330                   335 | 1008 |
| aat att aaa aag gtc ttc ggc gtt gat atg gcg cag cta tta ttg gat<br>Asn Ile Lys Lys Val Phe Gly Val Asp Met Ala Gln Leu Leu Leu Asp<br>                  340                       345                   350 | 1056 |
| gtt ctc tgt tac gga aaa gaa gct gat ctg ccg aaa gga tta ttg gag<br>Val Leu Cys Tyr Gly Lys Glu Ala Asp Leu Pro Lys Gly Leu Leu Glu<br>355                                 360                       365 | 1104 |
| cag gag cca tgc tat gtc gca gac tgc cac ttg tat cct cag cat ttc<br>Gln Glu Pro Cys Tyr Val Ala Asp Cys His Leu Tyr Pro Gln His Phe<br>         370                       375                       380 | 1152 |
| aaa gag aac ggc cag ctg cct gag acg gtt gtc gat ttc gtc att gaa<br>Lys Glu Asn Gly Gln Leu Pro Glu Thr Val Val Asp Phe Val Ile Glu<br>385                                 390                       395                   400 | 1200 |
| agc att gaa att cct gac ggc gtc tta aag gga gac act gaa ctc gtt<br>Ser Ile Glu Ile Pro Asp Gly Val Leu Lys Gly Asp Thr Glu Leu Val<br>                       405                       410                   415 | 1248 |
| tct ttc tca gcg gct gag gcg ggt acg tca gtg gat ctg cgg ctg ttc<br>Ser Phe Ser Ala Ala Glu Ala Gly Thr Ser Val Asp Leu Arg Leu Phe<br>                  420                       425                   430 | 1296 |
| gaa gcg ttc aac agc att gcg gcg ttt gag ctg aaa gga agc aat tcg<br>Glu Ala Phe Asn Ser Ile Ala Ala Phe Glu Leu Lys Gly Ser Asn Ser<br>435                                 440                       445 | 1344 |
| aac gac gtg gcc gaa tca atc aaa caa att cag cag cag gcg aag ctg<br>Asn Asp Val Ala Glu Ser Ile Lys Gln Ile Gln Gln Gln Ala Lys Leu<br>         450                       455                       460 | 1392 |
| act gca aag tat gcg tta tcg gta<br>Thr Ala Lys Tyr Ala Leu Ser Val | 1416 |

<210> SEQ ID NO 15
<211> LENGTH: 1416
<212> TYPE: DNA
<213> ORGANISM: Bacillus amyloliquefaciens IFO3022

<400> SEQUENCE: 15

| | |
|---|---|
| atg gag aga aaa aca gta ttg gtt atc gct gac ctt ggg gga tgc ccg<br>Met Glu Arg Lys Thr Val Leu Val Ile Ala Asp Leu Gly Gly Cys Pro<br>1                   5                       10                   15 | 48 |

| | | |
|---|---|---|
| ccg cat atg ttt tac aaa agc gca gcc gaa aaa tac aac ctc gtc agc<br>Pro His Met Phe Tyr Lys Ser Ala Ala Glu Lys Tyr Asn Leu Val Ser<br>20 25 30 | | 96 |
| ttt att ccg aga cct ttt gca att aca gcc tct cat gcg gca tta att<br>Phe Ile Pro Arg Pro Phe Ala Ile Thr Ala Ser His Ala Ala Leu Ile<br>35 40 45 | | 144 |
| gaa aaa tac tcg gtc gcg gtc ata aaa gat aaa gac tat ttt aag agt<br>Glu Lys Tyr Ser Val Ala Val Ile Lys Asp Lys Asp Tyr Phe Lys Ser<br>50 55 60 | | 192 |
| ctg gct gat ttt gag cat ccc gat tcg att tac tgg gct cat gaa gat<br>Leu Ala Asp Phe Glu His Pro Asp Ser Ile Tyr Trp Ala His Glu Asp<br>65 70 75 80 | | 240 |
| cat gac aaa cct gag gaa gaa gta gtc gaa gaa atc gtc aag gtg gcc<br>His Asp Lys Pro Glu Glu Glu Val Val Glu Glu Ile Val Lys Val Ala<br>85 90 95 | | 288 |
| ggc atg ttc gcg gtt gac gcc att acg acc aac aat gaa ctg ttt atc<br>Gly Met Phe Ala Val Asp Ala Ile Thr Thr Asn Asn Glu Leu Phe Ile<br>100 105 110 | | 336 |
| gct ccg atg gca aaa gcg tgt gaa cgt ctc ggc ctg cgg gga gcg ggc<br>Ala Pro Met Ala Lys Ala Cys Glu Arg Leu Gly Leu Arg Gly Ala Gly<br>115 120 125 | | 384 |
| gta cag gcc gct gaa aat gcc aga gat aaa aac aaa atg aga gcc gct<br>Val Gln Ala Ala Glu Asn Ala Arg Asp Lys Asn Lys Met Arg Ala Ala<br>130 135 140 | | 432 |
| ttc aac cgg gcc ggc gtc aag tct atc aaa aac aga cgg gtg acg acg<br>Phe Asn Arg Ala Gly Val Lys Ser Ile Lys Asn Arg Arg Val Thr Thr<br>145 150 155 160 | | 480 |
| ctg gaa gat ttc cgc gcc gcg ctt cag gaa atc gga acg ccg ctc att<br>Leu Glu Asp Phe Arg Ala Ala Leu Gln Glu Ile Gly Thr Pro Leu Ile<br>165 170 175 | | 528 |
| ctg aag cct aca tat ctg gcg agc tcc atc ggc gtg acg ctc atc aaa<br>Leu Lys Pro Thr Tyr Leu Ala Ser Ser Ile Gly Val Thr Leu Ile Lys<br>180 185 190 | | 576 |
| gag agg gaa acg gcc gaa gcc gaa ttt aac aga gtc aat gaa tac ctg<br>Glu Arg Glu Thr Ala Glu Ala Glu Phe Asn Arg Val Asn Glu Tyr Leu<br>195 200 205 | | 624 |
| aag tcg atc aac gta ccg aaa gcg gtc acg ttt gaa gcg ccg ttt atc<br>Lys Ser Ile Asn Val Pro Lys Ala Val Thr Phe Glu Ala Pro Phe Ile<br>210 215 220 | | 672 |
| gcg gaa gaa ttt ttg cag ggc gag tat gac gac tgg tac gaa aca agc<br>Ala Glu Glu Phe Leu Gln Gly Glu Tyr Asp Asp Trp Tyr Glu Thr Ser<br>225 230 235 240 | | 720 |
| ggt tat tcc gac tat atc agc ata gaa ggc atc atg gcc gac gga gaa<br>Gly Tyr Ser Asp Tyr Ile Ser Ile Glu Gly Ile Met Ala Asp Gly Glu<br>245 250 255 | | 768 |
| tac ttc cct gtc gca att cat gat aaa aca ccg caa atc gga ttc acg<br>Tyr Phe Pro Val Ala Ile His Asp Lys Thr Pro Gln Ile Gly Phe Thr<br>260 265 270 | | 816 |
| gag aca tcg cat att acg ccg tcc atc ctg gat gat gac gcg aag cgg<br>Glu Thr Ser His Ile Thr Pro Ser Ile Leu Asp Asp Asp Ala Lys Arg<br>275 280 285 | | 864 |
| aaa atc gtc gaa gca gcc aaa aag gcg aat gaa gga ctc ggc ctc gaa<br>Lys Ile Val Glu Ala Ala Lys Lys Ala Asn Glu Gly Leu Gly Leu Glu<br>290 295 300 | | 912 |
| aac tgc gca acc cat aca gag att aaa tta atg aaa aac cgg gaa gcc<br>Asn Cys Ala Thr His Thr Glu Ile Lys Leu Met Lys Asn Arg Glu Ala<br>305 310 315 320 | | 960 |
| gga ctg att gaa tca gcg gca cga ttt gcg ggc tgg aac atg att ccg<br>Gly Leu Ile Glu Ser Ala Ala Arg Phe Ala Gly Trp Asn Met Ile Pro<br>325 330 335 | | 1008 |

-continued

```
aat att aaa aag gtc ttc ggc gtc gat atg gcg cag ctg tta ttg gat      1056
Asn Ile Lys Lys Val Phe Gly Val Asp Met Ala Gln Leu Leu Leu Asp
            340                 345                 350 gtt ctc tgt ttc gga aaa gaa gcc gat ctg ccg aaa gga tta ttg gag      1104
Val Leu Cys Phe Gly Lys Glu Ala Asp Leu Pro Lys Gly Leu Leu Glu
        355                 360                 365 cag gag ccg tgc tat gtc gcc gac tgc cac ttg tat cct cag cat ttc      1152
Gln Glu Pro Cys Tyr Val Ala Asp Cys His Leu Tyr Pro Gln His Phe
    370                 375                 380 aaa gag aac ggc cag ctg cct gag acg gct gtc gat ttc gtc att gaa      1200
Lys Glu Asn Gly Gln Leu Pro Glu Thr Ala Val Asp Phe Val Ile Glu
385                 390                 395                 400 agc att gac att ccc gac ggc gtc tta aag gga gac acc gaa atc gtt      1248
Ser Ile Asp Ile Pro Asp Gly Val Leu Lys Gly Asp Thr Glu Ile Val
                405                 410                 415 tct ttc tcg gcg gcc gag gcg ggt aca tcc gtg gat ctg cgg ctg ttc      1296
Ser Phe Ser Ala Ala Glu Ala Gly Thr Ser Val Asp Leu Arg Leu Phe
            420                 425                 430 gaa gcg ttc aac agc att gcg gcg ttc gag ctg aaa gga agc aat tcg      1344
Glu Ala Phe Asn Ser Ile Ala Ala Phe Glu Leu Lys Gly Ser Asn Ser
        435                 440                 445 ggt gac gtg gcc gaa tca atc aaa caa att cag cag cag gcg aag ctg      1392
Gly Asp Val Ala Glu Ser Ile Lys Gln Ile Gln Gln Gln Ala Lys Leu
    450                 455                 460 act gca aag tat gcg tta ccg gta                                      1416
Thr Ala Lys Tyr Ala Leu Pro Val
```

<210> SEQ ID NO 16
<211> LENGTH: 1428
<212> TYPE: DNA
<213> ORGANISM: Bacillus pumilus NRRL B-12025

<400> SEQUENCE: 16

```
gtg ctt tca ttg agt aaa aaa act gta ctt gtc att gct gac tta gga        48
Val Leu Ser Leu Ser Lys Lys Thr Val Leu Val Ile Ala Asp Leu Gly
  1               5                  10                  15 ggg tgc ccg ccc cat atg ttt tat gaa agc gtg gcg gca tca tac cat        96
Gly Cys Pro Pro His Met Phe Tyr Glu Ser Val Ala Ala Ser Tyr His
            20                  25                  30 atc gtt tct tat atc cca aga ccc ttt gcg att aca aag gga cat gcc       144
Ile Val Ser Tyr Ile Pro Arg Pro Phe Ala Ile Thr Lys Gly His Ala
        35                  40                  45 gag cta atc gaa aaa tac tcc att gcc gtc atc aaa gac cgt gat tat       192
Glu Leu Ile Glu Lys Tyr Ser Ile Ala Val Ile Lys Asp Arg Asp Tyr
    50                  55                  60 ttt gag aca cac cct tct ttt gaa cac cct gat tct att tac tgg gca       240
Phe Glu Thr His Pro Ser Phe Glu His Pro Asp Ser Ile Tyr Trp Ala
 65                  70                  75                  80 cat gat gat tat cca aaa tca gaa gaa gaa gtt gtg gaa gac ttc att       288
His Asp Asp Tyr Pro Lys Ser Glu Glu Glu Val Val Glu Asp Phe Ile
                85                  90                  95 cga gta gct tcc ttt ttc aaa gca gat gca atc acg acc aat aat gaa       336
Arg Val Ala Ser Phe Phe Lys Ala Asp Ala Ile Thr Thr Asn Asn Glu
            100                 105                 110 tta ttc att gca ccg atg gca aag gcc gct gaa cgt ctt ggg cta cga       384
Leu Phe Ile Ala Pro Met Ala Lys Ala Ala Glu Arg Leu Gly Leu Arg
        115                 120                 125 ggt gcc ggt gtc aag gca gcc gaa atg gcg cgt gat aaa agc caa atg       432
Gly Ala Gly Val Lys Ala Ala Glu Met Ala Arg Asp Lys Ser Gln Met
    130                 135                 140
```

-continued

```
agg gct gca ttc aat gcc tct ggc gtc aaa gcg gtg aaa act cag cct     480
Arg Ala Ala Phe Asn Ala Ser Gly Val Lys Ala Val Lys Thr Gln Pro
145                 150                 155                 160 gtc acg act tta tct gat ttc caa caa gcc att gag tct atc gga aca     528
Val Thr Thr Leu Ser Asp Phe Gln Gln Ala Ile Glu Ser Ile Gly Thr
                165                 170                 175 ccg ctc att tta aag cct aca tat tta gcc agt tct att ggc gtc acc     576
Pro Leu Ile Leu Lys Pro Thr Tyr Leu Ala Ser Ser Ile Gly Val Thr
            180                 185                 190 ttg ttt cat gac aaa gcc gga agt gat gac ttg ttt tta caa gta caa     624
Leu Phe His Asp Lys Ala Gly Ser Asp Asp Leu Phe Leu Gln Val Gln
        195                 200                 205 tcg tat ttg gaa acc ata cca gtc cca gac gct gtc acg tat gaa gca     672
Ser Tyr Leu Glu Thr Ile Pro Val Pro Asp Ala Val Thr Tyr Glu Ala
    210                 215                 220 ccg ttt gtc gct gaa aca tat tta gag ggt gct tac gaa gat tgg tat     720
Pro Phe Val Ala Glu Thr Tyr Leu Glu Gly Ala Tyr Glu Asp Trp Tyr
225                 230                 235                 240 gaa gac gaa gga tat gct gat tat gtc agt gta gaa ggg ctg gtc gta     768
Glu Asp Glu Gly Tyr Ala Asp Tyr Val Ser Val Glu Gly Leu Val Val
                245                 250                 255 gag ggc gaa tat ctc cct ttt gtc ata cat gat aaa acc cct caa atc     816
Glu Gly Glu Tyr Leu Pro Phe Val Ile His Asp Lys Thr Pro Gln Ile
            260                 265                 270 ggc ttt aca gaa acg gct cat atc act ccg acg atc tta gac aat gaa     864
Gly Phe Thr Glu Thr Ala His Ile Thr Pro Thr Ile Leu Asp Asn Glu
        275                 280                 285 gcc aag caa atc atc att gaa gca gca agg aag gca aat gaa ggg cta     912
Ala Lys Gln Ile Ile Ile Glu Ala Ala Arg Lys Ala Asn Glu Gly Leu
    290                 295                 300 ggt ctt gaa cat tgt gca acc cat aca gaa atc aaa ctc atg aaa aat     960
Gly Leu Glu His Cys Ala Thr His Thr Glu Ile Lys Leu Met Lys Asn
305                 310                 315                 320 cga gaa act gga ctg atc gag gca gcg gct cga ttc gct ggc tgg aat    1008
Arg Glu Thr Gly Leu Ile Glu Ala Ala Ala Arg Phe Ala Gly Trp Asn
                325                 330                 335 atg atc ccg aat att aaa aaa gtc ttt ggc gtc gat atg gcg aag cta    1056
Met Ile Pro Asn Ile Lys Lys Val Phe Gly Val Asp Met Ala Lys Leu
            340                 345                 350 ttg att gat gta tta gtt gat ggt aaa aag gct gta ctg cca aaa cag    1104
Leu Ile Asp Val Leu Val Asp Gly Lys Lys Ala Val Leu Pro Lys Gln
        355                 360                 365 ctg ctt tct gga cat aca ttt tat gta gcg gac tgc cac ctg tac cct    1152
Leu Leu Ser Gly His Thr Phe Tyr Val Ala Asp Cys His Leu Tyr Pro
    370                 375                 380 cag cat ttt aaa gag agt ggg ctt atc ccg cct gaa gcc aca cat att    1200
Gln His Phe Lys Glu Ser Gly Leu Ile Pro Pro Glu Ala Thr His Ile
385                 390                 395                 400 acc att gat cat gtg tct att ccg cag gaa gca ttc gtt gga gat act    1248
Thr Ile Asp His Val Ser Ile Pro Gln Glu Ala Phe Val Gly Asp Thr
                405                 410                 415 gcg att gtc agt caa tca ttc cct gcc aaa ggg act att gtg gat ctt    1296
Ala Ile Val Ser Gln Ser Phe Pro Ala Lys Gly Thr Ile Val Asp Leu
            420                 425                 430 gaa tta ttt gaa gct ttt aat gga atc gta tct ctt gaa tta aaa gga    1344
Glu Leu Phe Glu Ala Phe Asn Gly Ile Val Ser Leu Glu Leu Lys Gly
        435                 440                 445 tca tcc tca caa gat gtt gcc gcg tcc atc cgc aac att cag aaa cag    1392
Ser Ser Ser Gln Asp Val Ala Ala Ser Ile Arg Asn Ile Gln Lys Gln
```

```
                450            455            460
gca acg att cag tta atg gat gaa tta gtg aag gga                    1428
Ala Thr Ile Gln Leu Met Asp Glu Leu Val Lys Gly
465                 470            475
```

<210> SEQ ID NO 17
<211> LENGTH: 93
<212> TYPE: PRT
<213> ORGANISM: Bacillus subtilis 168

<400> SEQUENCE: 17

```
Gly Ala Gly Val Gln Ala Ala Glu Asn Ala Arg Asp Lys Asn Lys Met
  1               5                  10                  15

Arg Asp Ala Phe Asn Lys Ala Gly Val Lys Ser Ile Lys Asn Lys Arg
             20                  25                  30

Val Thr Thr Leu Glu Asp Phe Arg Ala Ala Leu Glu Glu Ile Gly Thr
         35                  40                  45

Pro Leu Ile Leu Lys Pro Thr Tyr Leu Ala Ser Ser Ile Gly Val Thr
     50                  55                  60

Leu Ile Thr Asp Thr Glu Thr Ala Glu Asp Glu Phe Asn Arg Val Asn
 65                  70                  75                  80

Asp Tyr Leu Lys Ser Ile Asn Val Pro Lys Ala Val Thr
                 85                  90
```

<210> SEQ ID NO 18
<211> LENGTH: 279
<212> TYPE: DNA
<213> ORGANISM: Bacillus subtilis 168

<400> SEQUENCE: 18

```
ggt gcc ggc gtg cag gca gcc gaa aat gcc aga gat aaa aat aaa atg      48
Gly Ala Gly Val Gln Ala Ala Glu Asn Ala Arg Asp Lys Asn Lys Met
  1               5                  10                  15 agg gac gct ttt aat aag gcc gga gtc aaa tcg atc aaa aac aaa cga      96
Arg Asp Ala Phe Asn Lys Ala Gly Val Lys Ser Ile Lys Asn Lys Arg
             20                  25                  30 gtc aca act ctt gaa gat ttc cgt gct gct ctt gaa gag atc ggc aca     144
Val Thr Thr Leu Glu Asp Phe Arg Ala Ala Leu Glu Glu Ile Gly Thr
         35                  40                  45 cct ctt atc tta aag cct aca tac tta gcg agt tct atc ggt gta acg     192
Pro Leu Ile Leu Lys Pro Thr Tyr Leu Ala Ser Ser Ile Gly Val Thr
     50                  55                  60 ctg att acg gac act gag acg gca gaa gat gaa ttt aac aga gtc aat     240
Leu Ile Thr Asp Thr Glu Thr Ala Glu Asp Glu Phe Asn Arg Val Asn
 65                  70                  75                  80 gac tat ctg aaa tca att aac gtg cca aag gcg gtt acg                 279
Asp Tyr Leu Lys Ser Ile Asn Val Pro Lys Ala Val Thr
                 85                  90
```

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic DNA

<400> SEQUENCE: 19
attctcgagt agagaaggag tgttttacat                                     30

<210> SEQ ID NO 20

-continued

```
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20
ttaggatcct catactggca gcacatactt                                          30

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 21
caagaattct catgtttgac agct                                                24

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22
taactcgaga ttccctttt acgtgaac                                             28

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23
ttaaccatgg agagaaaaac agtattg                                             27

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 24
atatggatcc tactggcagc acatactttg                                          30

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 25
caccgcagac ggaggataca c                                                   21

<210> SEQ ID NO 26
<211> LENGTH: 22
```

<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 26
cggacgtcac ccaataatcg tg                                    22

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 27
ccgatggcra aagcstgtra acg                                   23

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 28
cggcagatcr gcdtcttttc c                                     21

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 29
gctaggtctt gaacattgtg caaccc                                26

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 30
ggtgttccga tagactcaat ggc                                   23

<210> SEQ ID NO 31
<211> LENGTH: 44
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 31
catgccatgg agaaaaaaac tgtacttgtc attgctgact tagg            44

<210> SEQ ID NO 32
<211> LENGTH: 38
<212> TYPE: DNA

<213> ORGANISM: Artificial Sequence
<220> FEATURE:
<223> OTHER INFORMATION: Description of Artificial Sequence: Synthetic
      DNA

<400> SEQUENCE: 32
cgcggatccc ttcactaatt catccattaa ctgaatcg                           38

<210> SEQ ID NO 33
<211> LENGTH: 12
<212> TYPE: PRT
<213> ORGANISM: Artificial Sequence
<220> FEATURE:
<221> NAME/KEY: UNS
      URE
<222> LOCATION: (3)
<223> OTHER INFORMATION: Xaa represents any amino acid selected from
      Ala, Arg,
      Asn, Asp, Cys, Glu, Gln, Gly, His, Ile, Leu, Lys, Met, Phe,
      Pro, Ser, Thr, Trp, Tyr and Val
<220> FEATURE:
<221> NAME/KEY: UNSURE
<222> LOCATION: (4)
<223> OTHER INFORMATION: Xaa represents any amino acid selected from
      Ala, Arg,
      Asn, Asp, Cys, Glu, Gln, Gly, His, Ile, Leu, Lys, Met, Phe,
      Pro, Ser, Thr, Trp, Tyr and Val
<220> FEATURE:
<221> NAME/KEY: UNSURE
<222> LOCATION: (9)
<223> OTHER INFORMATION: Xaa represents any amino acid selected from
      Ala, Arg, Asn,
      Asp, Cys, Glu, Gln, Gly, His, Ile, Leu, Lys, Met, Phe, Pro, Ser,
      Thr, Trp, Tyr and Val
<220> FEATURE:
<221> NAME/KEY: UNSURE
<222> LOCATION: (10)
<223> OTHER INFORMATION: Xaa represents any amino acid selected from
      Leu, Ile, Val,
      Met and Ala
<220> FEATURE:
<221> NAME/KEY: UNSURE
<222> LOCATION: (11)
<223> OTHER INFORMATION: Xaa represents Glu, Ser or Ala
<220> FEATURE:
<221> NAME/KEY: UNSURE
<222> LOCATION: (12)
<223> OTHER INFORMATION: Xaa represents Gly, Ser or Ala
<220> FEATURE:
<223> OTHER INFORMATION: Description of Artificial Sequence: Amino acid
      sequence
      used for data base search

<400> SEQUENCE: 33

His Gly Xaa Xaa Gly Gln Asp Gly Xaa Xaa Xaa Xaa
                5                   10

<210> SEQ ID NO 34
<211> LENGTH: 28
<212> TYPE: PRT
<213> ORGANISM: Artificial Sequence
<220> FEATURE:
<221> NAME/KEY: UNSURE
<222> LOCATION: (1)
<223> OTHER INFORMATION: Xaa represents Leu Ile or Val
<220> FEATURE:
<221> NAME/KEY: UNSURE
<222> LOCATION: (2)
<223> OTHER INFORMATION: Xaa represents any amino acid selected from
      Ala, Arg, Asn,
      Asp, Cys, Glu, Gln, Gly, His, Ile, Leu, Lys, Met, Phe, Pro, Ser,
      Thr, Trp, Tyr and Val
<220> FEATURE:
<221> NAME/KEY: UNSURE
<222> LOCATION: (3)

```
<223> OTHER INFORMATION: Xaa represents any amino acid selected from
      Ala, Arg, Asn,
      Asp, Cys, Glu, Gln, Gly, His, Ile, Leu, Lys, Met, Phe, Pro, Ser,
      Thr, Trp, Tyr and Val
<220> FEATURE:
<221> NAME/KEY: UNSURE
<222> LOCATION: (4)
<223> OTHER INFORMATION: Xaa represents any amino acid selected from
      Ala, Arg, Asn,
      Asp, Cys, Glu, Gln, Gly, His, Ile, Leu, Lys, Met, Phe, Pro, Ser,
      Thr, Trp, Tyr and Val
<220> FEATURE:
<221> NAME/KEY: UNSURE
<222> LOCATION: (5)
<223> OTHER INFORMATION: Xaa represents Gly or Ala
<220> FEATURE:
<221> NAME/KEY: UNSURE
<222> LOCATION: (6)
<223> OTHER INFORMATION: Xaa represents any amino acid selected from
      Ala, Arg, Asn,
      Asp, Cys, Glu, Gln, Gly, His, Ile, Leu, Lys, Met, Phe, Pro, Ser,
      Thr, Trp, Tyr and Val
<220> FEATURE:
<221> NAME/KEY: UNSURE
<222> LOCATION: (7)
<223> OTHER INFORMATION: Xaa represents any amino acid selected from
      Gly, Ser, Ala,
      Ile and Val
<220> FEATURE:
<221> NAME/KEY: UNSURE
<222> LOCATION: (9)
<223> OTHER INFORMATION: Xaa represents any amino acid selected from
      Leu, Ile, Val,
      Met, Cys and Ala
<220> FEATURE:
<221> NAME/KEY: UNSURE
<222> LOCATION: (11)
<223> OTHER INFORMATION: Xaa represents any amino acid selected from
      Leu, Ile, Val,
      Met, Phe and Ala
<220> FEATURE:
<221> NAME/KEY: UNSURE
<222> LOCATION: (12)
<223> OTHER INFORMATION: Xaa represents any amino acid selected from
      Leu, Ile, Val,
      Met, Phe and Ala
<220> FEATURE:
<221> NAME/KEY: UNSURE
<222> LOCATION: (13)
<223> OTHER INFORMATION: Xaa represents any amino acid selected from
      Ala, Arg, Asn,
      Asp, Cys, Glu, Gln, Gly, His, Ile, Leu, Lys, Met, Phe, Pro, Ser,
      Thr, Trp, Tyr and Val
<220> FEATURE:
<221> NAME/KEY: UNSURE
<222> LOCATION: (14)
<223> OTHER INFORMATION: Xaa represents any amino acid selected from
      Ala, Arg, Asn,
      Asp, Cys, Glu, Gln, Gly, His, Ile, Leu, Lys, Met, Phe, Pro, Ser,
      Thr, Trp, Tyr and Val
<220> FEATURE:
<221> NAME/KEY: UNSURE
<222> LOCATION: (15)
<223> OTHER INFORMATION: Xaa represents any amino acid selected from
      Ala, Arg, Asn,
      Asp, Cys, Glu, Gln, Gly, His, Ile, Leu, Lys, Met, Phe, Pro, Ser,
      Thr, Trp, Tyr and Val
<220> FEATURE:
<221> NAME/KEY: UNSURE
<222> LOCATION: (16)
<223> OTHER INFORMATION: Xaa represents any amino acid selected from
      Ala, Arg, Asn,
      Asp, Cys, Glu, Gln, Gly, His, Ile, Leu, Lys, Met, Phe, Pro, Ser,
      Thr, Trp, Tyr and Val
<220> FEATURE:
<221> NAME/KEY: UNSURE
<222> LOCATION: (17)
<223> OTHER INFORMATION: Xaa represents any amino acid selected from
      Ala, Arg, Asn,
```

-continued

```
      Asp, Cys, Glu, Gln, Gly, His, Ile, Leu, Lys, Met, Phe, Pro, Ser,
      Thr, Trp, Tyr and Val
<220> FEATURE:
<221> NAME/KEY: UNSURE
<222> LOCATION: (18)
<223> OTHER INFORMATION: Xaa represents any amino acid selected from
      Ala, Arg, Asn,
      Asp, Cys, Glu, Gln, Gly, His, Ile, Leu, Lys, Met, Phe, Pro, Ser,
      Thr, Trp, Tyr and Val
<220> FEATURE:
<221> NAME/KEY: UNSURE
<222> LOCATION: (19)
<223> OTHER INFORMATION: Xaa represents any amino acid selected from
      Ala, Arg, Asn,
      Asp, Cys, Glu, Gln, Gly, His, Ile, Leu, Lys, Met, Phe, Pro, Ser,
      Thr, Trp, Tyr and Val
<220> FEATURE:
<221> NAME/KEY: UNSURE
<222> LOCATION: (20)
<223> OTHER INFORMATION: Xaa represents Leu, Ile or Val
<220> FEATURE:
<221> NAME/KEY: UNSURE
<222> LOCATION: (21)
<223> OTHER INFORMATION: Xaa represents any amino acid selected from
      Ala, Arg, Asn, Asp, Cys, Glu, Gln, Gly, His, Ile, Leu, Lys,
      Met, Phe, Pro, Ser, Thr, Trp, Tyr and Val
<220> FEATURE:
<221> NAME/KEY: UNSURE
<222> LOCATION: (23)
<223> OTHER INFORMATION: Xaa represents any amino acid selected from
      Leu, Ile, Val, Ala and Pro
<220> FEATURE:
<221> NAME/KEY: UNSURE
<222> LOCATION: (25)
<223> OTHER INFORMATION: Xaa represents Ser, Thr or Pro
<220> FEATURE:
<221> NAME/KEY: UNSURE
<222> LOCATION: (26)
<223> OTHER INFORMATION: Xaa represents any amino acid selected from
      Ala, Arg, Asn, Asp, Cys, Glu, Gln, Gly, His, Ile, Leu, Lys,
      Met, Phe, Pro, Ser, Thr, Trp, Tyr and Val
<220> FEATURE:
<221> NAME/KEY: UNSURE
<222> LOCATION: (28)
<223> OTHER INFORMATION: Xaa represents Gly or Ala
<220> FEATURE:
<223> OTHER INFORMATION: Description of Artificial Sequence: Amino acid
      sequence used for data base search

<400> SEQUENCE: 34

Xaa Xaa Xaa Xaa Xaa Xaa Xaa Arg Xaa Asp Xaa Xaa Xaa Xaa Xaa Xaa
                 5                  10                  15

Xaa Xaa Xaa Xaa Xaa Gln Xaa Asn Xaa Xaa Pro Xaa
            20                  25

<210> SEQ ID NO 35
<211> LENGTH: 30
<212> TYPE: PRT
<213> ORGANISM: Artificial Sequence
<220> FEATURE:
<221> NAME/KEY: UNSURE
<222> LOCATION: (1)
<223> OTHER INFORMATION: Xaa represents Leu Ile or Val
<220> FEATURE:
<221> NAME/KEY: UNSURE
<222> LOCATION: (2)
<223> OTHER INFORMATION: Xaa represents any amino acid selected from
      Ala, Arg, Asn, Asp, Cys, Glu, Gln, Gly, His, Ile, Leu, Lys, Met,
      Phe, Pro, Ser, Thr, Trp, Tyr and Val
<220> FEATURE:
<221> NAME/KEY: UNSURE
<222> LOCATION: (3)
<223> OTHER INFORMATION: Xaa represents any amino acid selected from
      Ala, Arg, Asn, Asp, Cys, Glu, Gln, Gly, His, Ile, Leu, Lys, Met,
      Phe, Pro, Ser, Thr, Trp, Tyr and Val
<220> FEATURE:
```

```
<221> NAME/KEY: UNSURE
<222> LOCATION: (4)
<223> OTHER INFORMATION: Xaa represents any amino acid selected from
      Ala, Arg, Asn, Asp, Cys, Glu, Gln, Gly, His, Ile, Leu, Lys, Met,
      Phe, Pro, Ser, Thr, Trp, Tyr and Val
<220> FEATURE:
<221> NAME/KEY: UNSURE
<222> LOCATION: (5)
<223> OTHER INFORMATION: Xaa represents Gly or Ala
<220> FEATURE:
<221> NAME/KEY: UNSURE
<222> LOCATION: (6)
<223> OTHER INFORMATION: Xaa represents any amino acid selected from
      Ala, Arg, Asn, Asp, Cys, Glu, Gln, Gly, His, Ile, Leu, Lys, Met,
      Phe, Pro, Ser, Thr, Trp, Tyr and Val
<220> FEATURE:
<221> NAME/KEY: UNSURE
<222> LOCATION: (7)
<223> OTHER INFORMATION: Xaa represents any amino acid selected from
      Gly, Ser, Ala, Ile and Val
<220> FEATURE:
<221> NAME/KEY: UNSURE
<222> LOCATION: (9)
<223> OTHER INFORMATION: Xaa represents any amino acid selected from
      Leu, Ile, Val, Met, Cys and Ala
<220> FEATURE:
<221> NAME/KEY: UNSURE
<222> LOCATION: (11)
<223> OTHER INFORMATION: Xaa represents any amino acid selected from
      Leu, Ile, Val, Met, Phe and Ala
<220> FEATURE:
<221> NAME/KEY: UNSURE
<222> LOCATION: (12)
<223> OTHER INFORMATION: Xaa represents any amino acid selected from
      Leu, Ile, Val, Met, Phe and Ala
<220> FEATURE:
<221> NAME/KEY: UNSURE
<222> LOCATION: (13)
<223> OTHER INFORMATION: Xaa represents any amino acid selected from
      Ala, Arg, Asn, Asp, Cys, Glu, Gln, Gly, His, Ile, Leu, Lys, Met,
      Phe, Pro, Ser, Thr, Trp, Tyr and Val
<220> FEATURE:
<221> NAME/KEY: UNSURE
<222> LOCATION: (14)
<223> OTHER INFORMATION: Xaa represents any amino acid selected from
      Ala, Arg, Asn, Asp, Cys, Glu, Gln, Gly, His, Ile, Leu, Lys, Met,
      Phe, Pro, Ser, Thr, Trp, Tyr and Val
<220> FEATURE:
<221> NAME/KEY: UNSURE
<222> LOCATION: (15)
<223> OTHER INFORMATION: Xaa represents any amino acid selected
      from Ala, Arg, Asn, Asp, Cys, Glu, Gln, Gly, His, Ile, Leu, Lys,
      Met, Phe, Pro, Ser, Thr, Trp, Tyr and Val
<220> FEATURE:
<221> NAME/KEY: UNSURE
<222> LOCATION: (16)
<223> OTHER INFORMATION: Xaa represents any amino acid selected
      from Ala, Arg, Asn, Asp, Cys, Glu, Gln, Gly, His, Ile, Leu, Lys,
      Met, Phe, Pro, Ser, Thr, Trp, Tyr and Val
<220> FEATURE:
<221> NAME/KEY: UNSURE
<222> LOCATION: (17)
<223> OTHER INFORMATION: Xaa represents any amino acid selected
      from Ala, Arg, Asn, Asp, Cys, Glu, Gln, Gly, His, Ile, Leu, Lys,
      Met, Phe, Pro, Ser, Thr, Trp, Tyr and Val
<220> FEATURE:
<221> NAME/KEY: UNSURE
<222> LOCATION: (18)
<223> OTHER INFORMATION: Xaa represents any amino acid selected
      from Ala, Arg, Asn, Asp, Cys, Glu, Gln, Gly, His, Ile, Leu, Lys,
      Met, Phe, Pro, Ser, Thr, Trp, Tyr and Val
<220> FEATURE:
<221> NAME/KEY: UNSURE
<222> LOCATION: (19)
<223> OTHER INFORMATION: Xaa represents any amino acid selected
      from Ala, Arg, Asn, Asp, Cys, Glu, Gln, Gly, His, Ile, Leu, Lys,
      Met, Phe, Pro, Ser, Thr, Trp, Tyr and Val
<220> FEATURE:
<221> NAME/KEY: UNSURE
```

```
<222> LOCATION: (20)
<223> OTHER INFORMATION: Xaa represents any amino acid selected
      from Ala, Arg, Asn, Asp, Cys, Glu, Gln, Gly, His, Ile, Leu, Lys,
      Met, Phe, Pro, Ser, Thr, Trp, Tyr and Val
<220> FEATURE:
<221> NAME/KEY: UNSURE
<222> LOCATION: (21)
<223> OTHER INFORMATION: Xaa represents any amino acid selected
      from Ala, Arg, Asn, Asp, Cys, Glu, Gln, Gly, His, Ile, Leu, Lys,
      Met, Phe, Pro, Ser, Thr, Trp, Tyr and Val
<220> FEATURE:
<221> NAME/KEY: UNSURE
<222> LOCATION: (22)
<223> OTHER INFORMATION: Xaa represents Leu, Ile or Val
<220> FEATURE:
<221> NAME/KEY: UNSURE
<222> LOCATION: (23)
<223> OTHER INFORMATION: Xaa represents any amino acid selected
      from Ala, Arg, Asn, Asp, Cys, Glu, Gln, Gly, His, Ile, Leu, Lys,
      Met, Phe, Pro, Ser, Thr, Trp, Tyr and Val
<220> FEATURE:
<221> NAME/KEY: UNSURE
<222> LOCATION: (25)
<223> OTHER INFORMATION: Xaa represents any amino acid selected from
      Leu, Ile, Val, Ala and Pro
<220> FEATURE:
<221> NAME/KEY: UNSURE
<222> LOCATION: (27)
<223> OTHER INFORMATION: Xaa represents Ser, Thr or Pro
<220> FEATURE:
<221> NAME/KEY: UNSURE
<222> LOCATION: (28)
<223> OTHER INFORMATION: Xaa represents any amino acid selected
      from Ala, Arg, Asn, Asp, Cys, Glu, Gln, Gly, His, Ile, Leu, Lys,
      Met, Phe, Pro, Ser, Thr, Trp, Tyr and Val
<220> FEATURE:
<221> NAME/KEY: UNSURE
<222> LOCATION: (30)
<223> OTHER INFORMATION: Xaa represents Gly or Ala
<220> FEATURE:
<223> OTHER INFORMATION: Description of Artificial Sequence:
      Amino acid sequence used for data base search

<400> SEQUENCE: 35

Xaa Xaa Xaa Xaa Xaa Xaa Xaa Arg Xaa Asp Xaa Xaa Xaa Xaa Xaa Xaa
                 5                  10                  15

Xaa Xaa Xaa Xaa Xaa Xaa Xaa Gln Xaa Asn Xaa Xaa Pro Xaa
            20                  25                  30

<210> SEQ ID NO 36
<211> LENGTH: 1416
<212> TYPE: DNA
<213> ORGANISM: Bacillus subtilis ATCC 15245 and Bacillus subtilis
      IAM 1033

<400> SEQUENCE: 36 atg gag aga aaa aca gta ttg gtc atc gct gat ctt gga ggc tgc ccg      48
Met Glu Arg Lys Thr Val Leu Val Ile Ala Asp Leu Gly Gly Cys Pro
 1               5                  10                  15 ccg cac atg ttt tat aaa agc gct gct gaa aaa tat aac ctg gtc agc      96
Pro His Met Phe Tyr Lys Ser Ala Ala Glu Lys Tyr Asn Leu Val Ser
             20                  25                  30 ttt att cca aga cct ttt gca att aca gcc tcc cat gca gca ttg att     144
Phe Ile Pro Arg Pro Phe Ala Ile Thr Ala Ser His Ala Ala Leu Ile
         35                  40                  45 gaa aaa tac tcg gtc gcg gtc ata aaa gat aaa gac tat ttt aag agt     192
Glu Lys Tyr Ser Val Ala Val Ile Lys Asp Lys Asp Tyr Phe Lys Ser
     50                  55                  60 tta gct gat ttt gag cat cct gat tcc att tat tgg gcg cat gag gat     240
Leu Ala Asp Phe Glu His Pro Asp Ser Ile Tyr Trp Ala His Glu Asp
 65                  70                  75                  80
```

```
cat aac aag cct gag gaa gag gtc gtc gag caa atc gtc aag gtt gcc      288
His Asn Lys Pro Glu Glu Glu Val Val Glu Gln Ile Val Lys Val Ala
                85                  90                  95 gaa atg ttt ggg gcg gat gcc atc aca aca aac aat gaa tta ttc att      336
Glu Met Phe Gly Ala Asp Ala Ile Thr Thr Asn Asn Glu Leu Phe Ile
            100                 105                 110 gct ccg atg gcg aaa gcc tgt gaa cgt ctg ggc ctg aga ggt gcc ggc      384
Ala Pro Met Ala Lys Ala Cys Glu Arg Leu Gly Leu Arg Gly Ala Gly
        115                 120                 125 gtg cag gca gcc gaa aat gcc aga gat aaa aat aaa atg agg gac gct      432
Val Gln Ala Ala Glu Asn Ala Arg Asp Lys Asn Lys Met Arg Asp Ala
    130                 135                 140 ttt aat aag gcc gga gtc aaa tcg atc aaa aac aaa cga gtc aca act      480
Phe Asn Lys Ala Gly Val Lys Ser Ile Lys Asn Lys Arg Val Thr Thr
145                 150                 155                 160 ctt gaa gat ttc cgt gct gct ctt gaa gag atc ggc aca cct ctt atc      528
Leu Glu Asp Phe Arg Ala Ala Leu Glu Glu Ile Gly Thr Pro Leu Ile
                165                 170                 175 tta aag cct aca tac tta gcg agt tca atc ggt gta acg ctg att acg      576
Leu Lys Pro Thr Tyr Leu Ala Ser Ser Ile Gly Val Thr Leu Ile Thr
            180                 185                 190 gac act gag acg gca gaa gat gaa ttt aac aga gtc aat gac tat ctg      624
Asp Thr Glu Thr Ala Glu Asp Glu Phe Asn Arg Val Asn Asp Tyr Leu
        195                 200                 205 aaa tca att aac gtg cca aag gcg gtt acg ttt gaa gcg ccg ttt atc      672
Lys Ser Ile Asn Val Pro Lys Ala Val Thr Phe Glu Ala Pro Phe Ile
    210                 215                 220 gct gaa gaa ttt tta cag ggt gag tac gga gac tgg tat caa aca gaa      720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag      768
Gly Tyr Ser Asp Tyr Ile Ser Ile Glu Gly Ile Met Ala Asp Gly Glu
                245                 250                 255 tat ttc ccg atc gcc att cat gat aaa acg ccg caa atc ggg ttt aca      816
Tyr Phe Pro Ile Ala Ile His Asp Lys Thr Pro Gln Ile Gly Phe Thr
            260                 265                 270 gag aca tcc cac att acg ccg tcc att ctg gat gaa gag gca aaa aag      864
Glu Thr Ser His Ile Thr Pro Ser Ile Leu Asp Glu Glu Ala Lys Lys
        275                 280                 285 aaa att gtc gaa gct gcc aaa aag gca aat gaa ggg ctt ggc ctg caa      912
Lys Ile Val Glu Ala Ala Lys Lys Ala Asn Glu Gly Leu Gly Leu Gln
    290                 295                 300 aat tgc gca aca cat aca gag atc aag cta atg aaa aac aga gaa ccg      960
Asn Cys Ala Thr His Thr Glu Ile Lys Leu Met Lys Asn Arg Glu Pro
305                 310                 315                 320 ggt tta ata gag tcg gca gcc aga ttc gca ggc tgg aat atg att cct     1008
Gly Leu Ile Glu Ser Ala Ala Arg Phe Ala Gly Trp Asn Met Ile Pro
                325                 330                 335 aat att aaa aag gtc ttt ggc ctt gat atg gcg caa tta tta tta gat     1056
Asn Ile Lys Lys Val Phe Gly Leu Asp Met Ala Gln Leu Leu Leu Asp
            340                 345                 350 gtc ctc tgt ttc gga aaa gac gcc gat ctg ccg gac gga tta ttg gat     1104
Val Leu Cys Phe Gly Lys Asp Ala Asp Leu Pro Asp Gly Leu Leu Asp
        355                 360                 365 caa gag cct tat tat gtt gcc gac tgc cat ttg tac ccg cag cat ttc     1152
Gln Glu Pro Tyr Tyr Val Ala Asp Cys His Leu Tyr Pro Gln His Phe
    370                 375                 380 aaa caa aat ggc cag att cca gaa acc gct gag gat ttg gtc att gaa     1200
Lys Gln Asn Gly Gln Ile Pro Glu Thr Ala Glu Asp Leu Val Ile Glu
```

-continued

| | | | | | | | | | | | | | | |
|---|---|---|---|---|---|---|---|---|---|---|---|---|---|---|
| | | | | 385 | | | | 390 | | | | 395 | | 400 |
| gcg | atc | gat | att | ccg | gac | ggg | ctt | tta | aaa | ggg | gat | act | gaa | atc gtt | 1248 |
| Ala | Ile | Asp | Ile | Pro | Asp | Gly | Leu | Leu | Lys | Gly | Asp | Thr | Glu | Ile Val | |
| | | | | 405 | | | | | 410 | | | | | 415 | |
| tca | ttt | tca | gcc | gca | gca | cca | ggc | act | tca | gtt | gat | ttg | aca | ttg ttt | 1296 |
| Ser | Phe | Ser | Ala | Ala | Ala | Pro | Gly | Thr | Ser | Val | Asp | Leu | Thr | Leu Phe | |
| | | | 420 | | | | | 425 | | | | | 430 | | |
| gaa | gct | ttc | aat | tcc | att | gct | gca | ttt | gaa | ctg | aaa | ggc | agt | aat tca | 1344 |
| Glu | Ala | Phe | Asn | Ser | Ile | Ala | Ala | Phe | Glu | Leu | Lys | Gly | Ser | Asn Ser | |
| | | 435 | | | | | 440 | | | | | 445 | | | |
| cag | gat | gtg | gct | gaa | tca | atc | aga | caa | att | cag | cag | cat | gca | aag ctg | 1392 |
| Gln | Asp | Val | Ala | Glu | Ser | Ile | Arg | Gln | Ile | Gln | Gln | His | Ala | Lys Leu | |
| | 450 | | | | | 455 | | | | | 460 | | | | |
| acg | gca | aag | tat | gtg | ctg | cca | gta | | | | | | | | 1416 |
| Thr | Ala | Lys | Tyr | Val | Leu | Pro | Val | | | | | | | | |
| 465 | | | | | 470 | | | | | | | | | | |